(12) United States Patent
Furuta et al.

(10) Patent No.: US 8,084,625 B2
(45) Date of Patent: Dec. 27, 2011

(54) CROSSLINKING AGENT, CROSSLINKING METHOD, METHOD OF CONTROLLING GENE EXPRESSION, AND METHOD OF EXAMINING GENE FUNCTION

(75) Inventors: Toshiaki Furuta, Narashino (JP); Natsuyo Imaizumi, Ichihara (JP)

(73) Assignee: Wako Pure Chemical Industries, Ltd., Osaka-shi (JP)

( * ) Notice: Subject to any disclaimer, the term of this patent is extended or adjusted under 35 U.S.C. 154(b) by 1155 days.

(21) Appl. No.: 11/817,311

(22) PCT Filed: Feb. 27, 2006

(86) PCT No.: PCT/JP2006/303586
§ 371 (c)(1),
(2), (4) Date: Aug. 28, 2007

(87) PCT Pub. No.: WO2006/093083
PCT Pub. Date: Sep. 8, 2006

(65) Prior Publication Data
US 2009/0023140 A1    Jan. 22, 2009

(30) Foreign Application Priority Data
Mar. 3, 2005    (JP) .................................. 2005-058924

(51) Int. Cl.
*C07D 311/02* (2006.01)
*C07D 311/00* (2006.01)
(52) U.S. Cl. ...................................................... 549/284
(58) Field of Classification Search .................. 549/284, 549/290
See application file for complete search history.

(56) References Cited

U.S. PATENT DOCUMENTS

| | | | | |
|---|---|---|---|---|
| 2002/0155606 | A1* | 10/2002 | Okamoto et al. | 435/448 |
| 2003/0143612 | A1* | 7/2003 | Ault-Riche et al. | 435/6 |
| 2004/0053875 | A1 | 3/2004 | Kreutzer et al. | |
| 2004/0249178 | A1* | 12/2004 | Vargeese et al. | 552/506 |

FOREIGN PATENT DOCUMENTS

| | | |
|---|---|---|
| JP | 2002-315576 A | 10/2002 |
| JP | 2003-502012 A | 1/2003 |
| WO | WO 00/31588 A1 | 6/2000 |
| WO | WO 0031588 * | 6/2000 |
| WO | WO 2004/045547 A2 | 6/2004 |

OTHER PUBLICATIONS

Gao et al. STN Accession No. 1996:488342 , Abstract of Chinese Chemical Letters (1996), 7(8), 753-755.*
Furrow et al. Journal of the American Chemical Society, 2004, 126, 12222-12223.*
Ando et al., *Siekagaku*, 75(9): 1251-1254 (2003).
Bernstein et al., *Nature*, 409: 262-366 (2001).
Elbashir et al., *Genes & Dev.*, 15: 188-200 (2001).
Engels et al., *J. Med. Chem.*, 20(7): 907-911 (1977).
Fire et al., *Nature*, 391: 806-811 (1998).
Givens et al., *Tetrahedron Letters*, 37(35): 6259-6262 (1996).
Kaplan et al., *Biochemistry*, 17(10): 1929-1935 (1978).
Ordoukhanian et al., *Bioconjugate Chem.*, 11(1): 94-103 (2000).
Park et al., *J. Am. Chem. Soc.*, 119: 2453-2463 (1997).
Svoboda et al., *Development*, 127: 4147-4156 (2000).
Takaoka et al., *Bioorg. Med. Chem.*, 12(13): 3687-3694 (2004).
Zamore et al., *Cell*, 101: 25-33 (2000).

* cited by examiner

*Primary Examiner* — Nizal Chandrakumar
(74) *Attorney, Agent, or Firm* — Leydig, Voit & Mayer, Ltd.

(57) ABSTRACT

The present invention provides a crosslinking agent which have photodegradable protective groups at two ends to crosslink double-stranded nucleic acid, a nucleic acid and a protein or a polypeptide, or proteins or polypeptides, in particular, double-stranded RNA; a method for crosslinking a double-stranded RNA or the like using the same; a method for regulating gene expression, which can control the expression of a target gene at an arbitrary timing and location; and a method for examining a gene function.

According to the present invention, crosslinking between double-stranded nucleic acids between a nucleic acid and a protein or a polypeptide, or between proteins or polypeptides, in particular, between double-stranded RNA can be easily formed, and in addition, the crosslinking can also be easily removed, so that the expression of a target gene can be easily controlled at an arbitrary timing and location with high efficiency. Hence, as a result, function examination and/or identification of a gene that is expressed at a specific timing and location can be performed. In addition, the RNAi effect of a double-stranded RNA (siRNA) that cannot be easily inhibited by a conventional caged compound can be inhibited, and the expression of a target gene can be easily controlled at an arbitrary timing and location.

7 Claims, 9 Drawing Sheets

Fig. 8
| Lane | 1 | 2 | 3 | 4 |
|---|---|---|---|---|
Lamin B1
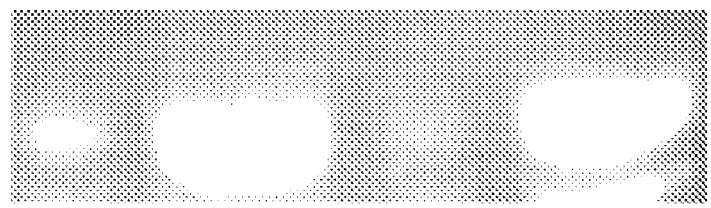
β-actin
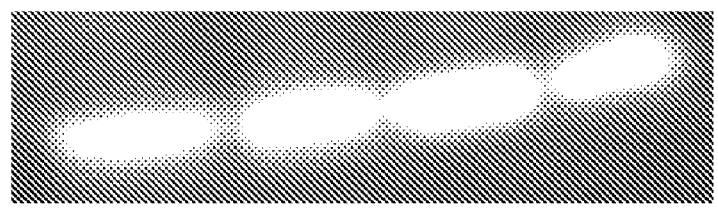
| | | | | |
|---|---|---|---|---|
| siRNA | + | + | + | − |
| Compound 3 of the Present Invention | + | + | − | − |
| UV Irradiation | + | − | − | − |

CROSSLINKING AGENT, CROSSLINKING METHOD, METHOD OF CONTROLLING GENE EXPRESSION, AND METHOD OF EXAMINING GENE FUNCTION

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 1,398 bytes ASCII (Text) file named "SequenceListing.txt," created Aug. 21, 2007.

TECHNICAL FIELD

The present invention relates to a crosslinking agent having photodegradable protective groups at two ends, a method for crosslinking a double-stranded nucleic acid, in particular a double-stranded RNA or the like, using the same, a method for regulating gene expression, and a method for examining a gene function.

BACKGROUND ART

In recent years, as a method for analyzing a gene function, there have been proposed various methods for regulating expression of a target gene to be analyzed.

Among those mentioned above, as a simple and powerful gene-function inhibition method, an RNA interference (RNAi) method has been widely used which uses a phenomenon in which expression of a target protein is specifically suppressed by a double-stranded RNA (dsRNA) that promotes specific decomposition of a target mRNA complementary thereto (Fire, A. et al., (1998), Nature 391, 806-811, Svobada, P. et al., (2000) Development 127, 4147-4156, Elbashir, S. M., Lendeckel, W. and Tuschl, T., (2001) Genes and Dev. 15, 188-200, Zamore, P. D. et al., (2000) Cell, 101, 25-33, Bernstein, E. et al., (2001) Nature, 409, 363-366, and the like).

In addition, so-called caged compounds each designed to regulate the activity of a target material using light have been variously developed. The caged compound is formed of a photodegradable protective group and has properties in which when it is bound to a target material, the target material is inactivated (caging), and when light is irradiated thereto, the cage is removed (uncaging), so that the original activity of the target material is restored (R. S. Givens, C. H. Park, Tetrahedron Lett., 37, 6259-6262 (1996), C. H. Park, R. S. Givens, J. Am. Chem. Soc., 119, 2453-2463 (1997), J Engels, E. J. Schlaeger, J. Med. Chem. 20, 907 (1977), J. H. Kaplan, G Forbush III, J. F. Hoffman, Biochemistry 17, 1920-1935 (1978), WO00/31588, and the like).

In biological fields, attention has been paid from early stage to the features of the cage compound, and recently, attempts have been made to regulate gene expression by using the caged compound as described above (Japanese Unexamined Patent Application Publication No. 2002-315576, Seikagaku (Biochemistry) vol. 75, No. 9, pp. 1251-1254, 2003, and the like).

This method is a method in which after an mRNA (single strand) is caged by a caged compound and is then transfected into a cell, the cell is pinpointedly irradiated with light or the like at an arbitrary timing and location, and as a result, translation of the target RNA (that is, the expression of protein) is conditionally performed.

In the above method, the expression of a target gene is suppressed by directly binding the caged compound to the single stranded mRNA; however, regulation of the expression of a target gene by suppressing the RNAi effect of an siRNA has not been reported, which is performed, for example, by crosslinking a double-stranded nucleotide, such as a double-stranded RNA (siRNA) used in the above RNAi or the like.

DISCLOSURE OF THE INVENTION

Problems to be Solved by the Invention

The present invention provides a crosslinking agent to crosslink double-stranded nucleic acid, a nucleic acid and a protein or a polypeptide, or proteins or polypeptides, in particular, double-stranded RNA; a method for crosslinking those described above; a simple method for regulating gene expression, which can control the expression of a target gene at an arbitrary timing and location; and a method for examining a gene function.

Means for Solving the Problems

The present invention has the following configurations.

1. A compound represented by the following general formula (1).

$$Q^1\text{-}A^1\text{-}T^1\text{-}A^2\text{-}Q^2 \quad (1)$$

(In the above formula, $Q^1$ and $Q^2$ each independently represent a photodegradable protective group; $A^1$ and $A^2$ each independently represent an alkylene group, —O—, —NR$^1$—, —O—CO—, —CO—O—, —C—O—C—, —NR$^2$—COO—, —OCO—NR$^2$—, —NR$^3$—CO—, —CO—NR$^3$—, or —O—COO— ($R^1$ to $R^3$ each independently represent hydrogen or an alkyl group); $T^1$ represents an alkylene group, an arylene group, an aralkylene group, an alkylene group containing a hetero atom, an arylene group containing a hetero atom, or an aralkylene group containing a hetero atom.)

2. A method comprising the step of crosslinking double-stranded nucleic acid, a nucleic acid and a protein or a peptide, or proteins or polypeptides by the compound described in the above 1.

3. A method for regulating gene expression, comprising the step of irradiating a double-stranded RNA bound beforehand with the compound described in the above 1 with ultraviolet light.

4. A method for regulating gene expression, comprising:
a step (a) of contacting a double-stranded RNA with the compound described in the above 1 to crosslink the double-stranded RNA;
a step (b) of transfecting the crosslinked double-stranded RNA into a cell or an organism; and
a step (c) of irradiating the transfected cell or organism with ultraviolet light.

5. A method for examining a gene function, comprising:
a step (a) of contacting a double-stranded RNA with the compound described in the above 1 to crosslink the double-stranded RNA;
a step (b) of transfecting the crosslinked double-stranded RNA into a cell or an organism;
a step (c) of irradiating the transfected cell or organism with ultraviolet light;
a step (c') of expressing a gene of the light-irradiated cell or organism; and
a step (d) of comparing the gene expressed in the step (c') with a control.

6. A crosslinking agent comprising the compound described in the above 1 to crosslink nucleic acids, a nucleic acid and a protein or a polypeptide, or proteins or polypeptides.

That is, the inventors of the present invention found that when a conventionally known caged compound is bound to a single stranded nucleotide chain, in particular, to RNA, although the expression of a target gene can be effectively suppressed, when an RNAi method is performed by binding a caged compound to a double-stranded RNA (siRNA), the RNAi effect of the siRNA can be hardly suppressed, and as a result, the expression of a target gene cannot be controlled.

Under these circumstances, through intensive research carried out by the inventors of the present invention in order to achieve the above object, it was found that when RNAi is performed by crosslinking a double-stranded RNA (siRNA) using a crosslinking agent having photodegradable protective groups at two ends, the expression of a target gene can be easily controlled at an arbitrary timing and location with high efficiency, and as a result, the present invention was made.

The crosslinking agent, the crosslinking method using the same, and the method for regulating gene expression as described above have not been performed in the past and have not been conceived at all.

EFFECT OF THE INVENTION

When a double-stranded RNA is crosslinked using the crosslinking agent of the present invention, the expression of a target gene can be easily controlled at an arbitrary timing and location with high efficiency, and as a result, function examination and/or identification of a gene which is specifically expressed at a certain timing and location can be performed.

BRIEF DESCRIPTION OF THE DRAWINGS

FIG. 8 shows the results of Western blotting obtained in Example 10.

BEST MODE FOR CARRYING OUT THE INVENTION

1. Compound of the Present Invention

Figure 1:
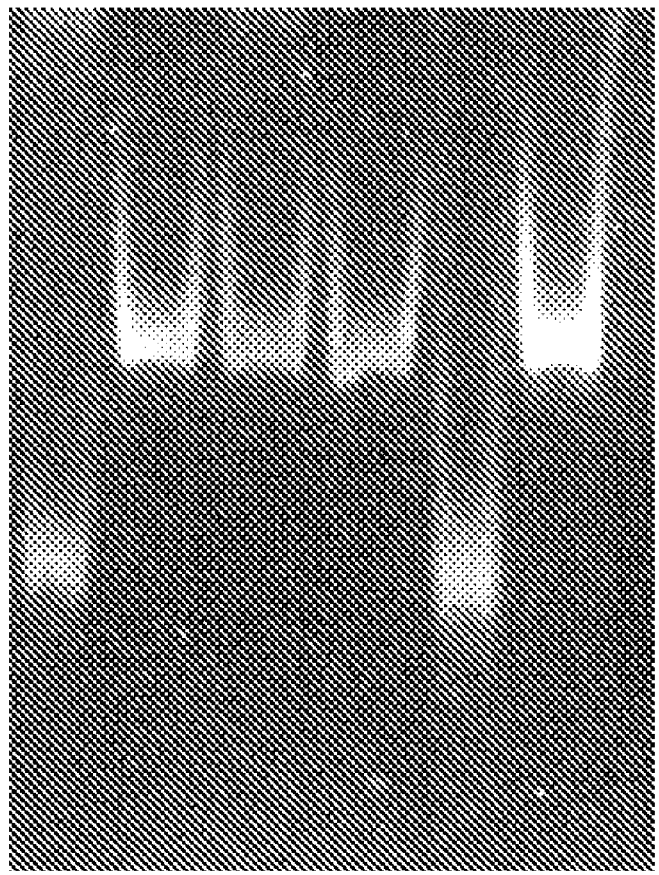
FIG. 1 shows the results of electrophoresis of samples obtained in Example 4.

The compound of the present invention has photodegradable protective groups at two ends and is a crosslinking agent to crosslink nucleic acids, a nucleic acid and a protein or a polypeptide, or proteins or polypeptides.

As the photodegradable protective group, a protective group may be mentioned having a group (hereinafter referred to as a "leaving group") which is bound to a phosphoric group, a carboxyl group, a hydroxyl group, an amino group, or the like and which is able to form a group causing a deprotection reaction by irradiation of light; a protective group having a group which can be bound to a group selected from a phosphoric group, a carboxyl group, a hydroxyl group, and an amino group is preferable; and above all, a protective group having a group which can be bound to a phosphoric group is particularly preferable.

In addition, the leaving groups of the photodegradable protective groups bound to the two ends are preferably bound to the two ends of the compound (crosslinking agent) of the present invention so as to have a distance therebetween which is sufficient to binds nucleic acids, a nucleic acid and a protein or a polypeptide, or proteins or polypeptides, that is, so as to have a distance therebetween which can crosslink a sense chain and an antisense chain of a double-stranded nucleic acid, a nucleic acid and a protein or a polypeptide, or two proteins or polypeptides (between proteins, between a protein and a polypeptide, or between polypeptides). In particular, the distance is preferably a distance sufficient to crosslink a sense chain and an antisense chain of a double-stranded RNA.

In more particular, since the distance between materials to be crosslinked varies depending on types thereof, a preferable distance between the photodegradable protective groups cannot be simply determined; however, the lower limit of the distance therebetween is generally 8 Å or more and preferably 15 Å or more, and the upper limit is generally 100 Å or less and preferably 80 Å or less.

For example, when nucleic acids (double-stranded DNA, double-stranded RNA, or double-stranded hybrid composed of DNA and RNA) are crosslinked, as the distance between the leaving groups of the photodegradable protective groups bound to the two ends, the lower limit is generally 8 Å or more, preferably 15 Å or more, and more preferably 25 Å or more, and the upper limit is generally 50 Å or less and preferably 35 Å or less.

When a nucleic acid and a protein or a polypeptide are crosslinked, or two proteins or two polypeptides are crosslinked, as the distance between the leaving groups of the photodegradable protective groups bound to the two ends, the lower limit is generally 10 Å or more and preferably 25 Å or more, and the upper limit is generally 100 Å or less and preferably 80 Å or less.

In particular, the compound of the present invention is represented by the following general formula (1).

$$Q^1\text{-}A^1\text{-}T^1\text{-}A^2\text{-}Q^2 \qquad (1)$$

(In the above formula, $Q^1$ and $Q^2$ each independently represent a photodegradable protective group; $A^1$ and $A^2$ each independently represent an alkylene group, —O—, —NR$^1$—, —O—CO—, —CO—O—, —C—O—C—, —NR$^2$—COO—, —OCO—NR$^2$—, —NR$^3$—CO—, —CO—NR$^3$—, or —O—COO— ($R^1$ to $R^3$ each independently represent hydrogen or an alkyl group); $T^1$ represents an alkylene group, an arylene group, an aralkylene group, an alkylene group containing a hetero atom, an arylene group containing a hetero atom, or an aralkylene group containing a hetero atom.)

The compound of the present invention represented by the general formula (1) can be divided into two constituent portions:

(a) photodegradable protective groups: $Q^1$ and $Q^2$; and
(b) a linker portion: $-A^1-T^1-A^2-$.

1-1. Photodegradable Protective Groups

In the general formula (1), as the photodegradable protective groups represented by $Q^1$ and $Q^2$, a protective group having a leaving group and causing a deprotection reaction by light irradiation may be mentioned, and in particular, a protective group having a group bindable to phosphoric group is preferable.

In more particular, photodegradable protective groups represented by the following general formulas (3), (3'), (3") and (3''') are mentioned.

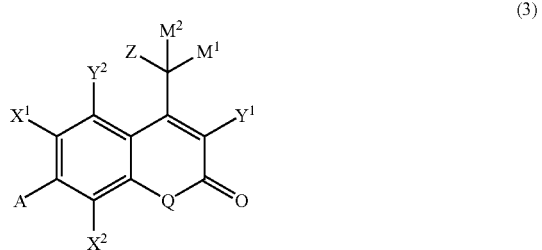

(3)

[In the general formula (3), one of $Y^1$, $Y^2$, $X^1$, $X^2$, A, and $M^1$ represents a binding hand to be bound to $A^1$ or $A^2$ of the general formula (1), and the other symbols represent as follows.

Q represents —O—, —NH—, or —NCH$_3$—; A represents a hydroxyl group, a substituted alkoxy group, an unsubstituted alkoxy group, —OC(O)R$^{11}$, —NH$_2$, —NHCH$_3$, or —NR$^{11}$R$^{12}$; $X^1$ and $X^2$ each independently represent —H, a hydroxyl group, a substituted alkoxy group, an unsubstituted alkoxy group, a —OC(O)R$^{11}$ group, a —NH$_3$ group, a —NR$^{11}$R$^{12}$ group, —R$^{11}$, —F, —Cl, —Br, —I, —COOH, —NO$_2$, —C(=O)NHR$^{11}$, —CN, —CHO, —C(=O)R$^{11}$, or —SO$_3$H; $Y^1$ represents —H, —Cl, —Br, —I, —C(O)OH, —NO$_2$, —C(O)NHR$^{11}$, —CN, —C(O)H, —C(O)CH$_3$, a benzoxazole-2-yl group, -benzothiazole-2-yl, or -benzoimidazole-2-yl; $Y^2$ represents —H, —C(O)OH, or —SO$_3$H; $M^1$ represents —H, —CH$_3$, —NR$^{12}$R$^{13}$ group, —C(O)NR$^{12}$R$^{13}$ group, or —COOH; and Z represents a leaving group. In addition, $M^2$ represents —H or represents =N$_2$, =O, or =NNHR$^{11}$ together with Z. R$^{11}$, R$^{12}$, and R$^{13}$ each independently represent a substituted or an unsubstituted functional group selected from an alkyl group having 1 to 20 carbon atoms, an alkenyl group having 2 to 20 carbon atoms, an alkynyl group having 2 to 20 carbon atoms, an alkoxy group having 1 to 20 carbon atoms, a thioalkoxy group having 1 to 20 carbon atoms, an alkylsulfonyl group having 1 to 20 carbon atoms, an arylsulfonyl group having 4 to 16 carbon atoms, a heteroalkyl group having a total number of carbon and hetero atoms of 2 to 20, a heteroalkenyl group having a total number of carbon and hetero atoms of 2 to 20, a cycloalkyl group having 3 to 8 carbon atoms, a cycloalkenyl group having 3 to 8 carbon atoms, an aryl group having 4 to 16 carbon atoms, a heteroaryl group having a total number of carbon and hetero atoms of 4 to 16, and a heterocyclyl group having a total number of carbon and hetero atoms of 2 to 30; and $X^1$ and A, $X^2$ and A, or $X^1$ and $Y^2$ may form in combination a group selected from an —O—(CH$_2$)$_n$—O— group, a —C—(CH$_2$)$_n$—O— group, an —O—(CH$_2$)$_n$—C— group, an —O—(CH$_2$)$_n$—N— group, a —N—(CH$_2$)$_n$—O— group, a —N—(CH$_2$)$_n$—N— group, a —C—(CH$_2$)$_n$—N— group, and a —N—(CH$_2$)$_n$—C— group, in which n is 1 or 2.)

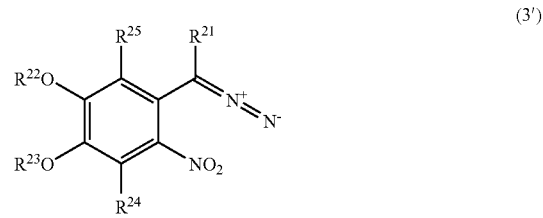

(3')

[In the general formula (3'), one of $R^{22}$ to $R^{25}$ represents a binding hand to be bound to $A^1$ or $A^2$ of the general formula (1), and the other symbols represent as follows.

$R^{21}$ represents a hydrogen atom, —COOH, or a substituted or an unsubstituted functional group selected from an alkyl group having 1 to 20 carbon atoms, an alkenyl group having 2 to 20 carbon atoms, an alkynyl group having 2 to 20 carbon atoms, an alkoxy group having 1 to 20 carbon atoms, a thioalkoxy group having 1 to 20 carbon atoms, an alkylsulfonyl group having 1 to 20 carbon atoms, an arylsulfonyl group having 4 to 16 carbon atoms, a heteroalkyl group having a total number of carbon and hetero atoms of 2 to 20, a heteroalkenyl group having a total number of carbon and hetero atoms of 2 to 20, a cycloalkyl group having 3 to 8 carbon atoms, a cycloalkenyl group having 3 to 8 carbon atoms, an aryl group having 4 to 16 carbon atoms, a heteroaryl group having a total number of carbon and hetero atoms of 4 to 16, and a heterocyclyl group having a total number of carbon and hetero atoms of 2 to 30;

$R^{22}$ and $R^{23}$ each independently represent a substituted or an unsubstituted functional group selected from an alkyl group having 1 to 20 carbon atoms, an alkenyl group having 2 to 20 carbon atoms, an alkynyl group having 2 to 20 carbon atoms, an alkoxy group having 1 to 20 carbon atoms, a thioalkoxy group having 1 to 20 carbon atoms, an alkylsulfonyl group having 1 to 20 carbon atoms, an arylsulfonyl group having 4 to 16 carbon atoms, a heteroalkyl group having a total number of carbon and hetero atoms of 2 to 20, a heteroalkenyl group having a total number of carbon and hetero atoms of 2 to 20, a cycloalkyl group having 3 to 8 carbon atoms, a cycloalkenyl group having 3 to 8 carbon atoms, an aryl group having 4 to 16 carbon atoms, a heteroaryl group having a total number of carbon and hetero atoms of 4 to 16, and a heterocyclyl group having a total number of carbon and hetero atoms of 2 to 30; $R^{24}$ and $R^{25}$ each represent a hydrogen atom; $R^{22}$ and $R^{23}$ may form in combination a —(CH$_2$)$_n$— group; $R^{23}$ and $R^{24}$ may form in combination a group selected from a —(CH$_2$)$_n$—O— group, a —(CH$_2$)$_n$—C— group, and an —(CH$_2$)$_n$—N— group; $R^{22}$ and $R^{25}$ may form in combination a group selected from a —O—(CH$_2$)$_n$— group, a —C—(CH$_2$)$_n$— group, and an —N—(CH$_2$)$_n$— group. In this case, n is 1 or 2.)

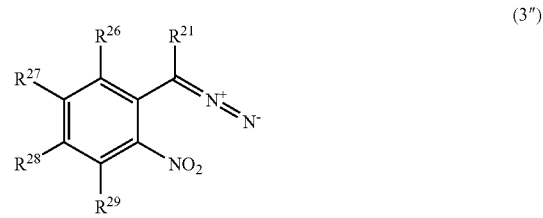

(3")

[In the general formula (3″), one of $R^{21}$ and $R^{26}$ to $R^{29}$ represents a binding hand to be bound to $A^1$ or $A^2$ of the general formula (1), and the other symbols represent as follows.

$R^{21}$ represents a hydrogen atom, —COOH, or a substituted or an unsubstituted functional group selected from an alkyl group having 1 to 20 carbon atoms, an alkenyl group having 2 to 20 carbon atoms, an alkynyl group having 2 to 20 carbon atoms, an alkoxy group having 1 to 20 carbon atoms, a thioalkoxy group having 1 to 20 carbon atoms, an alkylsulfonyl group having 1 to 20 carbon atoms, an arylsulfonyl group having 4 to 16 carbon atoms, a heteroalkyl group having a total number of carbon and hetero atoms of 2 to 20, a heteroalkenyl group having a total number of carbon and hetero atoms of 2 to 20, a cycloalkyl group having 3 to 8 carbon atoms, a cycloalkenyl group having 3 to 8 carbon atoms, an aryl group having 4 to 16 carbon atoms, a heteroaryl group having a total number of carbon and hetero atoms of 4 to 16, and a heterocyclyl group having a total number of carbon and hetero atoms of 2 to 30;

$R^{26}$ to $R^{29}$ each represent a hydrogen atom; $R^{27}$ and $R^{28}$, $R^{28}$ and $R^{29}$, or $R^{27}$ and $R^{26}$ may form in combination a group selected from an —O—$(CH_2)_n$—O— group, a —C—$(CH_2)_n$—O— group, an —O—$(CH_2)_n$—C— group, an —O—$(CH_2)_n$—N— group, a —N—$(CH_2)_n$—O— group, a —N—$(CH_2)_n$—N— group, a —C—$(CH_2)_n$—N— group, and a —N—$(CH_2)_n$—C— group. In this case, n is 1 or 2.)

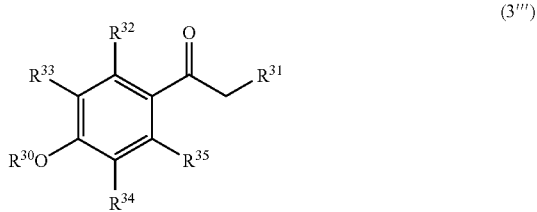

(3‴)

[In the general formula (3‴), one of $R^{30}$ and $R^{32}$ to $R^{35}$ represents a binding hand to be bound to $A^1$ or $A^2$ of the general formula (1), and the other symbols represent as follows.

$R^{30}$ represents a substituted or an unsubstituted functional group selected from an alkyl group having 1 to 20 carbon atoms, an alkenyl group having 2 to 20 carbon atoms, an alkynyl group having 2 to 20 carbon atoms, an alkoxy group having 1 to 20 carbon atoms, a thioalkoxy group having 1 to 20 carbon atoms, an alkylsulfonyl group having 1 to 20 carbon atoms, an arylsulfonyl group having 4 to 16 carbon atoms, a heteroalkyl group having a total number of carbon and hetero atoms of 2 to 20, a heteroalkenyl group having a total number of carbon and hetero atoms of 2 to 20, a cycloalkyl group having 3 to 8 carbon atoms, a cycloalkenyl group having 3 to 8 carbon atoms, an aryl group having 4 to 16 carbon atoms, a heteroaryl group having a total number of carbon and hetero atoms of 4 to 16, and a heterocyclyl group having a total number of carbon and hetero atoms of 2 to 30; $R^{31}$ represents a halogen atom; $R^{32}$ to $R^{35}$ each represent a hydrogen atom; $R^{33}$ and $R^{30}$ may form in combination a group selected from a —O—$(CH_2)_n$— group, a —C—$(CH_2)_n$— group, and an —N—$(CH_2)_n$— group; $R^{30}$ and $R^{34}$ may form in combination a group selected from a —$(CH_2)_n$—O— group, a —$(CH_2)_n$—C— group, and a —$(CH_2)_n$—N— group; $R^{32}$ and $R^{33}$ may form in combination a group selected from an —O—$(CH_2)_n$—O— group, a —C—$(CH_2)_n$—O— group, an —O—$(CH_2)_n$—C— group, an —O—$(CH_2)_n$—N— group, a —N—$(CH_2)_n$—O— group, a —N—$(CH_2)_n$—N— group, a —C—$(CH_2)_n$—N— group, and a —N—$(CH_2)_n$—C— group. In this case, n is 1 or 2.)

In the general formula (3), the alkoxy groups including the substituted or the unsubstituted alkoxy groups represented by A, $X^1$, and $X^2$ may be straight chained, branched, or cyclic, preferably straight chained, and includes an alkoxy group having 1 to 20 carbon atoms and preferably having 1 to 5 carbon atoms.

In particular, the alkoxy group is exemplified by for example, a methoxy group, an ethoxy group, a n-propoxy group, an isopropoxy group, a n-butoxy group, an isobutoxy group, a sec-butoxy group, a tert-butoxy group, a n-pentyloxy group, an isopentyloxy group, a sec-pentyloxy group, a tert-pentyloxy group, a neopentyloxy group, a 2-methylbutoxy group, a 1-ethylpropoxy group, a n-hexyloxy group, an isohexyloxy group, a sec-hexyloxy group, a tert-hexyloxy group, a neohexyloxy group, a 2-methylpentyloxy group, a 3-methylpentyloxy group, a 1,2-dimethylbutoxy group, a 2,2-dimethylbutoxy group, a 1-ethylbutoxy group, a 2-ethylbutoxy group, a n-heptyloxy group, an isoheptyloxy group, a sec-heptyloxy group, a tert-heptyloxy group, a neoheptyloxy group, a n-octyloxy group, an isooctyloxy group, a sec-octyloxy group, a tert-octyloxy group, a neooctyloxy group, a n-nonyloxy group, an isononyloxy group, a sec-nonyloxy group, a tert-nonyloxy group, a neononyloxy group, a n-decyloxy group, an isodecyloxy group, a sec-decyloxy group, a tert-decyloxy group, a neodecyloxy group, a n-undecyloxy group, an isoundecyloxy group, a sec-undecyoxy group, a tert-undecyloxy group, a neoundecyloxy group, a n-dodecyloxy group, an isododecyloxy group, a sec-dodecyloxy group, a tert-dodecyloxy group, a neododecyloxy group, a n-tridecyloxy group, an isotridecyloxy group, a sec-tridecyloxy group, a tert-tridecyloxy group, a neotridecyloxy group, a n-tetradecyloxy group, an isotetradecyloxy group, a sec-tetradecyloxy group, a tert-tetradecyloxy group, a neoteradecyloxy group, a n-pentadecyloxy group, an isopentadecyloxy group, a sec-pentadecyloxy group, a tert-pentadecyloxy group, a neopentadecyloxy group, a n-hexadecyloxy group, a sec-hexadecyloxy group, a tert-hexadecyloxy group, a neohexadecyloxy group, a n-heptadecyloxy group, an isoheptadecyloxy group, a sec-heptadecyloxy group, a tert-heptadecyloxy group, a neoheptadecyloxy group, a n-octadecyloxy group, an isooctadecyloxy group, a sec-octadecyloxy group, a tert-octadecyloxy group, a neooctadecyloxy group, a cyclopropyloxy group, a cyclobutyloxy group, a cyclopentyloxy group, a cyclohexyloxy group, a cycloheptyloxy group, a cyclooctyloxy group, a cyclononyloxy group, a cyclodecyloxy group, a cyclododecyloxy group, a cycloundecyloxy group, a cyclotridecyloxy group, a cyclotetradecyloxy group, a cyclopentadecyloxy group, a cyclohexadecyloxy group, a cycloheptadecyloxy group, and a cyclooctadecyloxy group.

In addition, the substituent includes, for example, a carboxyl group; a hydroxyl group; a sulfonic group; a lower alkyl group having 1 to 4 carbon atoms, such as a methyl group, an ethyl group, a n-propyl group, an isopropyl group, a n-butyl group, an isobutyl group, a sec-butyl group, or a tert-butyl group; a halogenated lower alkyl group having 1 to 4 carbon atoms, such as a fluoromethyl group, a difluoromethyl group, a trifluoromethyl group, a chloromethyl group, a dichloromethyl group, a trichloromethyl group, a bromomethyl group, a dibromomethyl group, a tribromomethyl group, an iodomethyl group, a diiodomethyl group, a triiodomethyl group, a trifluoroethyl group, a trichloroethyl group, a tribromoethyl group, a pentafluoroethyl group, a pentachloroethyl group, a pentabromoethyl group, heptafluoropropyl group, a heptachloropropyl group, a nonafluorobutyl group, a nonachlorobutyl group, a nonabromobutyl group, or a nonaiodobutyl group; or a lower alkoxy group having 1 to 4 carbon atoms, such as a methoxy group, an ethoxy group, a n-propoxy group, an isopropoxy group, a n-butoxy group, an isobutoxy group, a sec-butoxy group, or a tert-butoxy group.

The leaving group represented by Z of the general formula (3) is bound to a phosphoric group, a carboxyl group, a hydroxyl group, an amino group, or the like and is changed into a group which can be eliminated by photodegradation (a group capable of forming a group that causes a deprotection reaction by light irradiation).

In general, the leaving group is a group that is to be eliminated from a substrate (a compound to which the leaving group is bound) together with an electron pair of a covalent bond between the leaving group and the substrate (the compound to which the leaving group is bound). As a preferable leaving group, for example, a group may be exemplified in which an electron pair can be stabilized by electron-withdrawing properties, aromatic properties, a resonant structure, or combinations therebetween, and the leaving group includes for example, a group bound with a halogenated compound, a carboxylate, a carbonate, an amide, a carbamate, a phospholate, a sulfonate, an amino, an aryloxide, a thiolate group, or the like.

As the leaving group represented by Z, in more particular, for example, a halogen atom, an alkoxy group, an aryloxy group, a substituted aryloxy group, —$NR^{15}R^{16}$, —$OC(O)R^{14}$, —$OP(O)R^{15}R^{16}$, —$OP(O)(OH)R^{15}$, —$OC(O)NR^{15}R^{16}$, —$NR^{15}C(O)OR^{16}$, —$SR^{14}$, —$NR^{15}C(O)R^{16}$, —$O_3SR^{14}$, or —O—$NN(O)(NR^{15}R^{16})$ is specifically exemplified.

In this case, $R^{14}$, $R^{15}$, and $R^{16}$ each independently represent a substituted or an unsubstituted functional group selected from an alkyl group having 1 to 20 carbon atoms, an alkenyl group having 2 to 20 carbon atoms, an alkynyl group having 2 to 20 carbon atoms, an alkoxy group having 1 to 20 carbon atoms, a thioalkoxy group having 1 to 20 carbon atoms, an alkylsulfonyl group having 1 to 20 carbon atoms, an arylsulfonyl group having 4 to 16 carbon atoms, a heteroalkyl group having 2 to 20 carbon atoms, a heteroalkenyl group having 2 to 20 carbon atoms, a cycloalkyl group having 3 to 8 carbon atoms, a cycloalkenyl group having 3 to 8 carbon atoms, an aryl group having 4 to 16 carbon atoms, a heteroaryl group having 4 to 16 carbon atoms, and a heterocyclyl group having 2 to 30 carbon atoms, and $R^{15}$ and $R^{16}$ may form in combination an alkylene group having 1 to 20 carbon atoms.

The halogen atom represented by Z includes F, Cl, Br, or I.

In addition, the alkoxy group may be straight chained, branched, or cyclic, preferably straight chained, and includes an alkoxy group having 1 to 20 carbon atoms, preferably an alkoxy group having 1 to 5 carbon atoms.

In particular, the alkoxy group includes, for example, a methoxy group, an ethoxy group, a n-propoxy group, an isopropoxy group, a n-butoxy group, an isobutoxy group, a sec-butoxy group, a tert-butoxy group, a n-pentyloxy group, an isopentyloxy group, a sec-pentyloxy group, a tert-pentyloxy group, a neopentyloxy group, a 2-methylbutoxy group, a 1-ethylpropoxy group, a n-hexyloxy group, an isohexyloxy group, a sec-hexyloxy group, a tert-hexyloxy group, a neohexyloxy group, a 2-methylpentyloxy group, a 3-methylpentyloxy group, a 1,2-dimethylbutoxy group, a 2,2-dimethylbutoxy group, a 1-ethylbutoxy group, a 2-ethylbutoxy group, a n-heptyloxy group, an isoheptyloxy group, a sec-heptyloxy group, a tert-heptyloxy group, a neoheptyloxy group, a n-octyloxy group, an isooctyloxy group, a sec-octyloxy group, a tert-octyloxy group, a neooctyloxy group, a n-nonyloxy group, an isononyloxy group, a sec-nonyloxy group, a tert-nonyloxy group, a neononyloxy group, a n-decyloxy group, an isodecyloxy group, a sec-decyloxy group, a tert-decyloxy group, a neodecyloxy group, a n-undecyloxy group, an isoundecyloxy group, a sec-undecyoxy group, a tert-undecyloxy group, a neoundecyloxy group, a n-dodecyloxy group, an isododecyloxy group, a sec-dodecyloxy group, a tert-dodecyloxy group, a neododecyloxy group, a n-tridecyloxy group, an isotridecyloxy group, a sec-tridecyloxy group, a tert-tridecyloxy group, a neotridecyloxy group, a n-tetradecyloxy group, an isotetradecyloxy group, a sec-tetradecyloxy group, a tert-tetradecyloxy group, a neoteradecyloxy group, a n-pentadecyloxy group, an isopentadecyloxy group, a sec-pentadecyloxy group, a tert-pentadecyloxy group, a neopentadecyloxy group, a n-hexadecyloxy group, a sec-hexadecyloxy group, a tert-hexadecyloxy group, a neohexadecyloxy group, a n-heptadecyloxy group, an isoheptadecyloxy group, a sec-heptadecyloxy group, a tert-heptadecyloxy group, a neoheptadecyloxy group, a n-octadecyloxy group, an isooctadecyloxy group, a sec-octadecyloxy group, a tert-octadecyloxy group, a neooctadecyloxy group, a cyclopropyloxy group, a cyclobutyloxy group, a cyclopentyloxy group, a cyclohexyloxy group, a cycloheptyloxy group, a cyclooctyloxy group, a cyclononyloxy group, a cyclodecyloxy group, a cyclododecyloxy group, a cycloundecyloxy group, a cyclotridecyloxy group, a cyclotetradecyloxy group, a cyclopentadecyloxy group, a cyclohexadecyloxy group, a cycloheptadecyloxy group, and a cyclooctadecyloxy group.

As the aryloxy group, and an aryloxy group of the substituted aryloxy group represented by Z are included, for example, an aromatic monocyclic or condensed polycyclic group having 4 to 16 carbon atoms, preferably 5 to 14 carbon atoms, and in particular, the aryloxy group is exemplified by, for example, a phenyloxy group, a tolyloxy group, a xylyloxy group, a mesityloxy group, a naphtyloxy group, an anthryloxy group, and a phenanthryloxy group.

In addition, the substituent of the substituted aryloxy group includes, for example, a halogen atom (F, Cl, Br, or I), a nitro group, and perfluoroalkyl group having 1 to 3 carbon atoms (a trifluoromethyl group, a pentafluoroethyl group, or heptafluoropropyl group).

The alkyl group having 1 to 20 carbon atoms represented by $R^{11}$ to $R^{16}$ of the general formula (3), the alkyl group having 1 to 20 carbon atoms represented by $R^{21}$ to $R^{23}$ of the general formula (3'), the alkyl group having 1 to 20 carbon atoms represented by $R^{21}$ of the general formula (3"), and the alkyl group having 1 to 20 carbon atoms represented by $R^{30}$ of the general formula (3''') may be straight chained or branched, preferably a straight chained, and include, for example, preferably a group having 1 to 5 carbon atoms.

In particular, the alkyl group is exemplified by, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a sec-hexyl group, a tert-hexyl group, a neohexyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a n-nonyl group, an isononyl group, a sec-nonyl group, a tert-nonyl group, a neononyl group, a n-decyl group, an isodecyl group, a sec-decyl group, a tert-decyl group, a neodecyl group, a n-undecyl group, an isoundecyl group, a sec-undecyl group, a tert-undecyl group, a neoundecyl group, a n-dodecyl group, an isododecyl group, a sec-dodecyl group, a tert-dodecyl group, a neododecyl group, a n-tridecyl group, an isotridecyl group, a sec-tridecyl group, a tert-tridecyl group, a neotridecyl group, a n-tetradecyl group, an isotetradecyl group, a sec-tetradecyl group, a tert-tetradecyl group, a neotetradecyl group, a n-pentadecyl group, an isopentadecyl group, a sec-pentadecyl group, a tert-pentadecyl group, a neopentadecyl group, a n-hexadecyl group, an isohexadecyl group, a sec-hexadecyl group, a tert-hexadecyl group, a neohexadecyl group, a n-heptadecyl group, an isoheptadecyl group, a sec-heptadecyl group, a tert-heptadecyl group, a neoheptadecyl group, a n-octadecyl group, an isooctadecyl group, a sec-octadecyl group, a tert-octadecyl group, a neooctadecyl group, a n-nonadecyl group, an isononadecyl group, a sec-nonadecyl group, a tert-nonadecyl group, a neononadecyl group, a n-icosyl group, an isoicosyl group, a sec-icosyl group, a tert-icosyl group, and a neoicosyl group.

The alkenyl group having 2 to 20 carbon atoms represented by $R^{11}$ to $R^{16}$ of the general formula (3), the alkenyl group having 2 to 20 carbon atoms represented by $R^{21}$ to $R^{23}$ of the general formula (3'), the alkenyl group having 2 to 20 carbon atoms represented by $R^{21}$ of the general formula (3''), and the alkenyl group having 2 to 20 carbon atoms represented by $R^{30}$ of the general formula (3''') are a hydrocarbon group having at least one double bond, which may be straight chained or branched, preferably straight chained, and include preferably a group having 2 to 5 carbon atoms.

In particular, the alkenyl group is exemplified by, for example, ethenyl, 1-propenyl, 2-propenyl, 1-methyl-2-propenyl, 1-methyl-1-propenyl, 2-methyl-1-propenyl, 2-methyl-2-propenyl, 2-ethyl-2-propenyl, 1-butenyl, 2-butenyl, 1-methyl-2-butenyl, 1-methyl-1-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 1-hexenyl, 2-hexenyl, 3-hexenyl, 4-hexenyl, 5-hexenyl, heptenyl, octenyl, decenyl, dodecenyl, tetradecenyl, hexadecenyl, heptadecenyl, heptadecadienyl, heptadecatrienyl, octadecenyl, nonadecenyl, and eicocenyl.

The alkynyl group having 2 to 20 carbon atoms represented by $R^{11}$ to $R^{16}$ of the general formula (3), the alkynyl group having 2 to 20 carbon atoms represented by $R^{21}$ to $R^{23}$ of the general formula (3'), the alkynyl group having 2 to 20 carbon atoms represented by $R^{21}$ of the general formula (3''), and the alkynyl group having 2 to 20 carbon atoms represented by $R^{30}$ of the general formula (3''') are an aliphatic hydrocarbon group having at least one triple bond, which may be straight chained, branched, or cyclic, preferably straight chained, and include preferably a group having 2 to 5 carbon atoms.

In particular, the alkynyl group is exemplified by, for example, there may be mentioned an ethynyl group, 1-propynyl, a 2-propynyl group, propalgyl, a 1-butynyl group, a 2-butynyl group, a pentynyl group, a hexynyl group, an octynyl group, a 2-ethylhexynyl group, a decynyl group, a dodecynyl group, and octadecynyl group.

The alkoxy group having 1 to 20 carbon atoms represented by $R^{11}$ to $R^{16}$ of the general formula (3), the alkoxy group having 1 to 20 carbon atoms represented by $R^{21}$ to $R^{23}$ of the general formula (3'), the alkoxy group having 1 to 20 carbon atoms represented by $R^{21}$ of the general formula (3''), and the alkoxy group having 1 to 20 carbon atoms represented by $R^{30}$ of the general formula (3''') may be straight chained, branched, or cyclic, preferably straight chained, and include preferably a group having 2 to 5 carbon atoms.

In particular, the alkoxy group is exemplified by, for example, a methoxy group, an ethoxy group, a n-propoxy group, an isopropoxy group, a n-butoxy group, an isobutoxy group, a sec-butoxy group, a tert-butoxy group, a n-pentyloxy group, an isopentyloxy group, a sec-pentyloxy group, a tert-pentyloxy group, a neopentyloxy group, a 2-methylbutoxy group, a 1-ethylpropoxy group, a n-hexyloxy group, an isohexyloxy group, a sec-hexyloxy group, a tert-hexyloxy group, a neohexyloxy group, a 2-methylpentyloxy group, a 3-methylpentyloxy group, a 1,2-dimethylbutoxy group, a 2,2-dimethylbutoxy group, a 1-ethylbutoxy group, a 2-ethylbutoxy group, a n-heptyloxy group, an isoheptyloxy group, a sec-heptyloxy group, a tert-heptyloxy group, a neoheptyloxy group, a n-octyloxy group, an isooctyloxy group, a sec-octyloxy group, a tert-octyloxy group, a neooctyloxy group, a n-nonyloxy group, an isononyloxy group, a sec-nonyloxy group, a tert-nonyloxy group, a neononyloxy group, a n-decyloxy group, an isodecyloxy group, a sec-decyloxy group, a tert-decyloxy group, a neodecyloxy group, a n-undecyloxy group, an isoundecyloxy group, a sec-undecyoxy group, a tert-undecyloxy group, a neoundecyloxy group, a n-dodecyloxy group, an isododecyloxy group, a sec-dodecyloxy group, a tert-dodecyloxy group, a neododecyloxy group, a n-tridecyloxy group, an isotridecyloxy group, a sec-tridecyloxy group, a tert-tridecyloxy group, a neotridecyloxy group, a n-tetradecyloxy group, an isotetradecyloxy group, a sec-tetradecyloxy group, a tert-tetradecyloxy group, a neoteradecyloxy group, a n-pentadecyloxy group, an isopentadecyloxy group, a sec-pentadecyloxy group, a tert-pentadecyloxy group, a neopentadecyloxy group, a n-hexadecyloxy group, a sec-hexadecyloxy group, a tert-hexadecyloxy group, a neohexadecyloxy group, a n-heptadecyloxy group, an isoheptadecyloxy group, a sec-heptadecyloxy group, a tert-heptadecyloxy group, a neoheptadecyloxy group, a n-octadecyloxy group, an isooctadecyloxy group, a sec-octadecyloxy group, a tert-octadecyloxy group, a neooctadecyloxy group, a cyclopropyloxy group, a cyclobutyloxy group, a cyclopentyloxy group, a cyclohexyloxy group, a cycloheptyloxy group, a cyclooctyloxy group, a cyclononyloxy group, a cyclodecyloxy group, a cyclododecyloxy group, a cycloundecyloxy group, a cyclotridecyloxy group, a cyclotetradecyloxy group, a cyclopentadecyloxy group, a cyclohexadecyloxy group, a cycloheptadecyloxy group, and a cyclooctadecyloxy group.

The thioalkoxy group having 1 to 20 carbon atoms represented by $R^{11}$ to $R^{16}$ of the general formula (3), the thioalkoxy group having 1 to 20 carbon atoms represented by $R^{21}$ to $R^{23}$ of the general formula (3'), the thioalkoxy group having 1 to 20 carbon atoms represented by $R^{21}$ of the general formula (3''), and the thioalkoxy group having 1 to 20 carbon atoms represented by $R^{30}$ of the general formula (3''') may be straight chained, branched, or cyclic, preferably straight chained group, and include preferably a group having 2 to 5 carbon atoms.

In particular, the thioalkoxy group is exemplified by, for example, a thiomethoxy group, a thioethoxy group, a thiopropoxy group, a thiobutoxy group, a thiopentyloxy group, a thiomethylbutoxy group, a thioethylpropoxy group, a thiohexyloxy group, a thiomethylpentyloxy group, a thiodimethylbutoxy group, a thioethylbutoxy group, a thioheptyloxy group, a thiooctyloxy group, a thiononyloxy group, a thiodecyloxy group, a thioundecyloxy group, a thiododecyloxy group, a thiotridecyloxy group, a thiotetradecyloxy group, a thiopentadecyloxy group, a thiohexadecyloxy group, a thioheptadecyloxy group, a thiooctadecyloxy group, a thiocyclopropyloxy group, a thiocyclobutyloxy group, a thiocyclopentyloxy group, a thiocyclohexyloxy group, a thiocycloheptyloxy group, a thiocyclooctyloxy group, a thiocyclononyloxy group, a thiocyclodecyloxy group, a thiocyclododecyloxy group, a thiocycloundecyloxy group, a thiocyclotridecyloxy group, a thiocyclotetradecyloxy group, a thiocyclopentadecyloxy group, a thiocyclohexadecyloxy group, a thiocycloheptadecyloxy group, and a thiocyclooctadecyloxy group.

The alkylsulfonyl group having 1 to 20 carbon atoms represented by $R^{11}$ to $R^{16}$ of the general formula (3), the alkylsulfonyl group having 1 to 20 carbon atoms represented by $R^{21}$ to $R^{23}$ of the general formula (3'), the alkylsulfonyl group having 1 to 20 carbon atoms represented by $R^{21}$ of the general formula (3''), and the alkylsulfonyl group having 1 to 20 carbon atoms represented by $R^{30}$ of the general formula (3''') may be straight chained, branched, or cyclic, preferably straight chained group, and include preferably a group having 2 to 5 carbon atoms.

In particular, the alkylsulfonyl group is exemplified by, for example, a methylsulfonyl group, an ethylsulfonyl group, a propylsulfonyl group, a butylsulfonyl group, a pentylsulfonic group, a hexylsulfonyl group, a heptylsulfonyl group, an octylsulfonyl group, a nonylsulfonyl group, a decylsulfonyl group, a undecylsulfonyl group, a dodecylsulfonyl group, a tridecylsulfonyl group, a tetradecylsulfonyl group, a pentadecylsulfonyl group, a hexadecylsulfonyl group, a heptadecylsulfonyl group, an octadecylsulfonyl group, a nonadecylsulfonyl group, and an eicosylsulfonyl group.

The arylsulfonyl group having 4 to 16 carbon atoms represented by $R^{11}$ to $R^{16}$ of the general formula (3), the arylsulfonyl group having 4 to 16 carbon atoms represented by $R^{21}$ to $R^{23}$ of the general formula (3'), the arylsulfonyl group having 4 to 16 carbon atoms represented by $R^{21}$ of the general formula (3''), and the a arylsulfonyl group having 4 to 16 carbon atoms represented by $R^{30}$ of the general formula (3''') may be monocyclic or condensed polycyclic, and include preferably a group having 5 to 14 carbon atoms.

In particular, the arylsulfonyl group is exemplified by, for example, a phenylsulfonyl group, a tolylsulfonyl group, a xylylsulfonyl group, a mesitylsulfonyl group, a naphtylsulfonyl group, an anthrylsulfonyl group, and a phenanthrylsulfonyl group.

The heteroalkyl group having a total number of carbon and hetero atoms of 2 to 20 represented by $R^{11}$ to $R^{16}$ of the general formula (3), the heteroalkyl group having a total number of carbon and hetero atoms of 2 to 20 represented by $R^{21}$ to $R^{23}$ of the general formula (3'), the heteroalkyl group having a total number of carbon and hetero atoms of 2 to 20 represented by $R^{21}$ of the general formula (3''), and the heteroalkyl group having a total number of carbon and hetero atoms of 2 to 20 represented by $R^{30}$ of the general formula (3''') are the alkyl groups described above or cyclically groups described later, each of which includes at least one hetero atom selected from O, S, N, and P in the main-chain moiety, and may be straight chained, branched, or cyclic. A group having a total number of carbon and hetero atoms of 2 to 10 is preferably included, and the number of included hetero atoms is 1 to 5.

The heteroalkenyl group having a total number of carbon and hetero atoms of 2 to 20 represented by $R^{11}$ to $R^{16}$ of the general formula (3), the heteroalkenyl group having a total number of carbon and hetero atoms of 2 to 20 represented by $R^{21}$ to $R^{23}$ of the general formula (3'), the heteroalkenyl group having a total number of carbon and hetero atoms of 2 to 20 represented by $R^{21}$ of the general formula (3''), and the heteroalkenyl group having a total number of carbon and hetero atoms of 2 to 20 represented by $R^{30}$ of the general formula (3''') are the alkenyl groups described above or cycloalkenyl groups described later, each of which includes at least one hetero atom selected from O, S, N, and P in the main-chain moiety, and may be straight chained, branched, or cyclic. A group having a total number of carbon and hetero atoms of 2 to 10 is preferably included, and the number of included hetero atoms is 1 to 5.

As the cycloalkyl group having 3 to 8 carbon atoms represented by $R^{11}$ to $R^{16}$ of the general formula (3), the cycloalkyl group having 3 to 8 carbon atoms represented by $R^{21}$ to $R^{23}$ of the general formula (3'), the cycloalkyl group having 3 to 8 carbon atoms represented by $R^{21}$ of the general formula (3''), and the cycloalkyl group having 3 to 8 carbon atoms represented by $R^{30}$ of the general formula (3'''), a group having 5 to 14 carbon atoms is preferably included.

In particular, the cycloalkyl group is exemplified by, for example, a cyclopropyl group, a cyclobutyl group, a cyclopentyl group, cyclohexyl group, a cycloheptyl group, and cyclooctyl group.

The cycloalkenyl group having 3 to 8 carbon atoms represented by $R^{11}$ to $R^{16}$ of the general formula (3), the cycloalkenyl group having 3 to 8 carbon atoms represented by $R^{21}$ to $R^{23}$ of the general formula (3'), the cycloalkenyl group having 3 to 8 carbon atoms represented by $R^{21}$ of the general formula (3''), and the cycloalkenyl group having 3 to 8 carbon atoms represented by $R^{30}$ of the general formula (3''') are each a cycloalkyl group including a double bond, and a group having 5 to 14 carbon atoms is preferably included.

In particular, the cycloalkenyl group is exemplified by, for example, a cyclopentenyl group, a methylcyclopentenyl group, a cyclohexenyl group, a methylcyclohexyl group, a dimethylcyclohexyl group, a ethylcyclohexyl group, a butylcyclohexyl group, a cycloheptenyl group, cyclooctenyl group, a cyclodecenyl group, and a cyclododecenyl group.

The aryl group having 4 to 16 carbon atoms represented by $R^{11}$ to $R^{16}$ of the general formula (3), the aryl group having 4 to 16 carbon atoms represented by $R^{21}$ to $R^{23}$ of the general formula (3'), the aryl group having 4 to 16 carbon atoms represented by $R^{21}$ of the general formula (3''), and the aryl group having 4 to 16 carbon atoms represented by $R^{30}$ of the general formula (3''') are each an aromatic monocyclic or condensed polycyclic group, and a group having to 14 carbon atoms is preferably included.

In particular, the aryl group is exemplified by, for example, a phenyl group, an o-tolyl group, a m-tolyl group, a p-tolyl, a 2,3-xylyl group, a 2,4-xylyl group, a 2,5-xylyl group, a 2,6-xylyl group, a 3,5-xylyl group, a mesityl group, a naphtyl group, an anthryl group, and a phenanthryl group.

The heteroaryl group having a total number of carbon and hetero atoms of 4 to 16 represented by $R^{11}$ to $R^{16}$ of the general formula (3), the heteroaryl aryl group having a total number of carbon and hetero atoms of 4 to 16 represented by $R^{21}$ to $R^{23}$ of the general formula (3'), the heteroaryl group having a total number of carbon and hetero atoms of 4 to 16 represented by $R^{21}$ of the general formula (3''), and the heteroaryl group having a total number of carbon and hetero atoms of 4 to 16 represented by $R^{30}$ of the general formula (3''') are each the aforementioned aryl group including at least one hetero atom selected from O, S, N, and P in the ring and may be a monocyclic or a condensed polycyclic group, and a group having a total number of carbon and hetero atoms of 5 to 14 is preferably included. In addition, the number of included hetero atoms is 1 to 5.

In particular, the heteroaryl aryl group is exemplified by, for example, monocyclic groups, such as a furyl group, a thienyl group, a pyrrolyl group, an azepinyl group, a pyrazolyl group, an imidazolyl group, an oxazolyl group, an isoxazolyl group, a thiazolyl group, an isothiazolyl group, a 1,2, 3-oxadiazolyl group, a triazolyl group, a tetrazolyl group, a thiadiazolyl group, a pyranyl group, a pyridyl group, a pyridazinyl group, a pyrimidinyl group, a pyrazinyl group, a morpholinyl group, a thiomorpholinyl group, a pyrrolidinyl group, a pyrrolinyl group, an imidazolidinyl group, an imidazolinyl group, a pyrazolidinyl group, a pyrazolinyl group, a piperidyl group, and a piperazinyl group; and groups formed by ring condensation between the above monocyclic groups and other cyclic groups, such as a cinnolinyl group, a benzofuranyl group, an isobenzofuranyl group, a chromenyl group, a xanthenyl group, a phenoxanthinyl group, an indolizinyl group, an isoindolyl group, an indolyl group, an indazolyl group, a purinyl group, a quinolizinyl group, an isoquinolyl group, a quinolyl group, a phthalazinyl group, a naphthyridinyl group, a quinoxalinyl group, a quinazolinyl group, a carbazolyl group, a carbolinyl group, an acridinyl group, an isoindolynyl group, a benzoxazolyl group (benzoxazole-2-yl group), a benzothiazolyl group (benzothiazole-2-yl group), a benzimidazolyl group (benzoimidazole-2-yl), and a pteridinyl group.

The heterocyclic group having a total number of carbon and hetero atoms of 2 to 30 represented by $R^{11}$ to $R^{16}$ of the general formula (3), the heterocyclic group having a total number of carbon and hetero atoms of 2 to 30 represented by $R^{21}$ to $R^{23}$ of the general formula (3'), the heterocyclic group having a total number of carbon and hetero atoms of 2 to 30 represented by $R^{21}$ of the general formula (3"), and the heterocyclic group having a total number of carbon and hetero atoms of 2 to 30 represented by $R^{30}$ of the general formula (3''') are each a saturated, a partially unsaturated, or an aromatic 5- to 10-member heterocyclic group which includes at least one hetero atom selected from O, S, N, and P, and may be a monocyclic or a condensed polycyclic group, and a group having a total number of carbon and hetero atoms of 5 to 14 carbon atoms is preferably included.

In particular, the heterocyclic group is exemplified by, for example, monocyclic groups, such as a furyl group, a thienyl group, a pyrrolyl group, an azepinyl group, a pyrazolyl group, an imidazolyl group, an oxazolyl group, an isoxazolyl group, a thiazolyl group, an isothiazolyl group, a 1,2,3-oxadiazolyl group, a triazolyl group, a tetrazolyl group, a thiadiazolyl group, a pyranyl group, a pyridyl group, a pyridazinyl group, a pyrimidinyl group, a pyrazinyl group, a morpholinyl group, a thiomorpholinyl group, a pyrrolidinyl group, a pyrrolinyl group, an imidazolidinyl group, an imidazolinyl group, a pyrazolidinyl group, a pyrazolinyl group, a piperidyl group, and a piperazinyl group; and groups formed by ring condensation between the above monocyclic groups and other cyclic groups, such as a cinnolinyl group, a benzofuranyl group, an isobenzofuranyl group, a chromenyl group, a xanthenyl group, a phenoxanthinyl group, an indolizinyl group, an isoindolyl group, an indolyl group, an indazolyl group, a purinyl group, a quinolizinyl group, an isoquinolyl group, a quinolyl group, a phthalazinyl group, a naphthyridinyl group, a quinoxalinyl group, a quinazolinyl group, a carbazolyl group, a carbolinyl group, an acridinyl group, an isoindolynyl group, a benzoxazolyl group (benzoxazole-2-yl group), a benzothiazolyl group (benzothiazole-2-yl group), a benzimidazolyl group (benzoimidazole-2-yl), and a pteridinyl group.

The alkylene group having 1 to 20 carbon atoms of the general formula (3), which is formed in combination from $R^{15}$ and $R^{16}$, may be straight chained, branched, or cyclic, and a group having 1 to 3 carbon atoms is preferably included.

In particular, the alkylene group is exemplified by, for example, a methylene group, an ethylene group, a methylmethylene group, an ethylmethylene group, a trimethylene group, a propylene group, a 2-propylene group, a propylmethylene group, an ispropylmethylene group, a dimethylmethylene group, a tetramethylene group, a butylene group, a 2-methylpropylene group, a pentamethylene group, a pentylene group, a 1-methyltrimethylene group, a 2-methyltrimethylene group, a 3-methyltrimethylene group, a 1-ethylethylene group, a 2-ethylethylene group, an ethylmethylethylene group, a 1-methyltetramethylene group, a 2-methyltetramethylene group, a 3-methyltetramethylene group, a 4-methyltetramethylene group, a 1,1-dimethyltrimethylene group, a 1,2-dimethyltrimethylene group, a 1,3-dimethyltrimethylene group, a 2,2-dimethyltrimethylene group, a 2-ethyltrimethylene group, a hexamethylene group, a hexylene group, a 1-ethyltrimethylene group, a undecamethylene group, a 1-methyldecamethylene group, a 1-methylpentamethylene group, a 2-methylpentamethylene group, a 3-methylpentamethylene group, a 1,2-dimethyltetramethylene group, 1,3-dimethyltetramethylene group, a 2,3-dimethyltetramethylene group, a 1,1-dimethyltetramethylene group, a 1-ethyltetramethylene group, a 2-ethyltetramethylene group, a 1-ethyl-2-methyltrimethylene group, a 1-methylhexamethylene group, a 1-methylheptamethylene group, a 1-methyloctamethylene group, a 1-methylnonamethylene group, a heptamethylene group, a heptylene group, an octamethylene group, an octylene group, a 2-ethylhexylene group, a nonamethylene group, a nonylene group, a decamethylene group, a decylene group, hendecamethylene group, a dodecamethylene group, a tridecamethylene group, a tetradecamethylene group, a pentadecamethylene group, a hexadecamethylene group, an heptadecamethylene group, an octadecamethylene group, a nonadecamethylene group, an eicosamethylene group, a cyclopropylene group, a cyclopentylene group, a cyclohexylene group, a cycloheptylene group, a cyclooctylene group, a cyclononylene group, and a cyclodecylene group. Among those mentioned above, an ethylene group is preferable.

The halogen atom represented by $R^{31}$ of the general formula (3''') includes F, Cl, Br, or I.

In the present invention, among the photodegradable protective groups as described above, the group represented by the general formula (3) is preferable, and in particular, the groups represented by the following general formulas (4) and (5) are more preferable.

$Q^1$ and $Q^2$, which are the photodegradable protective groups, may be the same or different from each other.

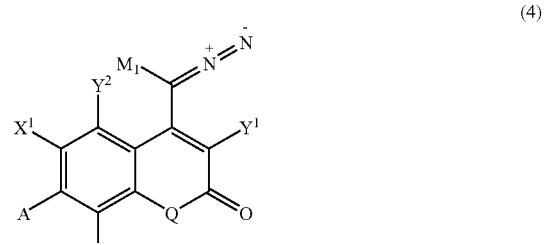

(4)

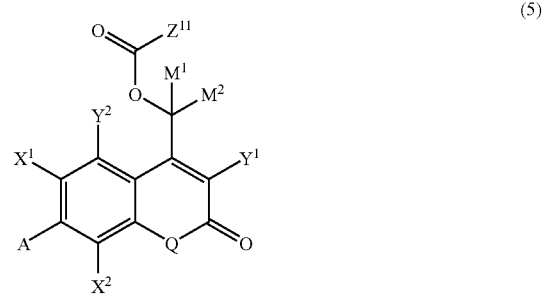

(5)

[In the formula, $Z^{11}$ represents a halogen atom, an imidazolyl group, or a 4-nitrophenoxy group, and Q, A, $Y^1$, $Y^2$, $M^1$, $M^2$, $X^1$, and $X^2$ are the same as described above.]

The halogen atom represented by Z of the general formula (5) includes F, Cl, Br, or I.

As the compound of the general formulas (3), (4), and (5), it is preferable that one of $Y^1$, $Y^2$, $X^1$, $X^2$, A and $M^1$ be a binding hand to be bound to $A^1$ and/or $A^2$ of the general formula (1), Q be —O—, A be a hydroxyl group, —$OCH_3$, or —$OC_2H_5$, $X^2$ be —H, $Y^1$ be —H, $Y^2$ be —H, $X^1$ be —Br, Z be —OC(O)-(4-nitrophenyl), —OC(O)O-(4-nitrophenyl), —$NR^{15}C(O)R^{16}$, —$OC(O)NR^{15}R^{16}$, —$OP(O)R^{15}R^{16}$, or —$OC(O)Z^{11}$, to be =$N_2$ together with $M^2$. It is particularly preferable that Q be —O—, A be a binding hand to be bound to $A^1$ and/or $A^2$ of the general formula (1), $X^2$ be —H, $Y^1$ be —H, $Y^2$ be —H, $X^1$ be —Br, Z be —OC(O)-(4-nitrophenyl), —OC(O)O-(4-nitrophenyl), —$NR^{15}C(O)R^{16}$, —$OC(O)NR^{15}R^{16}$, —$OP(O)R^{15}R^{16}$, or —$OC(O)Z^{11}$, or be =$N_2$ together with $M^2$.

The photodegradable protective group of the present invention described above can be appropriately synthesized, for example, in accordance with the description of International Publication Pamphlet WO00/31588, Japanese Unexamined Patent Application Publication No. 2002-315576, T. Furuta, et al., Proc. Natl. Acad. Sci., USA., vol. 96, pp. 1193-1200, February 1999, Chemistry, Neurobiology, R. S. Givens, C. H. Park, Tetrahedron Lett. 37, 6259-6262 (1996), C. H. Park, R. S. Givens, J. Am. Chem. Soc., 119, 2453-2463 (1997), J. Engels, E. J. Schlaeger, J. Med. Chem. 20, 907 (1977), and J. H. Kaplan, G. Forbush III, J. F. Hoffman, Biochemistry 17, 1920-1935 (1978), and in addition, a commercially available compound may also be used. In particular, the compounds of the above general formulas (3), (4), and (5) can be synthesized in accordance the methods described in International Publication Pamphlet WO00/31588, Japanese Unexamined Patent Application Publication No. 2002-315576, T. Furuta, et al., Proc. Natl. Acad. Sci., USA., vol. 96, pp. 1193-1200, February 1999, Chemistry, Neurobiology, and the like.

1-2. Linker Portion

In the general formula (1), the structural portion represented by -$A^1$-$T^1$-$A^2$- is a linker portion to bind the photodegradable protective groups represented by $Q^1$ and $Q^2$.

That is, $A^1$ of the linker portion is bound to the photodegradable protective group $Q^1$ as described above, and $A^2$ is bound to the photodegradable protective group $Q^2$ as described above, so that a compound is formed in which the two photodegradable protective groups $Q^1$ and $Q^2$ are bound to each other with $T^1$ provided therebetween.

In more particular, for example, when the photodegradable protective group is represented by the general formula (3), one of $Y^1$, $Y^2$, $X^1$, $X^2$, A, and $M^1$ of the general formula (3) is a binding hand, and $A^1$ and/or $A^2$ of the linker are bound thereto. It is preferable that A of the general formula (3) is a binding hand, and that $A^1$ and/or $A^2$ of the linker portion be bound to the position of A.

When the photodegradable protective group is represented by the general formula (3'), one of $R^{21}$, $R^{22}$, $R^{23}$, $R^{24}$, and $R^{25}$ of the general formula (3') is a binding hand, and $A^1$ and/or $A^2$ of the linker portion are bound thereto. It is preferable that $R^{23}$ of the general formula (3') is a binding hand, and that $A^1$ and/or $A^2$ of the linker portion be bound to the position of $R^{23}$.

When the photodegradable protective group is represented by the general formula (3"), one of $R^{21}$, $R^{26}$, $R^{27}$, $R^{28}$, and $R^{29}$ of the general formula (3") is a binding hand, and $A^1$ and/or $A^2$ of the linker portion are bound thereto. It is preferable that $R^{28}$ of the general formula (3") is a binding hand, and that $A^1$ and/or $A^2$ of the linker portion be bound to the position of $R^{28}$.

When the photodegradable protective group is represented by the general formula (3'''), one of $R^{30}$, $R^{32}$, $R^{33}$, $R^{34}$, and $R^{35}$ of the general formula (3''') is a binding hand, and $A^1$ and/or $A^2$ of the linker are bound thereto. It is preferable that $R^{30}$ of the general formula (3''') is a binding hand, and that $A^1$ and/or $A^2$ of the linker portion be bound to the position of $R^{30}$.

It is preferable that the length of the linker be sufficient so that $Q^1$ and $Q^2$ bound to the two ends bind nucleic acids, a nucleic acid and a protein or a polypeptide, or proteins or polypeptides, that is, the linker preferably has a length which can crosslink a sense chain and an antisense chain of a double-stranded nucleic acid, a nucleic acid and a protein or a polypeptide, or two proteins or two polypeptides (between proteins, between a protein and a polypeptide, or between polypeptides). In particular, the linker preferably has a length sufficient so as to bind a sense chain and an antisense chain of a double-stranded RNA.

In more particular, since the distance between materials to be crosslinked varies depending on types thereof, a preferable length of the linker portion cannot be simply determined; however, the lower limit of the length of the linker portion is generally 2 Å or more and preferably 9 Å or more, and the upper limit is generally 94 Å or less and preferably 74 Å or less.

For example, when nucleic acids (a double-stranded DNA, a double-stranded RNA, or a double-stranded hybrid composed of DNA and RNA) are crosslinked, the lower limit of the length of the linker portion is generally 2 Å or more, preferably 9 Å or more, and more preferably 19 Å or more, and the upper limit is generally 44 Å or less and preferably 29 Å or less.

When a nucleic acid and a protein or a polypeptide are crosslinked, or two proteins or two polypeptides are crosslinked, the lower limit of the length of the linker portion is generally 4 Å or more and preferably 19 Å or more, and the upper limit is generally 94 Å or less and preferably 74 Å or less.

The alkylene groups represented by $A^1$, $A^2$, and $T^1$ may be straight chained, branched, or cyclic, and includes a group generally having 1 to 10 carbon atoms, preferably 1 to 8 carbon atoms.

In particular, the alkylene group is exemplified by, for example, a methylene group, an ethylene group, a methylmethylene group, an ethylethylene group, a trimethylene group, a propylene group, a tetramethylene group, a butylene group, a 1-methyltrimethylene group, a 2-methyltrimethylene group, pentamethylene group, a pentylene group, 2,2-dimethylpropylene group, 2-methylpropylene group, 2-ethylpropylene group, a 1-methyltetramethylene group, a 2-methyltetramethylene group, a 1,1-dimethylethylene group, 1,2-dimethylethylene group, a 1,3-dimethyltrimethylene group, a 2,2-dimethyltrimethylene group, a 2-ethyltrimethylene group, a hexamethylene group, a hexylene group, a heptylene group, an octylene group, a 2-ethylhexylene group, a nonamethylene group, a nonylene group, a decamethylene group, a decylene group, a 1,4-dimethyltetramethylene group, a 2,3-dimethyltetramethylene group, a 1,2,3-trimethyltrimethylene group, a 1,2-diethylethylene group, a heptamethylene group, a 1,5-dimethylpentamethylene group, a 3-ethylpentamethylene group, an octamethylene group, a 1,6-dimethylhexamethylene group, a cyclopropylene group, a cyclopentylene group, a cyclohexylene group, a cycloheptylene group, a cyclooctylene group, a cyclononylene group, a cyclodecylene group, a cyclopropane-1,2-dimethylene group, a cyclopentane-1,3-dimethylene group, a cyclohexane-1,4-dimethylene group, a cyclohexane-1,4-diethylene group, a cyclooctane-1,5-dimethylene group, an adamantanediyl group, a tricyclo[5.2.1.02.6]-decanediyl group, a norbornanediyl group, a methylnorbornanediyl group, an isobornanediyl group, and a decalinediyl group.

The arylene group represented by $T^1$ of the general formula (1) may be a monocyclic, a condensed polycyclic, or a non-condensed polycyclic group, and in general, includes a group having 5 to 14 carbon atoms.

In particular, the arylene group is exemplified by, for example, a phenylene group, a tolyl group, a xylyl group, a mesityl group, a naphthylene group, an anthracenediyl group, a phenanthracenediyl group, and a biphenyldiyl group.

As the aralkylene group represented by $T^1$ of the general formula (1), a group formed in combination of an alkylene group and an arylene group may be included. The aralkylene group may be straight chained or branched and includes generally has 7 to 10 carbon atoms.

In particular, the aralkylene group is exemplified by, for example, —$CH_2$—$C_6H_4$—, —$CH_2CH_2$—$C_6H_4$—, —$CH_2$—$C_6H_4$—$CH_2$—, —$CH_2CH_2$—$C_6H_4$—$CH_2$—, —$CH_2CH_2CH_2$—$C_6H_4$—, —$CH(CH_3)$—$CH_2$—$C_6H_4$—, —$CH_2CH_2CH_2CH_2$—$C_6H_4$—, and —$CH_2CH_2CH(CH_3)$—$C_6H_4$—.

The alkylene group containing a hetero atom, the arylene group containing a hetero atom, or the aralkylene group containing a hetero atom represented by $T^1$ of the general formula (1) is formed by replacement of a carbon atom located at an arbitrary location of the above alkylene group, the arylene group, and the aralkylene group with a divalent group containing a hetero atom, in other words, the above group is a group containing a divalent group having a hetero atom at an arbitrary location in the chains of the arkylene group, the arylene group, and the aralkylene group, and has no reaction activity or very low reaction activity with the leaving group represented by Z, phosphoric group, a carboxyl group, a hydroxyl group, an amino group, or the like. The divalent group containing a hetero atom includes, for example, a group containing a nitrogen atom, a sulfur atom, an oxygen atom, or the like and have no reaction activity or very low reaction activity with the leaving group represented by Z, phosphoric group, a carboxyl group, a hydroxyl group, an amino group, or the like. In particular, the divalent group is exemplified by, for example, a carbonyl group, a thiocarbonyl group, an imino group, a malonyl group, —S—, —O—, —N—, or the following groups, etc.

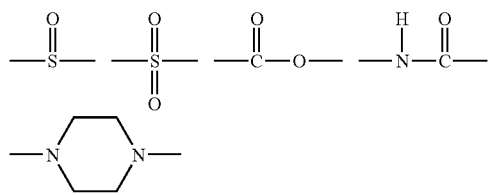

In the general formula (1), the alkyl groups represented by $R^1$, $R^2$, and $R^3$ may be straight chained, branched, or cyclic and include one having generally 1 to 12 carbon atoms, preferably 1 to 6 and more preferably 1 to 4.

In particular, the alkyl group is exemplified by, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a sec-hexyl group, a tert-hexyl group, a neohexyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a n-nonyl group, an isononyl group, a sec-nonyl group, a tert-nonyl group, a neononyl group, a n-decyl group, an isodecyl group, a sec-decyl group, a tert-decyl group, a neodecyl group, a n-undecyl group, an isoundecyl group, a sec-undecyl group, a tert-undecyl group, a neoundecyl group, a n-dodecyl group, an isododecyl group, a sec-dodecyl group, a tert-dodecyl group, a neododecyl group, a cyclopropyl group, a cyclobutyl group, a cyclopentyl group, a cyclohexyl group, a cycloheptyl group, a cyclooctyl group, a cyclononyl group, a cyclodecyl group, a cycloundecyl group, and a cyclododecyl group.

As for the linker portion of the present invention, the number of atoms forming the main chain in -$A^1$-$T^1$-$A^2$-, is generally 5 or more and preferably 7 or more as the lower limit and is generally 80 or less and preferably 70 or less as the upper limit.

The linker portion -$A^1$-$T^1$-$A^2$- of the present invention is preferably represented by -$A^3$-$(T^2-E)_p$-$T^3$-$A^4$-.

In this case, $A^3$ and $A^4$ each independently represent an alkylene group, —O—, —$NR^1$—, —O—CO—, —CO—O—, —C—O—C—, —$NR^2$—COO—, —OCO—$NR^2$—, —$NR^3$—CO—, —CO—$NR^3$—, or —O—COO— ($R^1$ to $R^3$ are the same as described above); $T^2$ and $T^3$ each independently represent an alkylene group; and E represents a binding hand, a nitrogen atom, a sulfur atom, an oxygen atom, —O—CO—, or —CO—O—. In addition, p represents an integer of 1 or more, and p-($T^2$-E)- may be the same or may be different from each other.

The alkylene groups represented by $A^3$, $A^4$, $T^2$, and $T^3$ may be straight chained, branched, or cyclic and include one having generally 1 to 10 carbon atoms and preferably 1 to 8 carbon atoms. The concrete examples are the same as the alkylene groups represented by $A^1$, $A^2$, and $T^1$.

The lower limit of p is 1 or more, and the upper limit is generally 6 or less, preferably 4 or less, and more preferably 2 or less.

In addition, although p-($T^2$-E)- may be the same or may be different from each other, $T^2$ bound to $A^3$ (adjacent thereto) is preferably the same as $T^3$.

As for the linker portion described above, the number of atoms forming the main chain in -$A^3$-$(T^2-E)_p$-$T^3$-$A^4$-, is generally 5 or more and preferably 7 or more as the lower limit and is generally 80 or less and preferably 70 or less as the upper limit.

As the linker of the present invention, in more particular, for example, groups represented by the following formulas are exemplified.

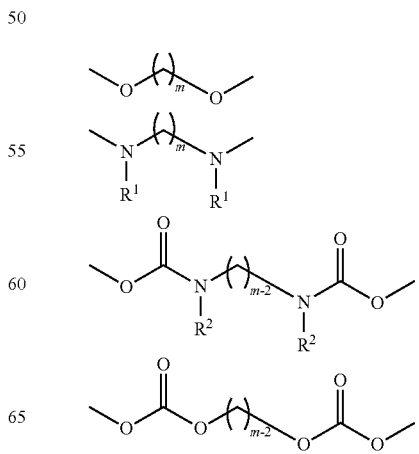

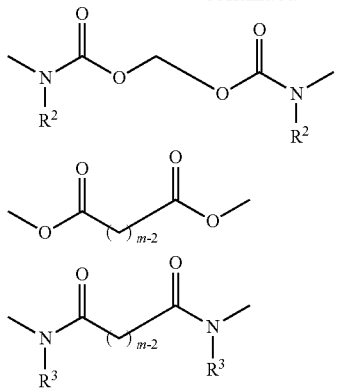

[In the above formulas, $R^1$ to $R^3$ are the same as described above, and m represents an integer of 3 or more. In this case, two $R^1$ may be the same or may be different from each other, and two $R^2$ may be the same or may be different from each other. In addition, two $R^3$ may be the same or may be different from each other.]

In this case, the lower limit of m is generally 3 or more and preferably 5 or more, and the upper limit thereof is generally 78 or less and preferably 68 or less.

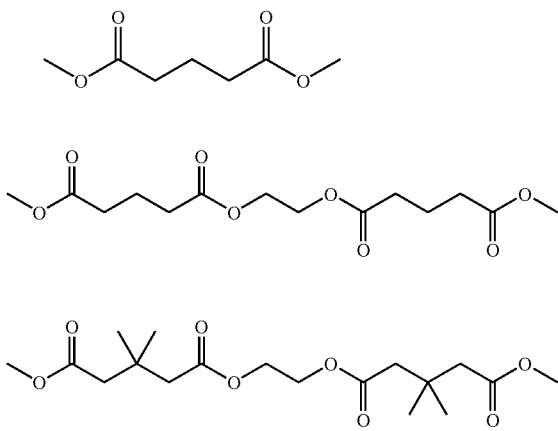

1-3. Concrete Compound (Crosslinking Agent)

As described above, the compound (crosslinking agent) of the present invention is composed of a linker and photodegradable protective groups bound to two ends thereof and is a compound represented by the general formula (1) and preferably by the general formula (2).

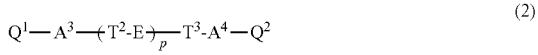

[In the above formulas, $Q^1$, $Q^2$, $A^1$, $A^2$, $A^3$, $A^4$, $T^1$, $T^2$, $T^3$, E and p are the same as described above.]

As the compound (crosslinking agent) of the present invention, in particular, for example, a compound represented by the following general formula (6) is exemplified.

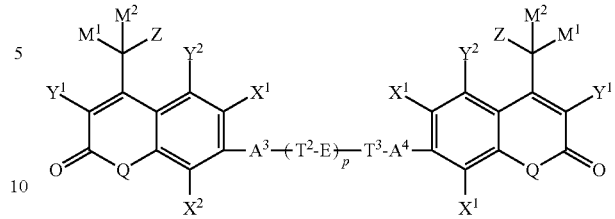

[In the above formula, Q, $Y^1$, $Y^2$, $M^1$, Z, $M^2$, $X^1$, $X^2$, $A^3$, $A^2$, $T^3$, $T^3$, E and p are the same as described above.]

In addition, among the compounds (crosslinking agents) of the present invention, as a compound which is bound to a phosphoric group of a target object (a nucleic acid, a protein, or a polypeptide) for crosslinking thereof, for example, a compound represented by the following general formula (7) is exemplified.

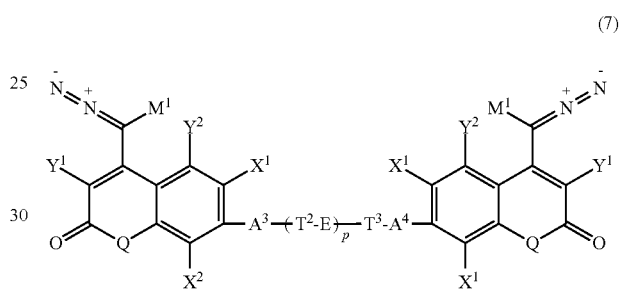

[In the above formula, Q, $Y^1$, $Y^2$, $M^1$, $Z^{11}$, $M^2$, $X^1$, $X^2$, $A^3$, $A^4$, $T^2$, $T^3$, E and p are the same as described above.]

Among the compounds (crosslinking agents) of the present invention, as a compound which is bound to a carboxyl group, a hydroxyl group, or an amino group of a target object (a nucleic acid, a protein, or a polypeptide) for crosslinking thereof, for example, a compound represented by the following general formula (8) is exemplified.

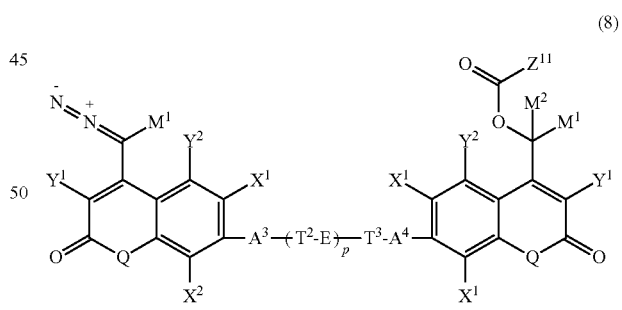

[In the above formula, Q, $Y^1$, $Y^2$, $M^1$, $Z^{11}$, $M^2$, $X^1$, $X^2$, $A^3$, $A^4$, $T^2$, $T^3$, E and p are the same as described above.]

Among the compounds (crosslinking agents) of the present invention, as a compound which is bound to a phosphoric group and one of a carboxyl group, a hydroxyl group, and an amino group of an target object (a nucleic acid, a protein, or a polypeptide) for crosslinking thereof, that is, as a compound having two photodegradable protective groups, one being bound to a phosphoric group of the target object and the other being bound to a carboxyl group, a hydroxyl group, or an amino group for crosslinking of the target object, for example, a compound represented by the following general formula (9) is exemplified.

(9)

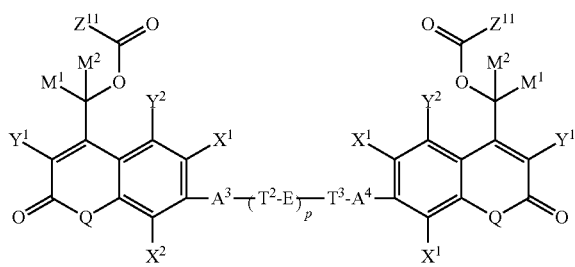

[In the above formula, Q, $Y^1$, $Y^2$, $M^1$, $Z^{11}$, $M^2$, $X^1$, $X^2$, $A^3$, $A^4$, $T^2$, $T^3$, E and p are the same as described above.]

1-4. Synthesis of Compound (Crosslinking Agent) of the Present Invention

The compound (crosslinking agent) of the present invention represented by the general formula (1) can be easily synthesized, for example, in accordance with synthetic schemes shown below.

In the following synthetic scheme, Q, $Y^1$, $Y^2$, $M^1$, Z, $Z^{11}$, $M^2$, $X^1$, $X^2$, $R^1$, $R^2$, $R^3$, and m are the same as described above. In addition, the formal names of abbreviations used in the following synthetic schemes are as follows.

$Et_3N$: triethylamine
DMF: dimethylformamide

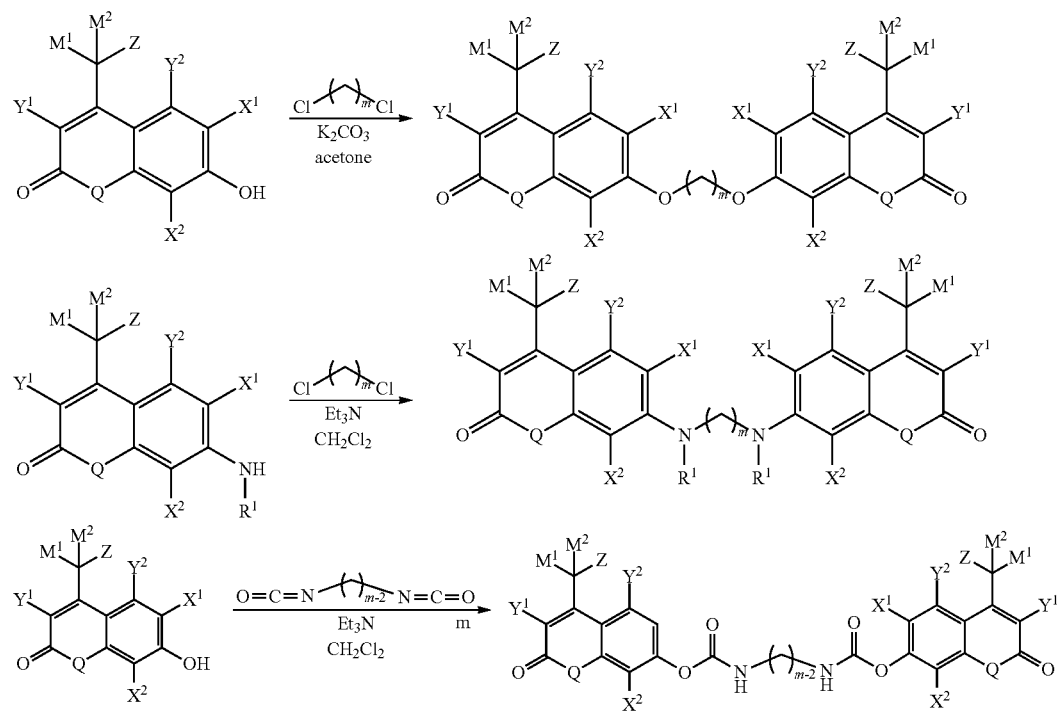

(When $R^2$ is H, for example, synthesis can be performed in accordance with the above synthetic schemes.)

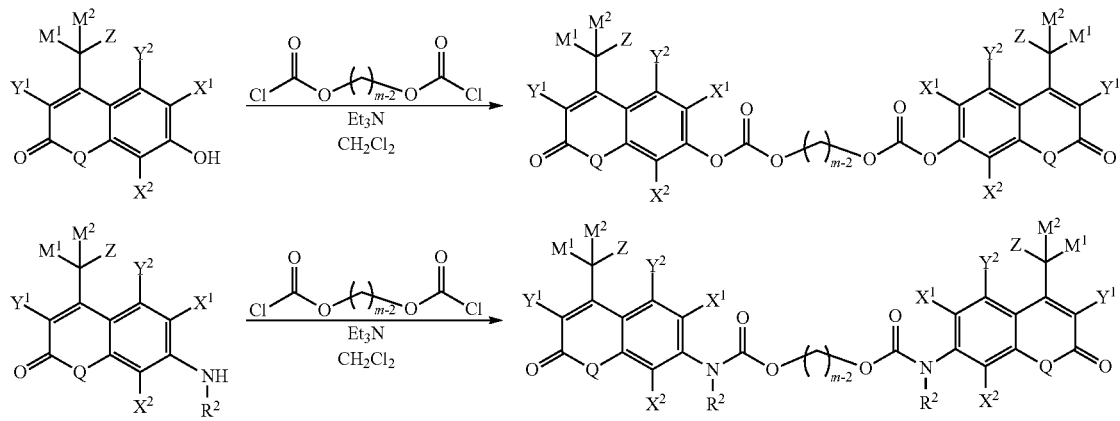

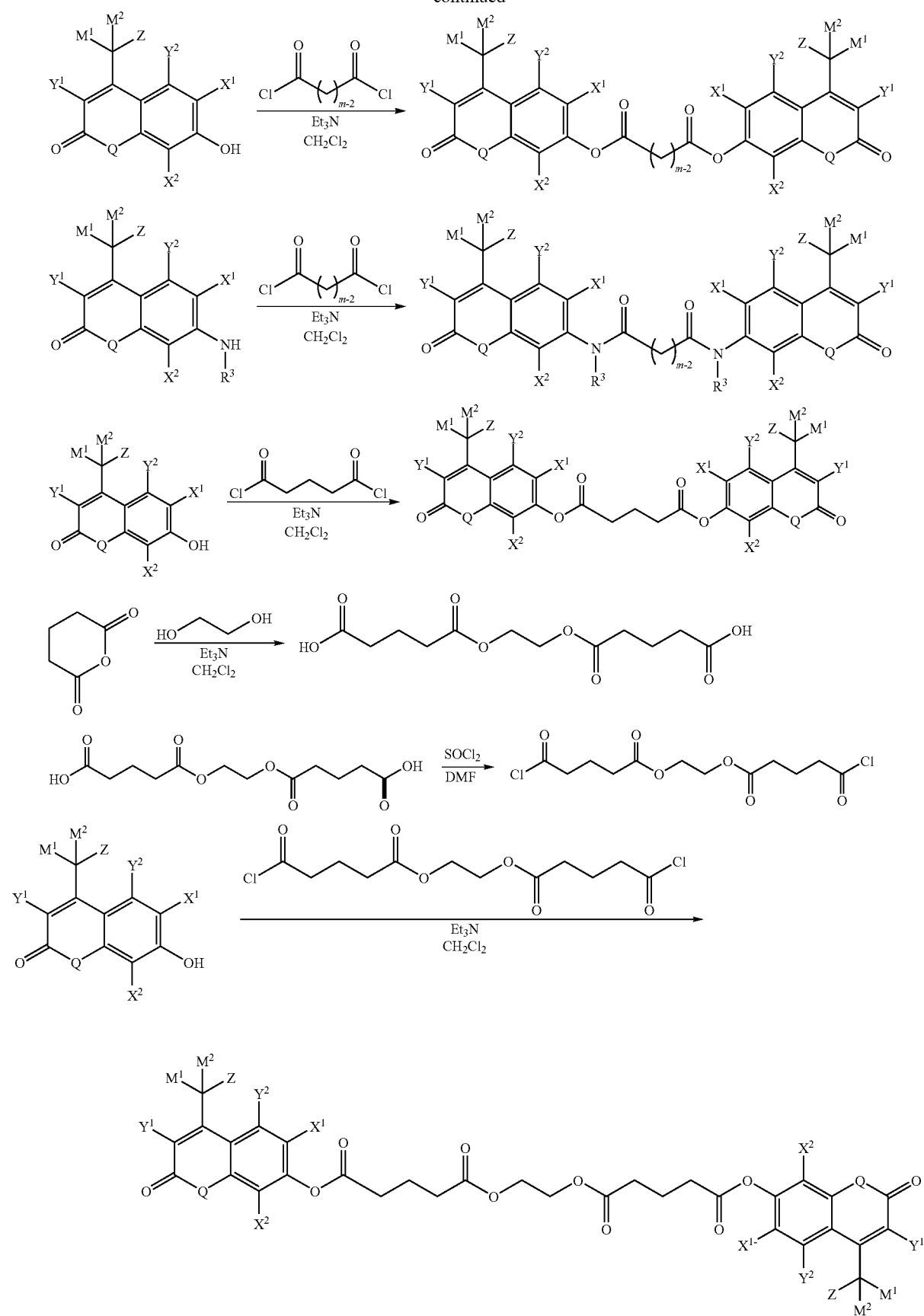

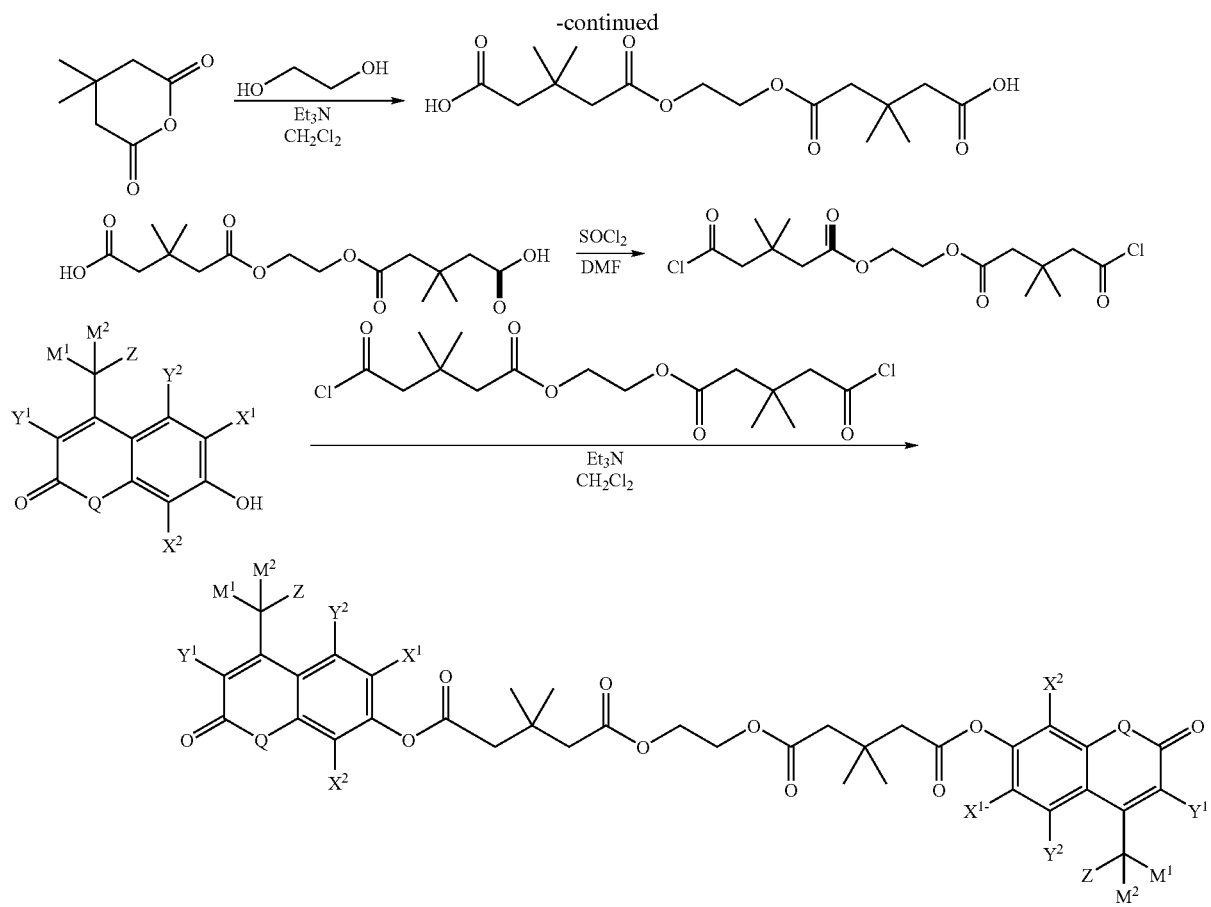

2. Crosslinking Method of the Present Invention

According to the compound (crosslinking agent) of the present invention, crosslinking can be easily formed between double-stranded nucleic acid, between a nucleic acid and a protein or a polypeptide, or between proteins or polypeptides [that is, between a sense chain and an antisense chain of a double-stranded nucleic acid, between a nucleic acid and a protein or a polypeptide, or between two proteins or two polypeptides (between proteins, between a protein and a polypeptide, or between polypeptides) (hereinafter referred to as a "complex of the present invention" in some cases).

That is, since having a group in each of the photodegradable protective groups which can be bound to a group selected from a phosphoric group, a carboxyl group, a hydroxyl group, an amino group, and the like, the compound (crosslinking agent) of the present invention can be bound to groups each selected from a phosphoric group, a carboxyl group, a hydroxyl group, and an amino group of a target object (a nucleic acid, a protein, or a polypeptide) constituting the complex of the present invention, and as a result, the complex of the present invention can be crosslinked.

In other words, of the two photodegradable protective groups of the compound (crosslinking agent) of the present invention, one is bound to a group selected from a phosphoric group, a carboxyl group, a hydroxyl group, and an amino group of one target object (a nucleic acid, a protein, or a polypeptide) forming the complex of the present invention, and the other is bound to a group selected from a phosphoric group, a carboxyl group, a hydroxyl group, and an amino group of the other target object, so that the complex (two target objects forming the complex) of the present invention can be crosslinked.

As a result, the complex (two target objects forming the complex) of the present invention can be crosslinked by the compound (crosslinking agent) of the present invention with a phosphoric moiety, a carboxyl group, a hydroxyl group, or an amino group provided therebetween.

Accordingly, the crosslinking method of the present invention is to crosslink double-stranded nucleic acid, a nucleic acid and a protein or a polypeptide, or proteins or polypeptides via groups selected from a phosphoric group, a carboxyl group, a hydroxyl group, and an amino group of the complex by the compound (crosslinking agent) of the present invention, preferably by the compound represented by the general formula (1), more preferably by the compound represented by the general formula (2), and even more preferably by the compound represented by the general formula (6).

In more particular, the crosslinking method of the present invention is 1) to crosslink the complex (in particular, a double-stranded RNA) of the present invention via phosphoric moieties of the complex (in particular, a double-stranded RNA) by a crosslinking agent having photodegradable protective groups at two ends which include groups to be bound to phosphoric group or by the compound represented by the general formula (7); 2) to crosslink the complex of the present invention via a phosphoric moiety thereof and a carboxyl group, a hydroxyl group, or an amino group by the compound represented by the general formula (9); and 3) to crosslink the complex of the present invention via a carboxyl group, a hydroxyl group, or an amino group of the complex by the compound represented by the general formula (8).

In the methods described above, the double-stranded nucleic acid used as an object to be crosslinked is not particularly limited as long as it has a double-stranded structure.

In particular, the double-stranded nucleic acid includes, for example, compounds (such as a double-stranded DNA, a double-stranded RNA, and a DNA-RNA hybrid) each composed of two nucleic acids selected from DNAs, such as a plasmid DNA, a genome DNA, a synthetic DNA synthesized by a known amplification method, such as a PCR method, and a cDNA; RNAs, such as an mRNA and an antisense RNA; and cyclic nucleotides. Among those mentioned above, a double-stranded RNA is preferable.

In addition, the protein to be crosslinked is not particularly limited as long as it can form a complex with a nucleic acid or can form a complex with another protein or polypeptide as described above.

In particular, the protein includes, for example, transcription factors, such as NFκB, NFAT, and STAT; and RNA polymerases.

The polypeptide to be crosslinked is not particularly limited as long as it can form a complex with a nucleic acid or can form a complex with another polypeptide or protein as described above.

In particular, the polypeptide includes, for example, PKCε V1-2 inhibitor peptide, RGD peptide, Zn finger peptide, leucine zipper peptide, and bHLH peptide.

Among the above-described objects to be crosslinked, the present invention is effectively applied, in particular, to a double-stranded RNA.

In order to crosslink the complex of the present invention as described above using the compound (crosslinking agent) of the present invention, the compound (crosslinking agent) of the present invention and the complex of the present invention may be brought into contact with each other.

The method for bringing the compound (crosslinking agent) of the present invention into contact with the complex of the present invention may be preformed, for example, by mixing a solution containing the compound (crosslinking agent) of the present invention and a solution containing the complex of the present invention, and reacting for generally 1 hour or more, preferably 4 hours or more, and more preferably 8 hours or more as the lower limit and generally 36 hours or less and preferably 24 hours or less as the upper limit; at generally 10° C. or more, preferably 15° C. or more, and more preferably 20° C. or more as the lower limit and generally 40° C. or less, preferably 35° C. or less, and more preferably 25° C. or less as the upper limit.

Although the amount of the compound (crosslinking agent) of the present invention used in this case cannot be simply determined since it varies depending on types of compounds (crosslinking agents) of the present invention to be used and types of complexes of the present invention which is an object to be crosslinked, the lower limit of the amount is generally 1 mole or more with respect to 1 mole of the object to be crosslinked (complex of the present invention), is preferably more than 1 mole with respect to 1 mole of the object to be crosslinked (complex of the present invention) and one fourth or more of the number of combinations of reaction groups (a phosphoric group, a carboxyl group, a hydroxyl group, an amino group, and the like) which are crosslinkable in the object to be crosslinked, and is more preferably an amount on a molar quantity that corresponds to the number of combinations of reaction groups which are crosslinkable in the object to be crosslinked. The upper limit on a molar quantity is 10 times the number of combinations of reaction groups which are crosslinkable in the object to be crosslinked and is preferably 5 times the number of combinations of reaction groups which are crosslinkable in the object to be crosslinked.

In this case, the combination of reaction groups which are crosslinkable in the object to be crosslinked means the combination between reaction groups (such as a group selected from a phosphoric group, a carboxyl group, a hydroxyl group, and an amino group) of one target object (a nucleic acid, a protein, or a polypeptide) forming the complex of the present invention, to which one of the two photodegradable protective groups of the compound (crosslinking agent) of the present invention can be bound, and reaction groups (such as a group selected from a phosphoric group, a carboxyl group, a hydroxyl group, and an amino group) of the other target object (a nucleic acid, a protein, or a polypeptide) forming the complex of the present invention, to which the other one of the two photodegradable protective groups of the compound (crosslinking agent) of the present invention can be bound.

In addition, the number of combinations of reaction groups which are crosslinkable in the object to be crosslinked indicates the total number of the reaction groups of the object to be crosslinked as described above (the number of all combinations), to which the compound (crosslinking agent) of the present invention can be bound, and in other words, between the number of the reaction groups of one target object forming the complex of the present invention, to which one of the two photodegradable protective groups of the compound (crosslinking agent) of the present invention can be bound, and the number of the reaction groups of the other target object forming the complex of the present invention, to which the other one of the two photodegradable protective groups of the compound (crosslinking agent) of the present invention can be bound, a smaller number indicates the number of combinations of reaction groups.

In addition, as the solution containing the compound (crosslinking agent) of the present invention and/or the complex of the present invention described above, any solutions which have been generally used in this field may be used and are not particularly limited, and for example, water, DMSO, and a buffer solution (such as a Tris buffer solution, a Good's buffer solution, a TE buffer solution, a TAE buffer solution, a TBE buffer solution, and a TBS buffer solution) are included.

The complex of the present invention thus obtained which is bound with the compound (crosslinking agent) of the present invention is generally processed by a known purification method, such as column chromatography, to remove an unreacted compound (crosslinking agent) of the present invention, so that the complex of the present invention bound with the compound (crosslinking agent) of the present invention is preferably purified.

The present invention also includes the complex of the present invention which is bound with (crosslinked by) the compound (crosslinking agent) of the present invention, that is, includes a double-stranded nucleic acid, a nucleic acid-protein complex, a nucleic acid-polypeptide complex, two proteins, a protein-polypeptide complex, and two polypeptides, which are bound with (crosslinked by) the compound (crosslinking agent) of the present invention.

Among these described above, as the complex of the present invention bound with (crosslinked by) the compound (crosslinking agent) of the present invention, a double-stranded nucleic acid bound with (crosslinked by) the compound (crosslinking agent) of the present invention is preferable, and in particular, a double-stranded RNA bound with (crosslinked by) the compound (crosslinking agent) of the present invention is more preferable. In addition, preferable examples of the compound (crosslinking agent) of the present invention are as described above.

When the compound (crosslinking agent) of the present invention crosslinks the complex of the present invention, the complexes of the present invention, that is, double-stranded nucleic acid, such as a double-stranded DNA, a double-stranded RNA, and a DNA-RNA hybrid; a nucleic acid-protein complex; a nucleic acid-polypeptide complex; a protein complex; a polypeptide complex; and a protein-polypeptide complex, are suppressed from exhibiting their original functions.

For example, in the case in which the complex of the present invention is a double-stranded DNA, in a host having a transcription system, the transcription of the nucleic acid molecule is suppressed, and as a result, the expression of the gene is suppressed.

In addition, in the case in which the complex of the present invention is a double-stranded RNA, in RNAi, a specific decomposition effect of siRNA on a target mRNA complementary thereto is suppressed.

In the case in which the complex of the present invention is a nucleic acid-protein complex, in a host having a transcription system, the transcription of a nucleic acid molecule located downstream of the above nucleic acid molecule is suppressed or activated, and as a result, the expression of the gene is suppressed or activated.

In the case in which the complex of the present invention is a nucleic acid-polypeptide complex, in a host having a transcription system, the transcription of a nucleic acid molecule located downstream of the above nucleic acid molecule is suppressed or activated, and as a result, the expression of the gene is suppressed or activated.

In the case in which the complex of the present invention is a protein complex, the function of the protein is suppressed or activated in a cell.

When the complex of the present invention which is crosslinked by the compound (crosslinking agent) of the present invention is irradiated with light, such as UV light or visible light, the compound (crosslinking agent) of the present invention can be eliminated from the complex of the present invention. By the step described above, the suppression of the function of the complex of the present invention can be removed (released).

That is, the complex of the present invention which is crosslinked by the compound (crosslinking agent) of the present invention is suppressed from exhibiting its original function; however, since the binding between the compound (crosslinking agent) of the present invention and the complex of the present invention is removed by irradiation of light (since the crosslinking caused by the compound (crosslinking agent) of the present invention is removed), the function of the complex is restored.

The light irradiated in the present invention means electromagnetic waves having a wavelength longer than that of x rays and in the range of approximately 1 to 900 nm. In particular, a light at a long wavelength side, for example, in the range of 350 to 400 nm is preferable, and light having a wavelength of approximately 365±6 nm is more preferable.

In addition, since being depending on types of compounds (crosslinking agent) of the present invention and types of complexes of the present invention to be crosslinked, the irradiation time of the light cannot be simply determined; however, when the irradiation time is long, mutation may be induced in a nucleic acid molecule, or a cell or an organism to be transfected with the complex of the present invention crosslinked by the compound (crosslinking agent) of the present invention may be damaged, and on the other side, when the irradiation time is short, the compound (crosslinking agent) of the present invention may not be sufficiently eliminated in some cases. In particular, for example, the lower limit of the time using light of 4 mJ/cm$^2$s may be 1 minute or more, and the upper limit may be generally 10 minutes or less or preferably 3 minutes or less. Alternatively, the lower limit of the time using light of 376 mJ/cm$^2$s may be generally 0.1 seconds or more or preferably 1 second or more, and the upper limit may be generally 30 seconds or less or preferably 10 seconds or less.

As described above, by the compound (crosslinking agent) of the present invention and by the crosslinking method using the same, the complexes of the present invention (double-stranded nucleic acid, such as a double-stranded DNA, a double-stranded RNA, and a DNA-RNA hybrid; a nucleic acid-protein complex; a nucleic acid-polypeptide complex; a protein complex; a polypeptide complex; and a protein-polypeptide complex) having various functions can be suppressed from exhibiting their functions.

Furthermore, by irradiating the complex of the present invention crosslinked by the compound (crosslinking agent) of the present invention with light, the function of the complex of the present invention, which is suppressed, is restored at an arbitrary timing and location, in other words, the function of the complex of the present invention can be controlled at an arbitrary timing and location.

For example, an unknown function of a double-stranded nucleic acid, such as a double-stranded DNA, a double-stranded RNA, or a DNA-RNA hybrid; a nucleic acid-protein complex; a nucleic acid-polypeptide complex; a protein complex; a polypeptide complex; or a protein-polypeptide complex can be specifically expressed at an arbitrary timing, can be specifically expressed at an arbitrary location, or can be specifically expressed at an arbitrary timing and location.

The compound (crosslinking agent) of the present invention and the crosslinking method using the same can also be applied to applications other than that described above.

For example, after the complex (a double-stranded nucleic acid, such as a double-stranded DNA, a double-stranded RNA, or a DNA-RNA hybrid; a nucleic acid-protein complex; a nucleic acid-polypeptide complex; a protein complex; a polypeptide complex; or a protein-polypeptide complex) of the present invention formed, in vivo or in vitro is crosslinked by the compound (crosslinking agent) of the present invention, and the crosslinked complex is isolated, when the complex is irradiated with light, without changing individual components (a nucleic acid chain, a protein, and/or a polypeptide) constituting the complex, isolation can be performed while the functions thereof are maintained. Accordingly, by the method described above, since the components constituting the complex can be identified, and furthermore, since the functions of the individual constituent components are also maintained, for example, the formative action of the complex (interaction between the individual constituent components) in a cell, a tissue, an organism, or the like and the functions of the components can be significantly effectively analyzed.

In addition, for example, in the case in which the complex of the present invention has a beneficial effect (such as so-called RNAi medicine using RNAi), when the complex of the present invention is crosslinked by the compound (crosslinking agent) of the present invention so as to suppress its beneficial effect, and the crosslinked complex is irradiated with light after it is administered to a cell, a tissue, an organism, or the like, the suppressed beneficial effect can be restored, so that, for example, treatment of diseases can be performed. According to the method described above, by controlling the area and/or the time of light irradiation, a beneficial effect can be specifically obtained at a targeted specific position (focus of disease or the like) or can be obtained at an arbitrary timing (time).

3. Method for Regulating Gene Expression of the Present Invention

The compound (crosslinking agent) of the present invention and the crosslinking method using the same can be used in various applications as described above and are particularly effective in an RNAi method using a double-stranded RNA.

The method for regulating gene expression of the present invention comprises the step of irradiating a double-stranded RNA bound beforehand with the compound (crosslinking agent) of the present invention as described above with light.

That is, by binding the compound (crosslinking agent) of the present invention to a double-stranded RNA, in other words, by crosslinking a double-stranded RNA by the compound (crosslinking agent) of the present invention, a gene-expression inhibitory effect (effect of decomposing a target mRNA complementary to the double-stranded RNA) of the double-stranded RNA can be suppressed. That is, when the compound (crosslinking agent) of the present invention is bound to a double-stranded RNA (siRNA) corresponding to a predetermined gene (target mRNA) so as to crosslink the double-stranded RNA (siRNA), the gene (target mRNA) in a cell or an organism can be expressed. Next, by irradiating the double-stranded RNA crosslinked by the compound (crosslinking agent) of the present invention with light, the compound (crosslinking agent) of the present invention is eliminated from the complex, and the gene-expression inhibitory effect (effect of decomposing a target mRNA complementary to the double-stranded RNA) of the double-stranded RNA, which is suppressed, can be restored; hence, as a result, the expression of the gene (target mRNA) can be suppressed. Accordingly, the expression of a specific gene (target mRNA) can be regulated (controlled) at an arbitrary timing and location.

Except that a double-stranded RNA, which is used in a known gene-expression regulation method using a double-stranded RNA, such as an RNAi method using a double-stranded RNA, is crosslinked beforehand by the compound (crosslinking agent) of the present invention, and except that the above double-stranded RNA crosslinked by the compound (crosslinking agent) of the present invention is irradiated with light when the expression of a gene is regulated, that is, when the expression of a gene is suppressed, the method for regulating gene expression, according to the present invention may be carried out in accordance with a known method, and in addition, materials, reagents, and the like used in a known method may also be used.

In particular, the method for regulating gene expression of the present invention comprises the following steps (a) to (c):

a step (a) of contacting a double-stranded RNA with the compound (crosslinking agent) of the present invention to crosslink the double-stranded RNA;

a step (b) of transfecting the crosslinked double-stranded RNA into a cell or an organism; and a step (c) of irradiating the transfected cell or organism with light.

3-1. Step of Crosslinking Double-Stranded RNA [Step (a)]

(1) Double-Stranded RNA

As the double-stranded RNA used in the method of the present invention, a double-stranded RNA which can mediate RNAi (capable of producing RNAi) may be used, that is, any double-stranded RNA (having ability to decompose a target mRNA) may be used as long as it causes a phenomenon in which the expression of a target protein is specifically suppressed by the double-stranded RNA that promotes specific decomposition of a target mRNA complementary thereto, and for example, RNA extracted from natural products, such as various cells, organisms, and tissues; synthetic RNA; recombinant RNA may all be used.

Ribonucleotides forming a double-stranded RNA may include, for example, a ribonucleotide containing a non-naturally occurring nucleic-acid base (uridine or cytidine modified at the position 5, such as 5-(2-amino)propyluridine or 5-bromouridine; adenosine and guanosine modified at the position 8, such as 8-bromoguanosine; deazanucleotide such as 7-deaza-adenosine; or O- and N-alkylated nucleotide such as N6-methyladenosine); a sugar-modified ribonucleotide (such as a sugar-modified ribonucleotide in which the 2'OH group of the sugar is replaced with a group selected from H, OR, a halogen atom, SH, $SR^{41}$, $NH_2$, $NHR^{41}$, $NR^{41}{}_2$ and CN, where $R^{41}$ represents C1 to C6 alkyl, alkenyl, or alkynyl, and a halogen atom represents F, Cl, Br, or I); a backbone-modified ribonucleotide (in which for example, a phosphoester group binding an adjacent ribonucleotide is replaced with a modified group, such as a phosphothioate group); and a ribonucleotide formed in combination of the above-described ribonucleotides.

In addition, the sequence of the double-stranded RNA used for the method of the present invention must have a sufficient identity to a target mRNA. Preferably, this sequence in a double-stranded portion of the double-stranded RNA has an identity of at least 50%, preferably at least 70%, more preferably at least 85%, and particularly preferably 100% to the target mRNA.

The length of the double-stranded RNA is not particularly limited as long as it can mediate RNAi (having ability to produce RNAi). In particular, the lower limit of each RNA chain is generally 19 bases or more, preferably 20 bases or more, and more preferably 25 bases or more, and the upper limit is generally 1,500 bases or less, preferably bases or less, and more preferably 500 bases or less. When a cell or an organism transfected with a double-stranded RNA is an animal, the upper limit is preferably 30 bases or less and more preferably 27 bases or less.

As the double-stranded RNA as described above, for example, double-stranded RNAs described in PCT Japanese Translation Patent Publications Nos. 2003-529374, 2004-526422, and 2002-516112, Japanese Unexamined Patent Application Publication No. 2004-261002 are included.

The double-stranded RNA as described above can be obtained by known methods generally used in this field [for example, methods disclosed in PCT Japanese Translation patent Publications Nos. 2003-529374, 2004-526422, and 2002-516112, Japanese Unexamined Patent Application Publication No. 2004-261002, and the like] or can be obtained by using a commercially available kit.

In general, a double-stranded RNA is prepared as a solution containing a double-stranded RNA by dissolving a double-stranded RNA in an appropriate solvent to give RNA concentration generally 1 µM or more, preferably 10 µM or more, and more preferably 20 µM or more as the lower limit, and generally 100 µM or less, preferably 50 µM or less, and more preferably 30 µM or less as the upper limit.

(2) Contact Between Compound (Crosslinking Agent) of the Present Invention and Double-Stranded RNA In order to crosslink a double-stranded RNA by bringing it into contact with the compound (crosslinking agent) of the present invention, for example, a solution containing the compound (crosslinking agent) of the present invention and a solution containing a double-stranded RNA may be mixed together and reacted for generally 1 hour or more, preferably 4 hours or more, and more preferably 8 hours or more as the lower limit and generally 36 hours or less and preferably 24 hours or less as the upper limit; at generally 10° C. or more, preferably 15° C. or more, and more preferably 20° C. or more as the lower limit and generally 40° C. or less, preferably 35° C. or less, and more preferably 25° C. or less as the upper limit.

As the compound (crosslinking agent) of the present invention used in the above method, a crosslinking agent is preferable which has photodegradable protective groups at two ends, each including a group bindable to phosphoric group, and the compound (crosslinking agent) represented by the general formula (7) is particularly preferable.

Although the amount of the compound (crosslinking agent) of the present invention used in this case cannot be simply determined since it varies depending on types of compounds (crosslinking agent) of the present invention to be used and the like, the lower limit of the amount is generally 1 mole or more with respect to 1 mole of a double-stranded RNA to be crosslinked, is preferably more than 1 mole with respect to 1 mole of a double-stranded RNA and one fourth or more of the number of combinations of reaction groups (a phosphoric group, a carboxyl group, a hydroxyl group, an amino group, and the like) which are crosslinkable in the double-stranded RNA, and is more preferably an amount on a molar quantity that corresponds to the number of combinations of reaction groups which are crosslinkable in the double-stranded RNA. The upper limit on a molar quantity is 10 times the number of combinations of reaction groups which are crosslinkable in the double-stranded RNA and is preferably 5 times the number of combinations of reaction groups which are crosslinkable in the double-stranded RNA.

In this case, the combination of the reaction groups which are crosslinkable in the double-stranded RNA means the combination between reaction groups (such as a group selected from a phosphoric group, a hydroxyl group, and an amino group) of one RNA chain forming the double-stranded RNA, to which one of the two photodegradable protective groups of the compound (crosslinking agent) of the present invention can be bound, and reaction groups (such as a group selected from a phosphoric group, a hydroxyl group, and an amino group) of the other RNA chain forming the double-stranded RNA, to which the other one of the two photodegradable protective groups of the compound (crosslinking agent) of the present invention can be bound.

In addition, the number of combinations of reaction groups crosslikable in the double-stranded RNA indicates the total number of the reaction groups of the double-stranded RNA as described above (the number of all combinations) to which the compound (crosslinking agent) of the present invention can be bound, and in other words, between the number of the reaction groups of one RNA chain forming the double-stranded RNA, to which one of the two photodegradable protective groups of the compound (crosslinking agent) of the present invention can be bound, and the number of the reaction groups of the other RNA chain forming the double-stranded chain, to which the other one of the two photodegradable protective groups of the compound (crosslinking agent) of the present invention can be bound, a smaller number indicates the number of combinations of reaction groups.

In addition, as the solution containing the double-stranded RNA and/or the compound (crosslinking agent) of the present invention, any solutions which have been generally used in this field may be used and are not particularly limited, and for example, water, DMSO, and a buffer solution (such as a Tris buffer solution, a Good's buffer solution, a TE buffer solution, a TAE buffer solution, a TBE buffer solution, and a TBS buffer solution) is included.

In the method described above, the reaction solution is preferably processed by a known purification method, such as column chromatography, to remove an unreacted compound (crosslinking agent) of the present invention, so that the double-stranded RNA bound with the compound (crosslinking agent) of the present invention is purified.

3-2. Double-Stranded RNA Transfection Step [Step (b)]

The double-stranded RNA bound with the compound (crosslinking agent) of the present invention, thus formed, is introduced (transfected) into a cell or an organism.

(1) Cell or Organism

As a cell and an organism to be used in the present invention, any cell or organism may be used and is not particularly limited as long as it is capable of transmitting irradiated light and supplying energy thereof to the introduced (transfected) double-stranded RNA.

The cell as described above includes, for example, a eukaryotic cell or a cell line; a plant cell or an animal cell (a mammalian cell of human, rat, or the like; a nematode cell; an insect cell, or the like); an embryonic cell (a Xenopus embryonic cell in early development, an zebrafish embryonic cell, a Drosophila embryonic cell, or the like); a pluripotent stem cell; a tumor cell; a teratocarcinoma cell or a virus-infected cell; or a monolayer-culture cell derived from various organisms.

As the organism, for example, a eukaryotic organism, a plant, or an animal (a mammalian animal, such as a human or a rat; a nematode; an insect, or the like) is included.

Transfection of Double-Stranded RNA into Cell or Organism

As a method for transfecting a double-stranded RNA bound with the compound (crosslinking agent) of the present invention into the cell or the organism as described above, a known method may be used. As the method mentioned above, for example, a calcium phosphate method, a DEAE-dextran method, electroporation and microinjection, a virus method, and a method using a cation liposome [such as Tfx50 (Promega) or LipofectAMINE 2000 (Life Technologies)] (Graham, F. L. and van der Eb, A. J. (1973) Virol. 52, 456, McCutchan, J. H. and Pagano, J. S. (1968) J. Natl. Cancer Inst. 41, 351, Chu, G et al., (1987) Nucl. Acids Res. 15, 1311, Fraley, R et al., (1980) J. Biol. Chem. 255, 10431, Capechi, M. R. (1980) Cell 22, 479, Felgner, P. L. et al., (1987), Proc. Natl. Acad. Sci. USA 84, 7413) can be used.

In accordance with the above known methods, the double-stranded RNA bound with the compound (crosslinking agent) of the present invention can be easily introduced (transfected) into a cell or an organism, and the above transfection can also be easily performed using a commercially available transfection kit.

In a cell or an organism into which the double-stranded RNA bound with the compound (crosslinking agent) of the present invention is transfected, by the compound (crosslinking agent) of the present invention, an inherent ability of the double-stranded RNA to mediate RNAi (ability to produce RNAi), that is, an ability (ability to decompose a target mRNA) to cause a phenomenon in which the expression of a target protein is specifically suppressed by the double-stranded RNA that promotes specific decomposition of a target mRNA complementary thereto, is suppressed, and as a result, a gene (target mRNA complementary to the double-stranded RNA) is expressed as if it is in a state similar to that in which the double-stranded RNA is not transfected (in a normal state).

3-3. Light Irradiation Step [Step (c)]

Next, a cell or an organism into which the double-stranded RNA bound with the compound (crosslinking agent) of the present invention is transfected is irradiated with light, so that the compound (crosslinking agent) of the present invention is eliminated from the double-stranded RNA bound with the compound (crosslinking agent) of the present invention.

That is, a gene-expression inhibitory effect (effect of decomposing a target mRNA complementary to the double-stranded RNA) of the double-stranded RNA, which is suppressed by the compound (crosslinking agent) of the present invention bound thereto, is restored by eliminating the compound (crosslinking agent) of the present invention from the double-stranded RNA by light irradiation, so that the expression of the gene (target mRNA) is suppressed.

(1) Light Irradiation

Light used in this case is similar to that described above, and an electromagnetic wave having a wavelength range of approximately 1 to 900 nm is used. In addition, light at a long wavelength side, for example, in the range of 350 to 400 nm is preferable, and a light having a wavelength of approximately 365±6 nm is more preferable.

In addition, the light irradiation time is also similar to that described above, and in particular, for example, the lower limit of the time using light of 4 mJ/cm$^2$s is 1 minute or more, and the upper limit is generally 10 minutes or less or preferably 3 minutes or less. Alternatively, the lower limit of the time using light of 376 mJ/cm$^2$s may be generally 0.1 seconds or more or preferably 1 second or more, and the upper limit may be generally 30 seconds or less or preferably 10 seconds or less. When the irradiation time is long, mutation may be induced in the double-stranded RNA, or a cell or an organism into which the double-stranded RNA crosslinked by the compound (crosslinking agent) of the present invention is transfected may be damaged, and on the other side, when the irradiation time is short, the compound (crosslinking agent) of the present invention may not be sufficiently eliminated in some cases; hence, attention must be paid.

The light irradiation may be performed on all (entire) of a cell or an organism into which the double-stranded RNA bound with the compound (crosslinking agent) of the present invention is infected or may be performed on a part thereof When a part or all (entire) of a cell or an organism into which the double-stranded RNA bound with the compound (crosslinking agent) of the present invention is transfected is irradiated with light, the expression of all (entire) gene of the cell or the organism or the expression of a gene located at the part thereof can be suppressed.

When all (entire) of the cell or the organism is irradiated with light, the cell or the organism may be placed to face a light source, or light irradiation means (such as UV light irradiation means including a mercury lamp and the like). Accordingly, the expression of an object gene (target gene) can be suppressed in the entire cell or organism into which the double-stranded RNA bound with the compound (crosslinking agent) of the present invention is transfected.

In addition, when a part of the cell or the organism is irradiated with light, light emitted from a light source or light irradiation means (such as UV light irradiation means including a mercury lamp and the like) is shaped into spot light by using an optical system including an objective lens and the like, and this spot light may be irradiated on a predetermined region of the cell or the organism. Accordingly, the expression of an object gene (target gene) can be suppressed only in the predetermined region of the cell or the organism into which the double-stranded RNA bound with the compound (crosslinking agent) of the present invention is transfected.

As described above, when the steps (a) to (c) of the present invention are performed, the expression of a specific gene (target mRNA) can be regulated (controlled) at an arbitrary timing and location.

That is, even when the double-stranded RNA bound with the compound (crosslinking agent) of the present invention is present in a cell or an organism, the expression of a target mRNA (target gene) complementary to the double-stranded RNA is not suppressed, and when light is then irradiated at a desired timing and/or on a desired location, the expression of the gene can be specifically suppressed.

After light irradiation, when the cell or the organism into which the double-stranded RNA bound with the compound (crosslinking agent) of the present invention is transfected is cultured or grown under appropriate conditions in which the cell or the organism can be grown in accordance with a common method so as to express a gene in the cell or the organism, the expression of a specific gene (target mRNA) is suppressed by an RNAi effect generated in the cell or the organism by the double-stranded RNA from which the compound (crosslinking agent) of the present invention is eliminated by the light irradiation.

Hence, the gene-expression regulation method including the steps (a) to (c) of the present invention preferably further includes, after the step (c), a step (c') of expressing a gene in the light-irradiated cell or organism.

4. Method for Examining Gene Function

In the method as described above, when the expression of a gene of a cell or an organism into which a double-stranded RNA bound with the compound (crosslinking agent) of the present invention is transfected is compared before and after light irradiation, for example, function analysis, specification, and identification of the gene can be performed.

Hence, the method for examining a gene function of the present invention includes: a step (a) of contacting a double-stranded RNA with the compound (crosslinking agent) of the present invention to crosslink the double-stranded RNA; a step (b) of transfecting the crosslinked double-stranded RNA into a cell or an organism; a step (c) of irradiating the transfected cell or organism with light; a step (c') of expressing a gene of the light-irradiated cell or organism; and a step (d) of comparing the gene expressed in the step (c') with a control.

In the present invention, the control means the same gene as a gene (target gene), the expression of which is suppressed by an RNAi effect generated by the double-stranded RNA (double-stranded RNA from which the compound (crosslinking agent) of the present invention is eliminated by light irradiation) obtained by light irradiation of the crosslinked double-stranded RNA, that is, the control means the gene, in a cell or an organism having a target mRNA complementary to the double-stranded RNA, the expression of which is not substantially suppressed by the double-stranded RNA.

Examples of the control as described above are, for example, (i) a gene expressed in a cell or an organism which is transfected with the crosslinked double-stranded RNA and which is not irradiated with light (a gene expressed in a cell or an organism which is the same type as that transfected with the crosslinked double-stranded RNA and which is transfected with the crosslinked double-stranded RNA and is not irradiated with light, a gene which is in a cell or an organism to be irradiated with light and which is expressed in the cell or the organism before light irradiation, and the like), (ii) a gene expressed in a cell or an organism which is the same type as that transfected with the crosslinked double-stranded RNA and which is not transfected with the crosslinked double-stranded RNA, and (iii) a gene expressed in a part (region), which is not irradiated with light, of a cell or an organism which is transfected with the crosslinked double-stranded RNA and is to be irradiated with light.

The controls described above may be used alone or may be appropriately used in combination.

In the present invention, the comparison between the gene expressed in the step (c') and the control is performed, for example, by measuring and observing the increase and decrease (expression level) in expression or the presence or absence of expression of a target gene (target mRNA complementary to the double-stranded RNA); the increase and decrease (protein amount) in expression product (protein or the like) or the presence or absence of an expression product of a target gene (target mRNA); or the phenotype generated by expression of a target gene (target mRNA) in a cell or an organism into which the double-stranded RNA bound with the compound (crosslinking agent) of the present invention is transfected and in a cell or an organism of the control using known methods, and comparing the results thereof.

In addition, in the present invention, in order to express a gene, a cell or an organism into which the double-stranded RNA bound with the compound (crosslinking agent) of the present invention is transfected and/or a cell or an organism of the control may be cultured or grown under appropriate conditions in which the cell or the organism can be grown in accordance with a common method so as to express the gene of the cell or the organism.

The method for examining a gene function of the present invention includes, in particular, the following steps (a) to (d):

a step (a) of contacting a double-stranded RNA with the compound (crosslinking agent) of the present invention to crosslink the double-stranded RNA;

a step (b) of transfecting the crosslinked double-stranded RNA into cells or organisms;

a step (c) of irradiating a transfected cell or organism with light;

a step (c') of expressing a gene of the light-irradiated cell or organism; and a step (c") of expressing a gene of a transfected-cell or organism which is not irradiated with light; and a step (d) of comparing the gene expressed in the step (c') with the gene expressed in the step (c").

The cell or the organism irradiated with light in the step (c) may be the same [one (group) of cells or individuals] as the cell or the organism which is not irradiated with light in the step (c") or may be the same type (different cells or individuals) as that described above, and in general, they are the same type and are different cells or individuals.

As another concrete example, for example, a method includes the following steps (a) to (d):

a step (a) of contacting a double-stranded RNA with the compound (crosslinking agent) of the present invention to crosslink the double-stranded RNA;

a step (b) of transfecting the crosslinked double-stranded RNA into cells or organisms;

a step (b') of expressing a gene of a transfected cell or organism before light irradiation;

a step (c) of irradiating a transfected cell or organism with light;

a step (c') of expressing a gene of the light-irradiated cell or organism; and a step (d) of comparing the gene expressed in the step (b') with the gene expressed in the step (c').

In this case, the cell or the organism in the step (b') is the same [one (group) of cells or individuals] as the cell or the organism in the step (c').

As another concrete example, for example, a method includes the following steps (a) to (d):

a step (a) of contacting a double-stranded RNA with the compound (crosslinking agent) of the present invention to crosslink the double-stranded RNA;

a step (b) of transfecting the crosslinked double-stranded RNA into a cell or an organism;

a step (c) of irradiating the transfected cell or organism with light;

a step (c') of expressing a gene of the light-irradiated cell or organism; and a step (c") of expressing a gene of a cell or an organism which is not transfected with the crosslinked double-stranded RNA; and a step (d) of comparing the gene expressed in the step (c') with the gene expressed in the step (c").

In this case, the cell or the organism in the step (c") is the same type (different cell or individual) as the cell or the organism transfected with the crosslinked double-stranded RNA in the step (b), that is, they are the same type and are different cells or organisms.

In the methods described above, the compound (crosslinking agent) of the present invention, the double-stranded RNA, the contact method between the compound (crosslinking agent) of the present invention and the double-stranded RNA, the cell or the organism transfected with the crosslinked double-stranded RNA, the method for transfecting the crosslinked double-stranded RNA into the cell or the organism, the light irradiation method, the method for expressing a gene in the cell or the organism, and preferable embodiments and concrete examples thereof are similar to those described above.

In addition, as described above, also in the method for examining a gene function of the present invention, the light irradiation may be performed on all (entire) of the cell or the organism into which the double-stranded RNA bound with the compound (crosslinking agent) of the present invention is trasnfected or may be performed on a part thereof. When a part of the cell or the organism is irradiated with light, a gene function only in a predetermined region of the cell or the organism into which the double-stranded RNA bound with the compound (crosslinking agent) of the present invention is transfected can be examined.

As a concrete example in the case described above, for example, a method includes the following steps (a) to (d):

a step (a) of contacting a double-stranded RNA with the compound (crosslinking agent) of the present invention to crosslink the double-stranded RNA;

a step (b) of transfecting the crosslinked double-stranded RNA into cells or an organisms;

a step (c) of irradiating a predetermined region of a transfected cell or organism with light;

a step (c') of expressing a gene of the light-irradiated cell or organism; and a step (d) of comparing the gene in the region irradiated with light, which is expressed in the step (c'), with a gene in a region which is not irradiated with light.

The cells or the organisms belong to one (group) of cells or individuals.

5. Kit of the Present Invention

A kit of the present invention is used to perform the crosslinking method, the gene-expression regulation method, or the gene-function examination method of the present invention as described above.

The kit described above at least includes the compound (crosslinking agent) of the present invention described above, that is, includes preferably the compound represented by the general formula (1), more preferably the compound represented by the general formula (2), even more preferably compound represented by the general formula (6), particularly preferably the compound represented by the general formula (7), the compound represented by the general formula (8), or the compound represented by the general formula (9), and most preferably includes the compound represented by the general formula (7).

Preferable embodiments and concrete examples thereof are as described above.

Furthermore, the kit of the present invention may also include reagents besides that described above. As the reagents mentioned above, for example, a transfection reagent to transfect the double-stranded RNA into a cell or an organism is included; however, the reagents are not limited thereto.

In addition, the kit may also include, for example, an instruction book illustrating how to perform the crosslinking method, the gene-expression regulation method, or the gene-function examination method of the present invention described above. The "instruction book" described above indicates an instruction manual of the kit, attached documents, a pamphlet (leaflet), or the like in which the features, principle, operation procedure, and the like of the methods of the present invention are substantially described with accompanying drawings, tables, and the like.

The methods of the present invention have the following effects.

(1) When an mRNA (target mRNA) of a target gene having a known sequence is broken, the function of the gene can be examined, and hence function analysis of the target gene can be effectively performed.

(2) To search for an unknown gene (such as a disease-relating gene) and to narrow down a candidate target gene can be effectively performed.

(3) A rapid analysis of the function of a gene and its phenotype when the gene is not expressed can be performed.

(4) Development of a so-called RNAi medicine using RNAi can be performed for treatment of diseases.

In particular, according to the present invention, an RNAi medicine can be developed which is able to generate a tissue-specific or a position-specific beneficial effect.

The present invention will be described in detail with reference to examples and comparative examples; however, the present invention is not limited thereto.

EXAMPLES

Example 1

Synthesis of Glutaric acid bis(6-bromo-4-diazomethyl-2-oxo-2H-chromen-7-yl) ester) (Pentanedioic acid bis(6-bromo-4-diazomethyl-2-oxo-2H-chromen-7-yl) ester) (Compound 1 of the present invention)

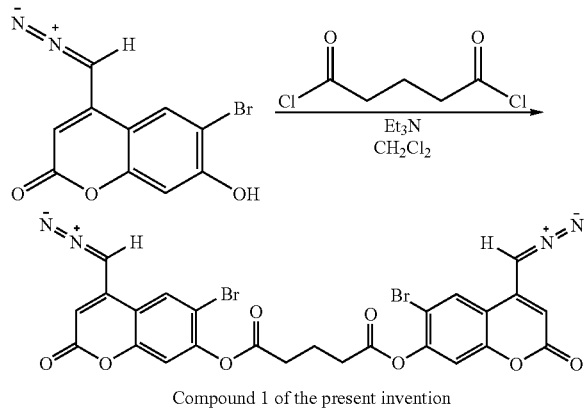

Compound 1 of the present invention

In an egg-plant flask of 10 ml, 24.9 mg (0.0898 mmol) of 6-bromo-7-hydroxy-4-diazomethylcoumarin, 1 ml of dichloromethane, 17.4 µl (0.1078 mmol) of triethylamine, and 5.726 µl (0.0449 mmol) of glutaric chloride were charged, followed by stirring at room temperature for 1 day. Subsequently, dilution was performed using chloroform, and an organic layer was washed with distilled water, so that the reaction was stopped. After drying was performed using magnesium sulfate, the solvent was removed, thereby obtaining a crude product of the compound 1 of the present invention (0.2753 mg, 0.0418 mmol, yield: 93%, yellow solid).

In this example, 6-bromo-7-hydroxy-4-diazomethylcoumarin was synthesized in accordance with the method described in International Publication Pamphlet WO00/31588.

$^1$H NMR (270 MHz, DMSO-d$_6$) δ 2.21 (2H, q, H3'), 2.89 (4H, t, 2H2', 2H4'), 6.00 (H, S, —CH═N), 6.73 (H, S, H3), 7.54 (H, S, H8), 8.23 (H, S, H5)

Example 2

Synthesis of Glutaric acid (6-bromo-4-diazomethyl-2-oxo-2H-chromen)-7-yl 2-[4-(6-bromo-4-diazomethyl-2-oxo-2H-chromen-7-yloxycarbonyl)butyryloxy]ethyl ester) (Pentanedioic acid (6-bromo-4-diazomethyl-2-oxo-2H-chromen)-7-yl 2-[4-(6-bromo-4-diazomethyl-2-oxo-2H-chromen-7-yloxycarbonyl)butyryloxy]ethyl ester) (Compound 2 of the present invention)

(1) Synthesis of Glutaric acid mono[2-(4-carboxybutyryloxy)ethyl]ester) (Pentanedioic acid mono[2-(4-carboxybutyryloxy)ethyl]ester) (Compound 1)

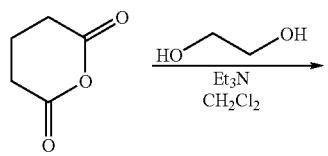

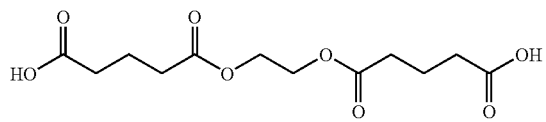

In an egg-plant flask of 50 ml, 2.5668 mg (22.496 mmol) of glutaric anhydride, 20 ml of dichloromethane, 564.5 µl (10.12 mmol) of ethylene glycol, and 3.245 µl (23.28 mmol) of triethylamine were sequentially charged and were stirred at room temperature for 2 hours, followed by stirring at 40° C. for 18.5 hours. Subsequently, 4.1907 g, 9.7724 g, and 1.4920 g of an ion-exchanged resin [manufactured by Dow Chemical Co., Dowex 1×2 (50-100 mesh)] were separately added three times. After the first addition, filtration was performed using dichloromethane, and after the second addition and the third addition, filtrations were performed using dichloromethane and methanol, respectively. Subsequently, the solvent was removed, thereby obtaining a crude product of the compound 1 (3.036 mg, 10.46 mmol, yield; 93% from $^1$HNMR).

$^1$H NMR (270 MHz, CDCl$_3$) δ 1.97 (4H, tt, 2H3', 2H10'), 2.43 (4H, t, 2H2', 2H11', J=7.3 Hz), 2.47 (4H, t, 2H4', 2H9', J=7.3 Hz), 4.31 (4H, S, 2H6', 2H7')

(2) Synthesis of 4-chlorocarbonylbutyric acid [2-(4-chlorocarbonylbutyryloxy)ethyl]ester (Compound 2)

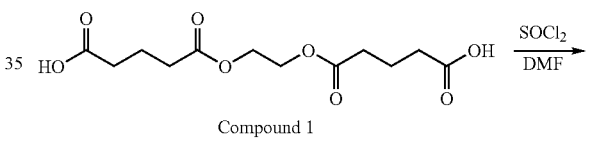

Compound 1

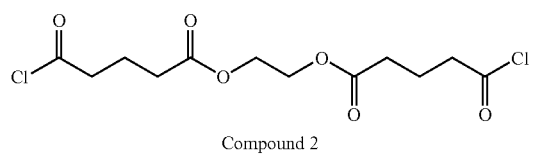

Compound 2

In an egg-plant flask of 100 ml, 268.8 mg (0.9260 mmol) of the compound 1 obtained by the above (1), 168.8 µl (2.3151 mmol) of thionyl chloride, and one droplet of DMF were charged, followed by stirring at 70 to 80° C. for 2 hours. Subsequently, thionyl chloride, DMF, and HCl were removed, thereby obtaining a crude product of the compound 2 from $^1$H NMR (296.9 mg, 0.9075 mmol, 98%, white solid).

$^1$H NMR (270 MHz, CDCl$_3$) δ 2.05 (4H, tt, 2H3', 2H10'), 2.45 (4H, t, 2H2', 2H11', J=7.3 Hz), 2.75 (4H, t, 2H4', 2H9', J=7.3 Hz), 4.31 (4H, S, 2H6', 2H7') Subsequently, thionyl chloride, DMF, and HCl were removed, thereby obtaining a crude product of the compound 2 from H NMR (296.9 g, 0.9075 mmol, 98%, white solid).

$^1$H NMR (270 MHz, CDCl$_3$) δ 2.05 (4H, tt, 2H3', 2H10'), 2.45 (4H, t, 2H2', 2H11', J=7.3 Hz), 2.75 (4H, t, 2H4', 2H9', J=7.3 Hz), 4.31 (4H, S, 2H6', 2H7')

(3) Synthesis of glutaric acid (6-bromo-4-diazomethyl-2-oxo-2H-chromen)-7-yl 2-[4-(6-bromo-4-diazomethyl-2-oxo-2H-chromen-7-yloxycarbonyl)butyryloxy]ethyl ester)

(Pentanedioic acid (6-bromo-4-diazomethyl-2-oxo-2H-chromen)-7-yl 2-[4-(6-bromo-4-diazomethyl-2-oxo-2H-chromen-7-yloxycarbonyl)butyryloxy]ethyl ester) (Compound 2 of the present invention)

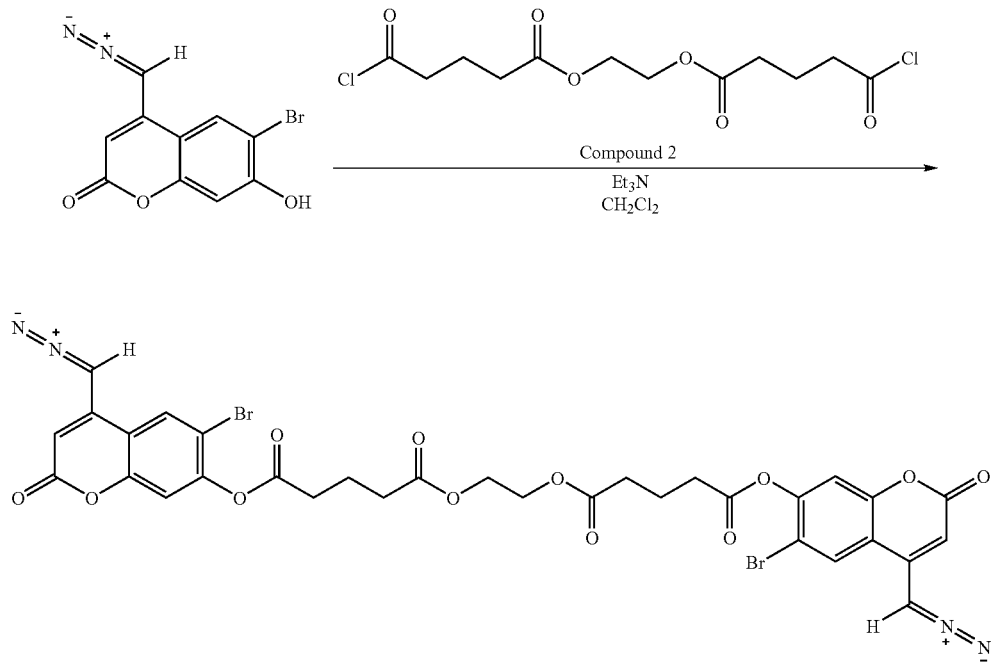

Compound 2 of the present invention

In an egg-plant flask of 10 ml, 61.6 mg (0.219 mmol) of 6-bromo-7-hydroxy-4-diazomethylcoumarin, and 3 ml of dichloromethane were charged. To this solution, 33.6 μl (0.241 mmol) of triethylamine, and 33.5 μg (0.0991 mmol) of the compound 2 obtained by the above (2) were charged, followed by stirring at room temperature for 1 day. Subsequently, dilution was performed using chloroform, and an organic layer was washed with distilled water, so that the reaction was stopped. After drying was performed using magnesium sulfate, the solvent was removed, thereby obtaining a crude product of the compound 2 of the present invention (82.4 mg, 0.101 mmol, yield: 92%, yellow solid).

In this example, 6-bromo-7-hydroxy-4-diazomethylcoumarin was synthesized in accordance with the method described in International Publication Pamphlet WO00/31588.

$^1$H NMR (270 MHz, DMSO-$d_6$) δ 2.05 (4H, tt, 2H3', 2H10'), 2.45 (4H, t, 2H2', 2H11', J=7.3 Hz), 2.75 (4H, t, 2H4', 2H9', J=7.3 Hz), 4.31 (4H, S, 2H6', 2H7'), 5.95 (H, S, —CH═N), 6.69 (H, S, H3), 7.45 (H, S, H8), 8.17 (H, S, H5)

Example 3

Synthesis of 3,3-dimethylglutaric acid (6-bromo-4-diazomethyl-2-oxo-2H-chromen)-7-yl 2-[4-(6-bromo-4-diazomethyl-2-oxo-2H-chromen-7-yloxycarbonyl)-3,3-dimethylbutyryloxy]ethyl ester) (3,3-dimethylpentanedioic acid (6-bromo-4-diazomethyl-2-oxo-2H-chromen)-7-yl 2-[4-(6-bromo-4-diazomethyl-2-oxo-2H-chromen-7-yloxycarbonyl)-3,3-dimethylbutyryloxy]ethyl ester) (Compound 3 of the present invention)

(1) Synthesis of 3,3-dimethylglutaric acid mono[2-(4-carboxy-3,3-dimethylbutyryloxy)ethyl]ester) (3,3-dimethylpentanedioic acid mono[2-(4-carboxy-3,3-dimethylbutyryloxy)ethyl]ester) (Compound 3)

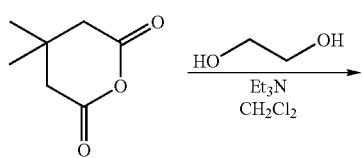

-continued

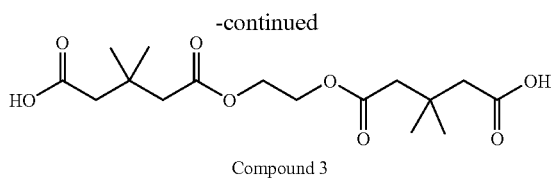

Compound 3

In an egg-plant flask of 50 ml, 4.3785 g (30.799 mmol) of glutaric anhydride, 20 ml of dichloromethane, 837.0 μl (15.00 mmol) of ethylene glycol, and 4.939 ml (35.42 mmol) of triethylamine were sequentially charged and were stirred at room temperature for 2 hours, followed by stirring at 40° C. for 24 hours. Subsequently, after the temperature was decreased to room temperature, 6 g of an ion-exchanged resin [manufactured by Dow Chemical Co., Dowex 1×2 (50-100 mesh)] was added, followed by filtration using dichloromethane. Next, the solvent was removed, thereby obtaining a crude product of the compound 3 (4.5085 g, 13.009 mmol, yield: 88% from HNMR).

$^1$H NMR (270 MHz, CDCl$_3$) δ=1.15 (12H, s, 3'-2CH$_3$, 10'-2CH$_3$), 2.48 (4H, s, 2H$_2$', 2H$_{11}$), 2.51 (4H, s, 2H$_4$', 2H$_9$'), 4.28 (4H, s, 2H$_6$', 2H$_7$')

(2) Synthesis of (4-chlorocarbonyl-3,3-dimethylbutyric acid [2-(4-chlorocarbonyl-3,3-dimethylbutyryloxy)ethyl]ester) (Compound 4)

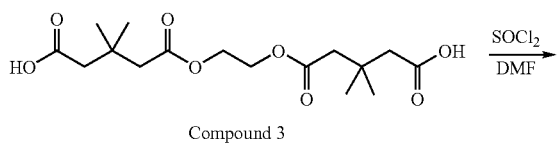

Compound 3

-continued

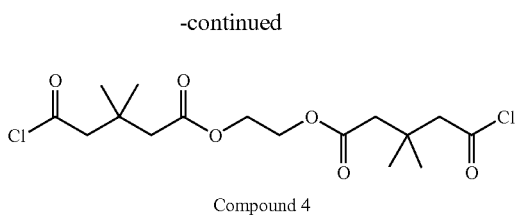

Compound 4

In an egg-plant flask of 100 ml, 299.7 mg (0.9260 mmol) of the compound 3 obtained by the above (1), 158 μl (2.3151 mmol) of thionyl chloride, and one droplet of DMF were charged, followed by stirring at 70 to 80° C. for 2 hours. Subsequently, thionyl chloride, DMF, and HCl were removed, thereby obtaining a crude product of the compound 4 (309.1 mg, 13.009 mmol, yield: 88% from H NMR).

$^1$H NMR (270 MHz, CDCl$_3$) δ=1.15 (12H, s, 3'-2CH3, 10'-2CH3), 2.47 (4H, s, 2H$_2$', 2H$_{11}$'), 3.15 (4H, s, 2H$_4$', 2H$_9$'), 4.29 (4H, s, 2H$_6$', 2H$_7$')

(3) Synthesis of 3,3-dimethylglutaric acid (6-bromo-4-diazomethyl-2-oxo-2H-chromen)-7-yl 2-[4-(6-bromo-4-diazomethyl-2-oxo-2H-chromen-7-yloxycarbonyl)-3,3-dimethylbutyryloxy]ethyl ester) (3,3-dimethylpentanedioic acid (6-bromo-4-diazomethyl-2-oxo-2H-chromen)-7-yl 2-[4-(6-bromo-4-diazomethyl-2-oxo-2H-chromen-7-yloxycarbonyl)-3,3-dimethylbutyryloxy]ethyl ester) (Compound 3 of the present invention)

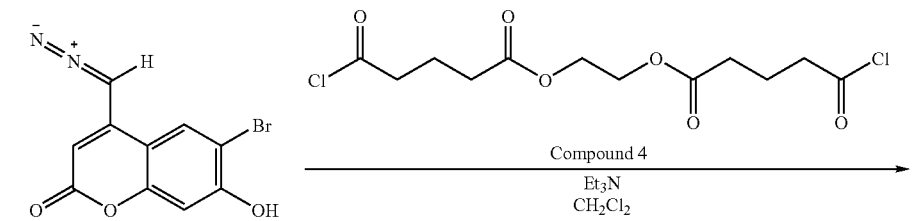

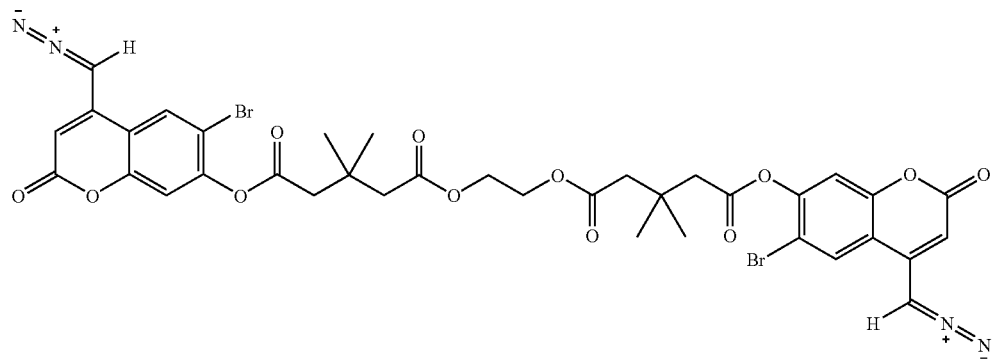

Compound 3 of the present invention

In an egg-plant flask of 10 ml, 28.27 mg (0.0737 mmol) of the compound 4 obtained by the above (2), 1 ml of dichloromethane, 33.9 µl (0.243 mmol) of triethylamine, and mg (0.2213 mmol) of 6-bromo-7-hydroxy-4-diazomethylcoumarin were charged, followed by stirring at 40° C. for 24 hours. Subsequently, after the temperature was decreased to room temperature, 1 ml of water was added, and extraction was performed alternately using chloroform and dichloromethane. After an organic layer was dried by magnesium sulfate, the solvent was removed, thereby obtaining a crude product of the compound 3 of the present invention (55.5 mg, 0.0636 mmol, yield: 87% from H NMR).

In this example, 6-bromo-7-hydroxy-4-diazomethylcoumarin was synthesized in accordance with the method described in International Publication Pamphlet WO00/31588.

$^1$H NMR (270 MHz DMSO) δ=1.08 (12H, s, 3'-2CH$_3$ and 10'-2CH$_3$), 2.68 (4H, s, H$_2$, and H$_{11'}$), 3.22 (4H, s, H$_{4'}$ and H$_{9'}$), 4.19 (4H, s, H$_{6'}$ and H$_{7'}$), 5.85 (H, s, —CH=N), 6.60 (H, s, H$_3$), 7.30 (H, s, H$_8$), 8.06 (H, s, H$_5$)

Example 4

Crosslinking of Double-Stranded RNA by Compound of the Present Invention

It was confirmed whether the compound of the present invention crosslinked a double-stranded RNA.

(1) Crosslinking Agent Solution

The compound 3 of the present invention obtained in Example 3 was dissolved in a DMSO solution to form a crosslinking agent solution at a concentration of 21.1 µM.

(2) Sample

The crosslinking agent solution or DMSO was mixed with an siRNA (double-stranded RNA) solution (TE buffer solution containing siRNA at a concentration of 20 µM) to form samples having compositions shown in the following Table 1, and samples thus formed were still held for 8 hours under light shielding conditions. Among the samples described above, sample Nos. 5 and 6 were irradiated with UV (350 nm) for 3 minutes using Rayonet Photochemical Reactor manufactured by Southern N. E. Ultraviolet Co.

Subsequently, 2 µl of formamide at a concentration of 5% was added to each sample, and sample Nos. 2, 4, and 6 were heated at 65° C. for 15 minutes and were then still held in ice for 10 minutes.

In this case, as the siRNA, a 22-bp double-stranded RNA (manufactured by QIAGEN) targeting GFP and having the following base sequence was used.

5'-GCAAGCUGACCCUGAAGUUCAU-3'

3'-GCCGUUCGACUGGGACUUCAAG-5'

TABLE 1

|   | siRNA | DMSO | Crosslinking agent solution | UV irradiation | Heating |
|---|---|---|---|---|---|
| 1 | 0.5 µl | 9.5 µl | — | − | − |
| 2 | 0.5 µl | 9.5 µl | — | − | + |
| 3 | 0.5 µl | — | 9.5 µl | − | − |
| 4 | 0.5 µl | — | 9.5 µl | − | + |
| 5 | 0.5 µl | — | 9.5 µl | + | − |
| 6 | 0.5 µl | — | 9.5 µl | + | + |

(3) Electrophoresis

After 2 µl of a sample buffer (prepared by mixing 3 ml of glycerin, 0.1 ml of 0.5 M EDTA-HCl aqueous solution (pH 8.0), and 6.9 ml of purified water) was added to each sample obtained by the above (2), followed by mixing, electrophoresis was performed at 7 mA (constant current) for 1 hour by a MODEL BE-211 electrophoresis apparatus manufactured by BIO CRAFT Co., Ltd using a 20% polyacrylamide gel and a ×1 TBE buffer.

Subsequently, the gel described above was dyed with SYBR GOLD (manufactured by Molecular Probes Inc.) and was then observed using Transilluminator (manufactured by Funakoshi Co., Ltd.).

(4) Results

The results are shown in FIG. 1. In the figure, Lane No. 1 shows the result obtained when sample No. 6 was used, Lane No. 2 shows the result obtained when sample No. 4 was used, Lane No. 3 shows the result obtained when sample No. 5 was used, Lane No. 4 shows the result obtained when sample No. 3 was used, Lane No. 5 shows the result obtained when sample No. 2 was used, and Lane No. 6 shows the result obtained when sample No. 1 was used. In the figure, [dsRNA→] indicates a migration position of a double-stranded RNA, and [ssRNA→] indicates a migration position of a single-stranded RNA.

As is clear from FIG. 1, it was found that from the results of Lane Nos. 5 and 6, a double-stranded RNA (siRNA) (Lane No. 5: sample No. 2) which did not react with the compound (crosslinking agent) of the present invention could not withstand thermal denaturation and was dissociated into single strands. On the other hand, it was found that although being thermally denaturated, a double-stranded RNA (Lane No. 2: sample No. 4) which reacted with the compound (crosslinking agent) of the present invention maintained its double-stranded structure when it was not irradiated with UV, and that a double-stranded RNA (Lane No. 1: sample No. 6), which reacted with the compound (crosslinking agent) of the present invention, was then irradiated with UV, and was further heated, was dissociated into single strands.

From the results described above, it was apparent that the compound (crosslinking agent) of the present invention crosslinked a double-stranded RNA (siRNA) and that the crosslinking was removed by UV irradiation, and it was also found that by this crosslinking, the thermal stability of a double-stranded RNA could be enhanced.

Example 5

Confirmation of RNAi-Effect Inhibitory Ability of Compound of the Present Invention (1) Reagents Hela cells (American Type Culture Collection (ATCC, Rockville, Md.))

DMEM culture medium (Dullbecco's modified Eagle culture medium, Nissui 2, manufactured by Nissui Pharmaceutical Co., Ltd.)

Opti-MEM culture medium (manufactured by GIBCO)

Trypsin solution (0.38 mg/ml EDTA aqueous solution containing 2.5 mg of trypsin, manufactured by GIBCO)

LipofectAMINE 2000 (manufactured by Invitrogen)

pEGFP-N1 vector solution

A solution was used which was prepared by dissolving a pEGFP-N1 vector (BD Living colors, manufactured by CLONTEC Laboratories, Inc.) in a TE buffer solution to obtain a concentration of 1,714 µg/ml.

pDsRed2-N1 vector solution

A solution was used which was prepared by dissolving a pDsRed2-N1 vector (BD Living colors, manufactured by CLONTEC Laboratories, Inc.) in a TE buffer solution to obtain a concentration of 1,612 µg/ml.

siRNA solution

A solution was used which was prepared by dissolving a double-stranded RNA (targeting an EGFP gene) having the following sequence in water to obtain a concentration of 200 nM.

5'-GCAAGCUGACCCUGAAGUUCAU-3'

3'-GCCGUUCGACUGGGACUUCAAG-5'

Crosslinking agent solution

Solutions were used as crosslinking agent solutions which were prepared by dissolving the compounds 1 to 3 of the present invention obtained in Examples 1 to 3 in a DMSO solution to have a concentration of 4 μM.

(2) Preparation of Transfection Hela Cells

Hela cells (500 μl of the DMEM culture medium containing Hela cells and 10% of FBS) were spread on a 24-hole plate so as to obtain $3 \times 10^4$ cells/well. After 24 hours passed, the old culture medium was removed, and Hela cells were then washed with a PBS(−) solution. Subsequently, the PBS (−) solution was removed, and 500 μl of the DMEM culture medium containing 10% of FBS was added per one well. This was used as a transfection Hela cell plate.

(3) Preparation of Transfecting Sample i) Crosslinking of siRNA

As shown in the following Table 2, 0.2 μl of the crosslinking agent solution and 0.20 μl of the siRNA solution were mixed together, and the mixture thus obtained was still held for 8 hours under light shielding conditions. Subsequently, Nos. 2, 4, and 6 were irradiated with UV (350 nm) for 3 minutes using Rayonet Photochemical Reactor manufactured by Southern N. E. Ultraviolet Co.

TABLE 2

| | siRNA (200 nM) | Crosslinking agent solution (4 μM) | UV irradiation |
|---|---|---|---|
| 1 | 0.2 μl | Compound 3 of the invention: 0.2 μl | − |
| 2 | 0.2 μl | Compound 3 of the invention: 0.2 μl | + |
| 3 | 0.2 μl | Compound 2 of the invention: 0.2 μl | − |
| 4 | 0.2 μl | Compound 2 of the invention: 0.2 μl | + |
| 5 | 0.2 μl | Compound 1 of the invention: 0.2 μl | − |
| 6 | 0.2 μl | Compound 1 of the invention: 0.2 μl | + | ii) Preparation of Sample

As shown in the following Table 3, 90 μl of the Opti-MEM culture medium, 0.36 μl of a pEGFP vector solution, 0.60 μl of the pDsRed vector solution, and 0.40 μl of the reaction solution prepared by the above i) were mixed together, and the mixture was still held for 15 minutes, so that a transfecting sample was prepared.

In addition, instead of the reaction solution prepared by the above i), by using 0.20 μl of an siRNA solution (a double-stranded RNA which was not crosslinked by the compound of the present invention), a procedure similar to that described above was performed, so that a control sample was prepared.

In this case, 617 ng of pEGFP was contained in 0.36 μl of pEGFP vector solution, 985 ng of pDsRed was contained in 0.60 μl of pDsRed vector solution, and 62.6 μg of siRNA was contained in 0.20 μl of 200 nM siRNA solution.

TABLE 3

| | Opti-MEM (90 μl) | pEGFP (0.36 μl) | pDsRed (0.60 μl) | Crosslinking reaction solution (0.40 μl) | | UV irradiation |
|---|---|---|---|---|---|---|
| | | | | siRNA | Crosslinking agent | |
| a | + | + | + | − | − | − |
| b | + | + | + | + Only 200 mM siRNA solution (0.20 μl) is added. | − | − |
| c | + | + | + | + | + Compound 3 of the invention | − |
| d | + | + | + | + | + Compound 3 of the invention | + |
| e | + | + | + | + | + Compound 2 of the invention | − |
| f | + | + | + | + | + Compound 2 of the invention | + |
| g | + | + | + | + | + Compound 1 of the invention | − |
| h | + | + | + | + | + Compound 1 of the invention | + |

(4) Transfection

To 9.2 μl of the Opti-MEM culture medium, 0.8 μl of LipofectAMINE 2000 was added, and the culture medium thus processed was still held for 10 minutes.

Next, the above culture medium and the transfecting sample obtained by the above ii) were mixed together, and this mixture was still held for 20 minutes.

The mixture thus obtained was added to the transfection Hela cell plate prepared by the above (2) and was then cultured at 37° C. for 48 hours using a $CO_2$ incubator (Automatic $CO_2$ Incubators 5400, manufactured by NAPCO).

(5) Results

After the culture was performed, transmission images of cells, and fluorescent images of EGFP and DsRed were observed.

By using a Meta Morph Analysis software (manufactured by Meta Imaging Software), the total fluorescent areas of the respective EGFP and DsRed were measured, and the ratio of EGFP/DsRed was obtained.

Figure 2:
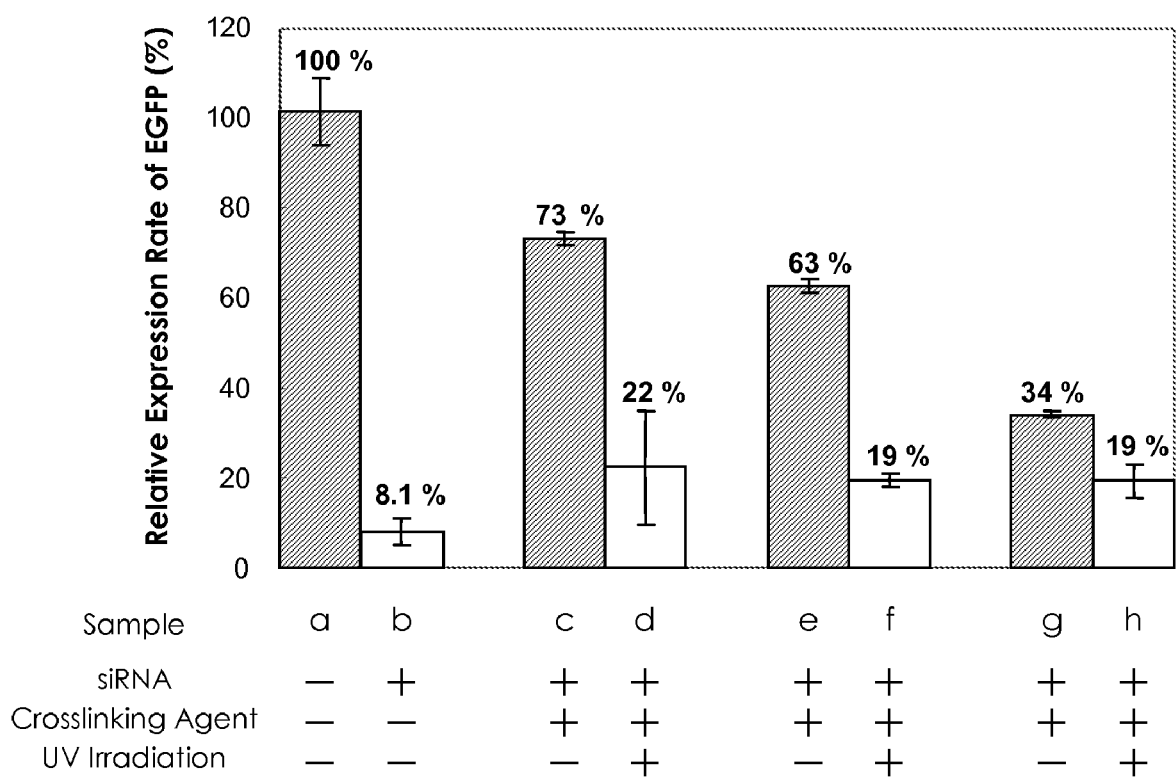
FIG. 2 is a graph showing relative EGFP expression levels of samples obtained in Example 5, the relative expression levels being obtained when an expression ratio by cotransfection of EGFP and DsRed is set to 100%.

The results are shown in FIG. 2.

In FIG. 2, the relative expression level of EGFP of each sample is shown which was obtained such that by using the above analysis software, areas of EGFP expressing cells and areas of DsRed expressing cells per predetermined area were counted, and the expression ratio was regarded as 100% when EGFP and DsRed were cotransfected.

As is clear from the results shown in FIG. 2, it was found that all the compounds of the present invention could inhibit the RNAi effect of siRNA when the compounds were bound thereto, and that the inhibited RNAi's suppression effect could be restored by UV irradiation. In addition, it was also found that among the compounds of the present invention, the compounds 2 and 3 of the present invention had a superior effect of inhibiting the RNAi effect, and the compound 3 of the present invention had a most superior effect.

Example 6

Study of Time for Reaction Between siRNA and Compound of the Present Invention (1) Reagents The same reagents as those used in Example 5 were used except that as the crosslinking agent solution, a solution was used which was prepared by dissolving the compound 3 of the present invention obtained in Example 3 in a DMSO solution to have a concentration of 4 μM.

(2) Preparation of Transfection Hela Cells

Preparation was performed by the same method as that in Example 5.

(3) Preparation of Transfecting Sample i) Crosslinking of siRNA

The crosslinking agent solution in an amount of 0.2 μl and the siRNA solution in an amount of 0.20 μl were mixed together, and the mixture thus formed was still held for 0, 1, 2, 4, 8, or 24 hours under light shielding conditions.

ii) Preparation of Sample

As shown in the following Table 4, 90 μl of the Opti-MEM culture medium, 0.36 μl of a pEGFP vector solution, 0.60 μl of the pDsRed vector solution, and 0.40 μl of the reaction solution prepared by the above i) were mixed together, and the mixture was still held for 15 minutes, so that a transfecting sample was prepared.

In addition, instead of the reaction solution prepared by the above i), by using 0.20 μl of an siRNA solution (a double-stranded RNA which was not crosslinked by the compound of the present invention), a procedure similar to that described above was performed, so that a control sample was prepared.

In this case, 617 ng of pEGFP was contained in 0.36 μl of pEGFP vector solution, 985 ng of pDsRed was contained in 0.60 μl of pDsRed vector solution, and 62.6 μg of siRNA was contained in 0.20 μl of 200 nM siRNA solution.

(4) Transfection

Transfection was performed in a manner similar to that in Example 5.

(5) Results

After the culture was performed, transmission images of cells, and fluorescent images of EGFP and DsRed were observed.

By using a Meta Morph Analysis software (manufactured by Meta Imaging Software), the total fluorescent areas of the respective EGFP and DsRed were measured, and the ratio of EGFP/DsRed was obtained.

Figure 3:
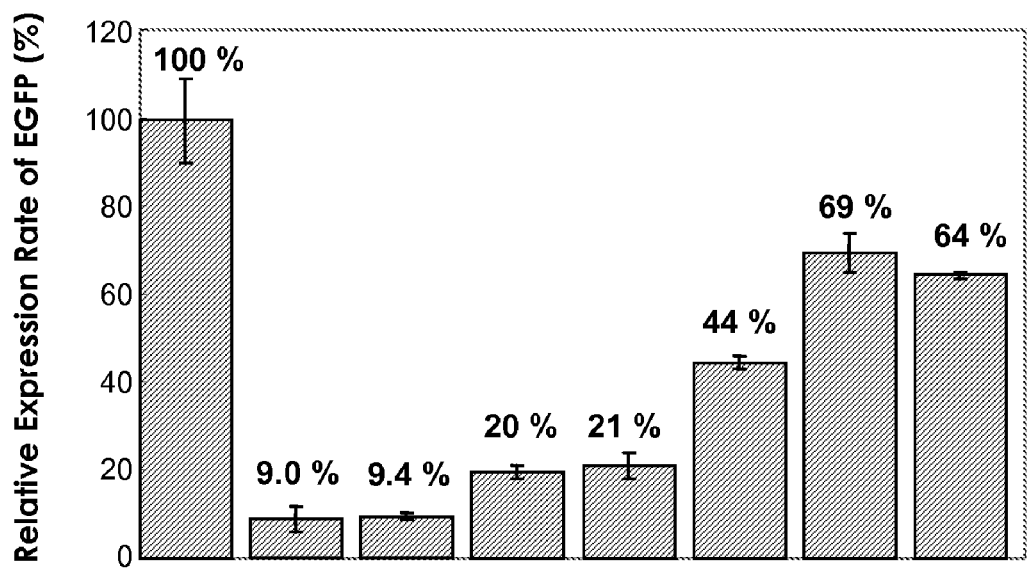
FIG. 3 is a graph showing relative EGFP expression levels of samples obtained in Example 6, the relative expression levels being obtained when an expression ratio by cotransfection of EGFP and DsRed is set to 100%.

The results are shown in FIG. 3.

In FIG. 3, the relative expression level of EGFP of each sample is shown which was obtained such that by using the above analysis software, areas of EGFP expressing cells and areas of DsRed expressing cells per predetermined area were counted, and the expression ratio was regarded as 100% when EGFP and DsRed were cotransfected.

As is clear from the results shown in FIG. 3, it was found that the expression of EGFP was suppressed to 9.0% by siRNA. In addition, it was also found that when the time for reaction between the compound 3 of the present invention and siRNA was short, since the reaction was not advanced, siRNA could not be sufficiently crosslinked, and in addition, that since a significant difference could not be observed between a reaction time of 8 hours and that of 24 hours, the reaction between the compound (crosslinking agent) of the present invention and siRNA reached a plateau at approximately 8 hours.

Example 7

Confirmation of Effectiveness of Compound of the Present Invention (1) Photodegradable Protective Group (a): Compound 3 of the present invention (b): 3,3-dimethylglutaric acid (6-bromo-4-methyl-2-oxo-2H-chromen)-7-yl 2-[4-(6-bromo-4-methyl-2-oxo-2H-chromen-7-yloxycarbonyl)-3,3-dimethylbutyryloxy]ethyl ester (3,3-Dimethylpentanedioic acid (6-bromo-4-methyl-2-oxo-2H-chromen)-7-yl 2-[4-(6-bromo-4-methyl-2-oxo-2H-chromen-7-yloxycarbonyl)-3,3-dimethylbutyryloxy]ethyl ester) (hereinafter abbreviated as "bis-Bhc-$CH_3$.")

TABLE 4

| | Opti-MEM (90 μl) | pEGFP (0.36 μl) | pDsRed (0.60 μl) | Crosslinking reaction solution (0.40 μl) | | |
| | | | | siRNA | Crosslinking agent | Reaction time |
|---|---|---|---|---|---|---|
| 1 | + | + | + | − | − | − |
| 2 | + | + | + | + Only 200 mM siRNA solution (0.20 μl) is added. | − | − |
| 3 | + | + | + | + | + | 0 hour |
| 4 | + | + | + | + | + | 1 hour |
| 5 | + | + | + | + | + | 2 hours |
| 6 | + | + | + | + | + | 4 hours |
| 7 | + | + | + | + | + | 8 hours |
| 8 | + | + | + | + | + | 24 hours |

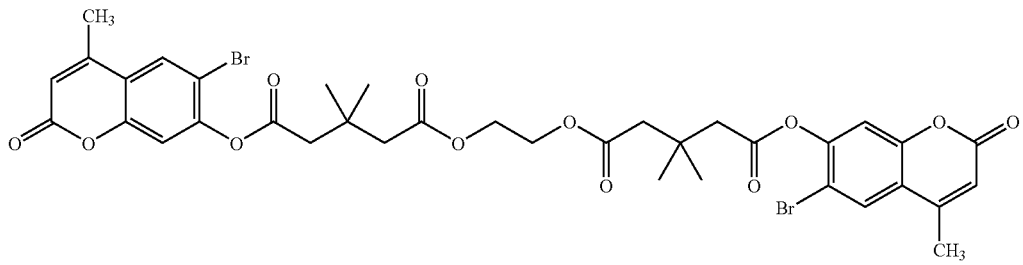

The synthesis was performed in accordance with the method in Example 3 except that 6-bromo-7-hydroxy-4-methylcumarine was used.

In this example, 6-bromo-7-hydroxy-4-methylcumarine was synthesized in accordance with the method described by T. Furuta, H. Takeuchi, M. Isozaki, Y. Takahashi, M. Sugimoto, M. Kanehara, T. Watanabe, K. Noguchi, T. M. Dore, M. Iwamura, R. Y. Tsien, Bhc-cNMPs as either water-soluble or membrane-permeant photo-releasable cyclic nucleotides for both one and two-photon excitation, ChemBioChem, 5, 1119-1128 (2004). $^1$H NMR (CD3OD) δ 2.13 (4 h, quintet, J=7.3 Hz), 2.41 (6H, s), 2.55 (4H, t, J=7.3 Hz), 2.76 (4H, t, J=7.3 Hz), 4.34 (4H, s), 6.29 (2H, s), 7.15 (2H, s), 7.81 (2H, s); $^{13}$C NMR (DMSO-d6) δ 18.65 (q), 19.75 (t), 32.81 (t), 32.95 (t), 62.24 (t), 111.56 (s), 112.57 (d), 115.46 (d), 119.45 (d), 150.17 (s), (s), 153.02 (s), 159.68 (s), 169.92 (s), 172.43 (s); IR (ATR) 2953, 1770, 1727, 1396, 1384, 1360, 1147, 1114

(c): 6-bromo-7-hydroxy-4-methyldiazocumarine (hereinafter abbreviated as "Bhc-diazo.")

Synthesis was performed in accordance with the method described in International Publication Pamphlet WO00/31588.

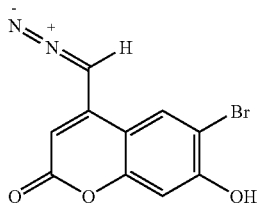

(2) Reagents

The same reagents as those used in Example 5 were used except that the following were used as the crosslinking agent solutions.

Crosslinking agent solution containing the compound 3 of the present invention

A solution was used which was prepared by dissolving the compound 3 of the present invention obtained in Example 3 in a DMSO solution to have a concentration of 4 μM.

Crosslinking agent solution containing bis-Bhc-CH$_3$

A solution was used which was prepared by dissolving bis-Bhc-CH$_3$ in a DMSO solution to have a concentration of 4 μM.

Crosslinking agent solution containing Bhc-diazo

A solution was used which was prepared by dissolving Bhc-diazo in a DMSO solution to have a concentration of 8 NM.

(3) Preparation of Transfection Hela Cells

Preparation was performed by the same method as that in Example 5.

(4) Preparation of Transfecting Sample i) Crosslinking of siRNA

As shown in the following Table 5, 0.2 μl of the crosslinking agent solution and 0.20 μl of the siRNA solution were mixed together, and the mixture thus obtained was still held for 8 hours under light shielding conditions. Subsequently, Nos. 2, 4, and 6 were irradiated with UV (350 nm) for 3 minutes using Rayonet Photochemical Reactor manufactured by Southern N. E. Ultraviolet Co.

TABLE 5

| | siRNA (200 nM) | Crosslinking agent solution (4 μM) | UV irradiation |
|---|---|---|---|
| 1 | 0.2 μl | Compound 3 of the invention (4 μM): 0.2 μl | − |
| 2 | 0.2 μl | Compound 3 of the invention (4 μM): 0.2 μl | + |
| 3 | 0.2 μl | bis-Bhc-CH$_3$ (4 μM): 0.2 μl | − |
| 4 | 0.2 μl | bis-Bhc-CH$_3$ (4 μM): 0.2 μl | + |
| 5 | 0.2 μl | Bhc-diazo (8 μM): 0.2 μl | − |
| 6 | 0.2 μl | Bhc-diazo (8 μM): 0.2 μl | + | ii) Preparation of Sample

As shown in the following Table 6, 90 μl of the Opti-MEM culture medium, 0.36 μl of a pEGFP vector solution, 0.60 μl of the pDsRed vector solution, and 0.40 μl of the reaction solution prepared by the above i) were mixed together, and the mixture thus formed was still held for 15 minutes, so that a transfecting sample was prepared.

In addition, instead of the reaction solution prepared by the above i), by using 0.20 μl of an siRNA solution (a double-stranded RNA which was not crosslinked by the compound of the present invention), a procedure similar to that described above was performed, so that a control sample was prepared.

In this case, 617 ng of pEGFP was contained in 0.36 μl of pEGFP vector solution, 985 ng of pDsRed was contained in 0.60 μl of pDsRed vector solution, and 62.6 μg of siRNA was contained in 0.20 μl of 200 nM siRNA solution.

TABLE 6

| | Opti-MEM (90 μl) | pEGFP (0.36 μl) | pDsRed (0.60 μl) | Crosslinking reaction solution (0.40 μl) | | UV irradiation |
| | | | | siRNA | Crosslinking agent | |
|---|---|---|---|---|---|---|
| a | + | + | + | − | − | − |
| b | + | + | + | + Only 200 mM siRNA solution (0.20 μl) is added. | − | − |
| c | + | + | + | + | + Compound 3 of the invention | − |
| d | + | + | + | + | + Compound 3 of the invention | + |
| e | + | + | + | + | + bis-Bhc-CH₃ | − |
| f | + | + | + | + | + bis-Bhc-CH₃ | + |
| g | + | + | + | + | + Bhc-diazo | − |
| h | + | + | + | + | + Bhc-diazo | + |

(5) Transfection

Transfection was performed in a manner similar to that in Example 5.

(5) Results

After the culture was performed, transmission images of cells, and fluorescent images of EGFP and DsRed were observed.

By using a Meta Morph Analysis software (manufactured by Meta Imaging Software), the total fluorescent areas of the respective EGFP and DsRed were measured, and the ratio of EGFP/DsRed was obtained.

Figure 4:
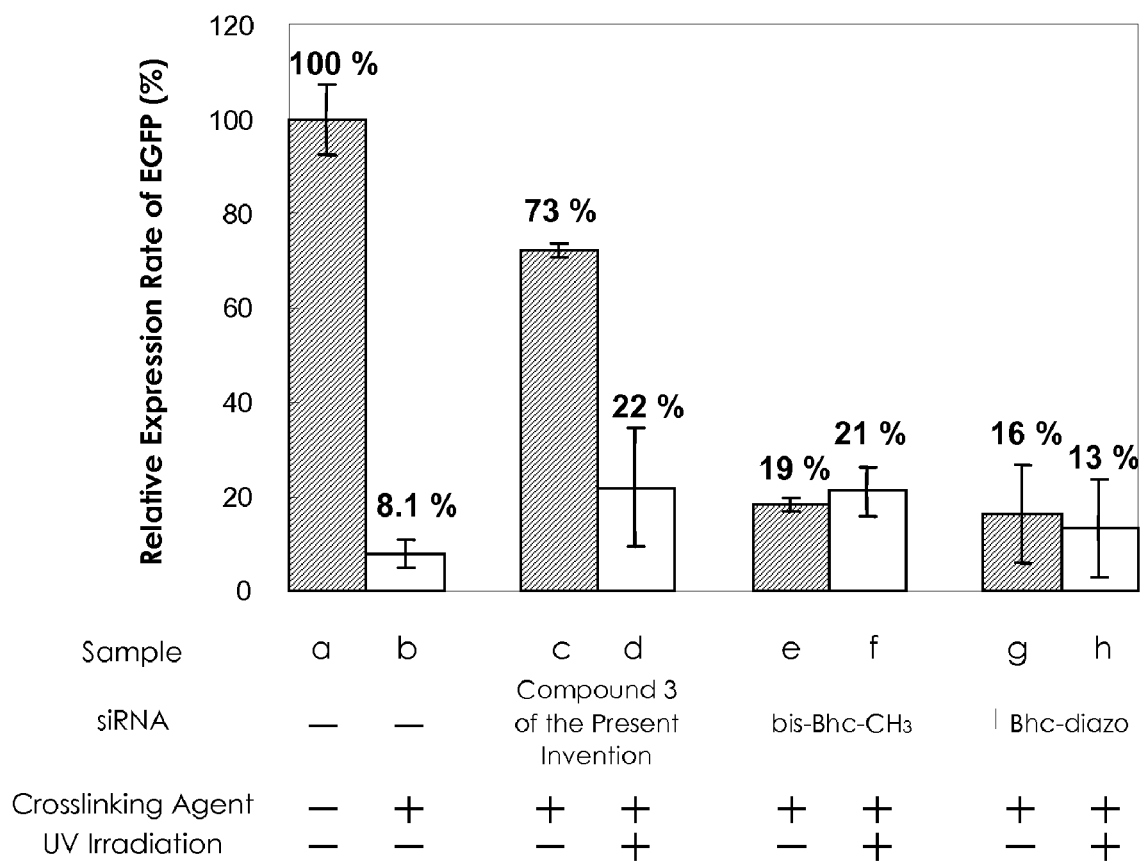
FIG. 4 is a graph showing relative EGFP expression levels of samples obtained in Example 7, the relative expression levels being obtained when an expression ratio by cotransfection of EGFP and DsRed is set to 100%.

The results are shown in FIG. 4.

In FIG. 4, the relative expression level of EGFP of each sample is shown which was obtained such that by using the above analysis software, areas of EGFP expressing cells and areas of DsRed expressing cells per predetermined area were counted, and the expression ratio was regarded as 100% when EGFP and DsRed were cotransfected.

As is clear from the results shown in FIG. 4, it was found that when UV irradiation was not performed, the compound 3 of the present invention could inhibit the siRNA effect, and that the inhibition was broken down by UV irradiation. On the other hand, since having a methyl group instead of an azo group that could form a covalent bond with siRNA, bis-Bhc-CH₃ could not be bound to siRNA, and hence regardless before and after UV irradiation, the siRNA effect could be hardly inhibited. In addition, it was also found that although Bhc-diazo had an azo group that could form a covalent bond with siRNA, since having no linker portion, Bhc-diazo could not crosslink two chains of siRNA, and hence the siRNA effect could be hardly inhibited.

Accordingly, it was found that in order to inhibit the siRNA effect, it is important that the two photodegradable protective groups have groups bindable to a double-stranded RNA and be disposed at two ends of the linker portion so as to be able to crosslink the double-stranded RNA.

Example 8

Study in Cell (1) Reagents

The same reagents as those used in Example 6 were used.

(2) Preparation of Transfection Hela Cells

Hela cells (500 μl of DMEM containing Hela cells and 10% of FBS) were spread on a 24-hole plate so as to obtain 5×10³ cells/well. After 24 hours passed, the old culture medium was removed, and Hela cells were washed with a PBS(−) solution. Subsequently, the PBS(−) solution was removed, and 500 μl of DMEM containing 10% of FBS was added per one well. This was used as a transfection Hela cell plate.

(3) Preparation of Transfecting Sample i) Crosslinking of siRNA

The crosslinking agent solution in an amount of 0.2 μl and the siRNA solution in an amount of 0.20 μl were mixed together, and the mixture thus obtained was still held for 8 hours under light shielding conditions.

ii) Preparation of Sample

As shown in the following Table 7, 90 μl of the Opti-MEM culture medium, 0.36 μl of a pEGFP vector solution, 0.60 μl of the pDsRed vector solution, and 0.40 μl of the reaction solution prepared by the above i) were mixed together, and the mixture thus formed was still held for 15 minutes, so that a transfecting sample was prepared.

In addition, instead of the reaction solution prepared by the above i), by using 0.20 μl of an siRNA solution (a double-stranded RNA which was not crosslinked by the compound of the present invention), a procedure similar to that described above was performed, so that a control sample was prepared.

In this case, 617 ng of pEGFP was contained in 0.36 μl of pEGFP vector solution, 985 ng of pDsRed was contained in 0.60 μl of pDsRed vector solution, and 62.6 μg of siRNA was contained in 0.20 μl of 200 nM siRNA solution.

TABLE 7

| | Opti-MEM (90 μl) | pEGFP (0.36 μl) | pDsRed (0.60 μl) | Crosslinking reaction solution (0.40 μl) | |
| | | | | siRNA | Crosslinking agent |
|---|---|---|---|---|---|
| 1 | + | + | + | − | − |
| 2 | + | + | + | + Only 200 mM siRNA solution (0.20 μl) is added. | − |
| 3 | + | + | + | + | + |

(4) Transfection

To 9.2 μl of the Opti-MEM culture medium, 0.8 μl of LipofectAMINE 2000 was added, and the culture medium thus processed was still held for 10 minutes.

Next, the above culture medium and the transfecting sample obtained by the above ii) were mixed together, and this mixture was still held for 20 minutes.

The mixture thus obtained was added to the transfection Hela cell plate prepared by the above (2) and was then cultured at 37° C. for 6 hours using a $CO_2$ incubator (Automatic $CO_2$ Incubators 5400, manufactured by NAPCO).

(5) UV Irradiation

After the culture was performed, the culture medium was removed, and Hela cells were washed with a PBS(−) solution. Subsequently, the PBS(−) solution was removed, and 500 μl of the Opti-MEM culture medium was added per one well. Next, the center of the well was irradiated with UV (335 to 385 nm) for 1 second using an inverted system fluorescent microscope IX71 (objective lens: UPLAPO×10) manufactured by Olympus Corp.

After the UV irradiation, the Opti-MEM culture medium was removed, and 500 μl of DMEM containing 10% of FBS was added per one well and was then cultured at 37° C. for 42 hours using a $CO_2$ incubator (Automatic $CO_2$ Incubators 5400, manufactured by NAPCO).

(6) Results

After the culture was performed, transmission images of cells, and fluorescent images of EGFP and DsRed were observed.

By using a Meta Morph Analysis software (manufactured by Meta Imaging Software), the total fluorescent areas of the respective EGFP and DsRed were measured, and the ratio of EGFP/DsRed was obtained.

Figure 5:
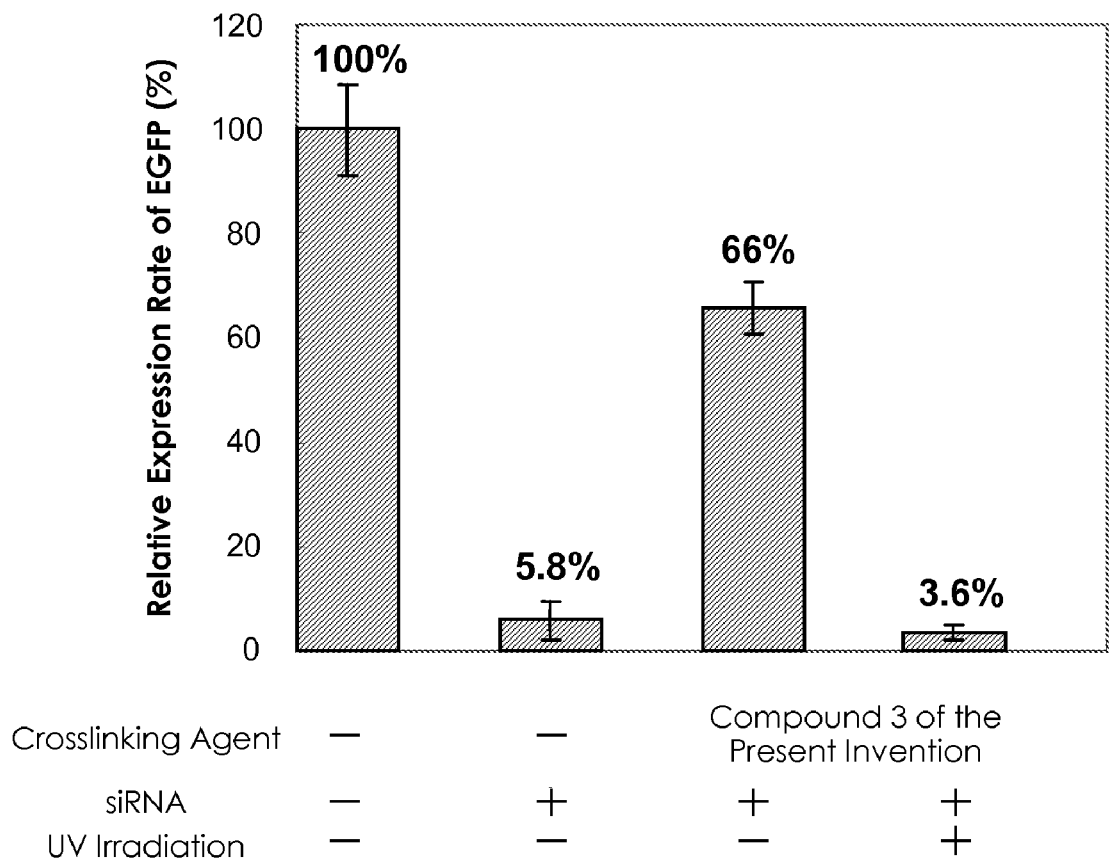
FIG. 5 is a graph showing relative EGFP expression levels of samples obtained in Example 8, the relative expression levels being obtained when an expression ratio by cotransfection of EGFP and DsRed is set to 100%.

The results are shown in FIG. 5.

In FIG. 5, the relative expression level of EGFP of each sample is shown which was obtained such that by using the above analysis software, areas of EGFP expressing cells and areas of DsRed expressing cells per predetermined area were counted, and the expression ratio was regarded as 100% when EGFP and DsRed were cotransfected.

Figure 6:
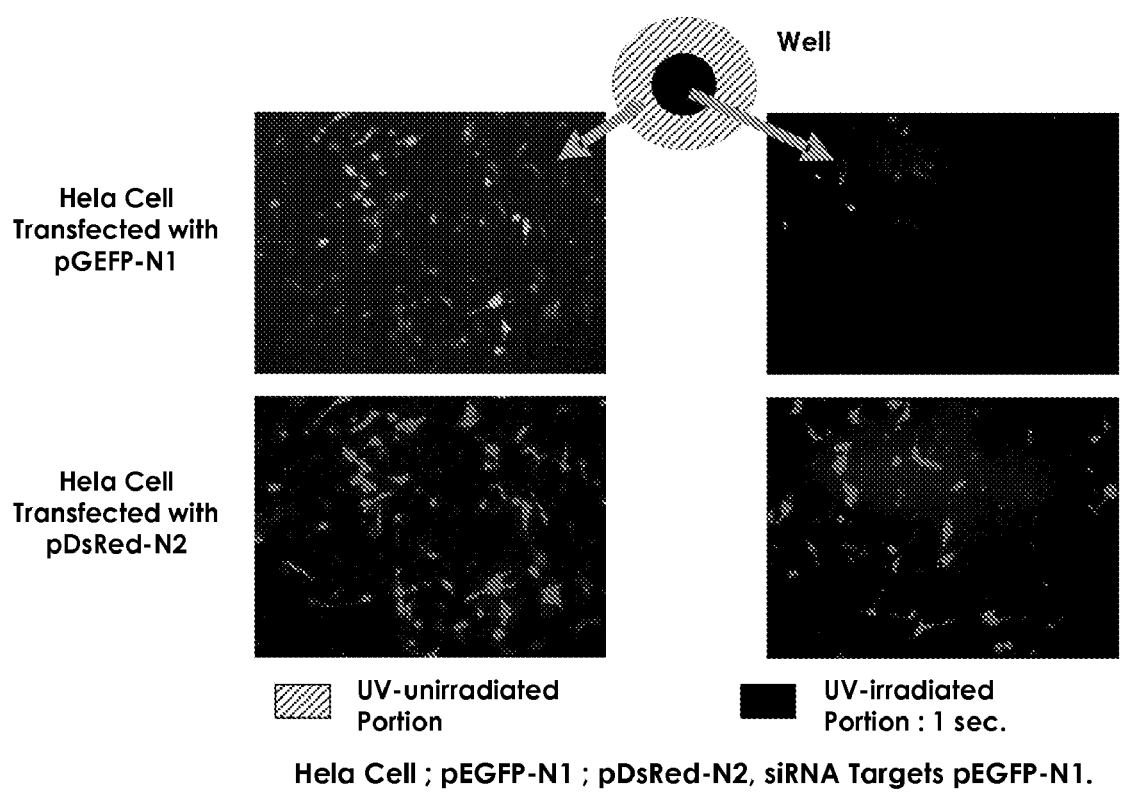
FIG. 6 shows the results of observation of fluorescent images of EGFP and DsRed in cells, which are obtained in Example 8.

In addition, the observation results of the fluorescence images of EGFP and DsRed obtained by using the compound 3 of the present invention are shown in FIG. 6.

As is clear from the results shown in FIGS. 5 and 6, it was found that at a portion which was not irradiated with UV, crosslinking of siRNA by the compound 3 of the present invention could not be removed, and the RNAi effect of siRNA was inhibited, and that on the other hand, at a portion which was irradiated with UV, the crosslinking of siRNA by the compound 3 of the present invention was removed, and the RNAi effect of siRNA was restored.

Accordingly, it was found that when irradiation was locally performed by decreasing a UV irradiation area, crosslinking of siRNA by the compound of the present invention could be specifically removed at an arbitrary location, that is, the expression of a gene could be specifically suppressed at an arbitrary location.

Example 9

Confirmation of Influences of Light Irradiation and the Compound (Crosslinking Agent) of the Present Invention on RNAi The expression level obtained by transfection of siRNA which reacted with the compound of the present invention was low as that obtained by transfection of only EGFP. In order to investigate this reason, it was confirmed whether the transfection efficiency was degraded by the compound of the present invention or by the transfection itself of siRNA.

(1) Reagents

The same reagents as those used in Example 5 were used except that as the crosslinking agent solution, a solution was used which was prepared by dissolving the compound 3 of the present invention obtained in Example 3 in a DMSO solution to have a concentration of 4 μM, and that besides siRNA, as control siRNA, a control siRNA solution was used which was prepared by dissolving a double-stranded RNA (targeting luciferase) having the following sequence in water to have a concentration of 200 nM.

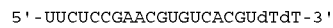

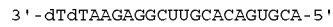

(2) Preparation of Transfection Hela Cells

Preparation was performed by the same method as that in Example 5.

(3) Preparation of Transfecting Sample i) Crosslinking of siRNA

As shown in the following Table 8, 0.2 μl of the crosslinking agent solution and 0.20 μl of the siRNA solution or 0.20 μl of the control siRNA solution were mixed together, and the mixture thus obtained was still held for 8 hours under light shielding conditions.

TABLE 8

| | siRNA (200 nM) | Control siRNA (200 nM) | Crosslinking agent solution (4 μM) |
|---|---|---|---|
| 1 | 0.2 μl | — | 0.2 μl |
| 2 | — | 0.2 μl | 0.2 μl | ii) Preparation of Sample

As shown in the following Table 9, 90 μl of the Opti-MEM culture medium, 0.36 μl of a pEGFP vector solution, 0.60 μl of the pDsRed vector solution, and 0.40 μl of the reaction solution prepared by the above i) were mixed together, and the mixture thus formed was still held for 15 minutes, so that a transfecting sample was prepared.

In addition, instead of the reaction solution prepared by the above i), by using 0.20 μl of an siRNA solution (a double-stranded RNA which was not crosslinked by the compound of the present invention) or 0.20 μl of the control siRNA solution (a double-stranded RNA which was not crosslinked by the compound of the present invention), a procedure similar to that described above was performed, so that a control sample was prepared.

In this case, 617 ng of pEGFP was contained in 0.36 μl of pEGFP vector solution, 985 ng of pDsRed was contained in 0.60 μl of pDsRed vector solution, and 62.6 μg of siRNA was contained in 0.20 μl of 200 nM siRNA solution.

TABLE 9

| | Opti-MEM (90 μl) | pEGFP (0.36 μl) | pDsRed (0.60 μl) | Transfecting sample (0.40 μl) | | Crosslinking agent |
| | | | | siRNA | Control siRNA | |
| --- | --- | --- | --- | --- | --- | --- |
| a | + | + | + | − | − | − |
| b | + | + | + | + Only 200 mM siRNA solution (0.20 μl) is added. | − | − |
| C | + | + | + | − | + Only 200 mM control siRNA solution (0.20 ml) is added. | − |
| d | + | + | + | + | − | + |
| e | + | + | + | + | − | + |
| f | + | + | + | − | + | + |
| g | + | + | + | − | + | + |

(4) Transfection

To 9.2 μl of the Opti-MEM culture medium, 0.8 μl of LipofectAMINE 2000 was added, and the culture medium thus processed was still held for 10 minutes.

Next, the above culture medium and the transfecting sample obtained by the above ii) or the control sample were mixed together, and this mixture was still held for 20 minutes.

The mixture thus obtained was added to the transfection Hela cell plate prepared by the above (2) and was then cultured at 37° C. for 6 hours using a $CO_2$ incubator (Automatic $CO_2$ Incubators 5400, manufactured by NAPCO).

(5) UV Irradiation

After the culture was performed, the culture medium was removed, and Hela cells were washed with a PBS(−) solution. Subsequently, the PBS(−) solution was removed, and 500 μl of the Opti-MEM culture medium was added per one well. Next, the well in which Hela cells transfected with a transfecting sample d were cultured and the well in which Hela cells transfected with a transfecting sample f were cultured were each irradiated with UV (335 to 385 nm) for 1 second using an inverted system fluorescent microscope IX71 (objective lens: UPLAPO×10) manufactured by Olympus Corp.

After the UV irradiation, the Opti-MEM culture medium was removed, and 500 μl of DMEM containing 10% of FBS was added per one well and was then cultured at 37° C. for 42 hours using a $CO_2$ incubator (Automatic $CO_2$ Incubators 5400, manufactured by NAPCO).

(6) Results

After the culture was performed, transmission images of cells, and fluorescent images of EGFP and DsRed were observed.

By using a Meta Morph Analysis software (manufactured by Meta Imaging Software), the total fluorescent areas of the respective EGFP and DsRed were measured, and the ratio of EGFP/DsRed was obtained.

Figure 7:
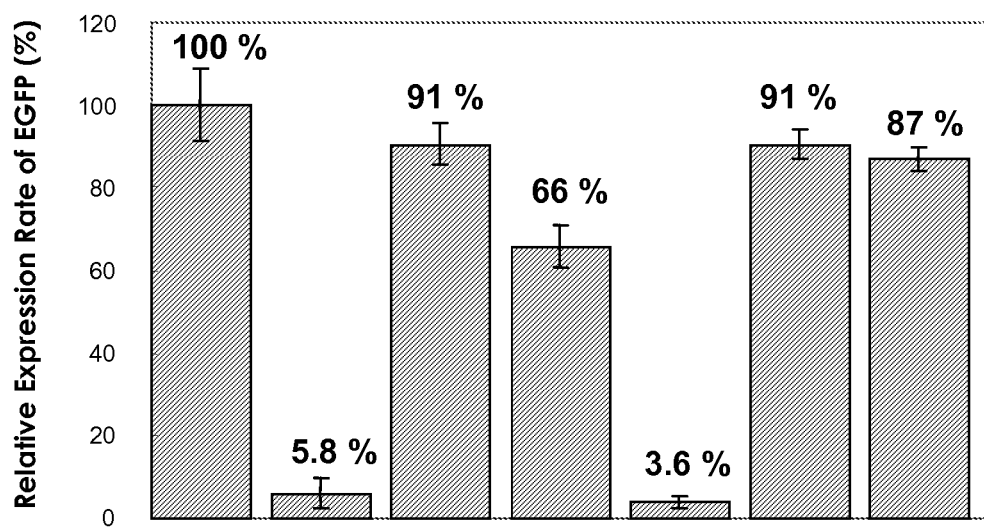
FIG. 7 is a graph showing relative EGFP expression levels of samples obtained in Example 9, the relative expression levels being obtained when an expression ratio by cotransfection of EGFP and DsRed is set to 100%.

The results are shown in FIG. 7.

In FIG. 7, the relative expression level of EGFP of each sample is shown which was obtained such that by using the above analysis software, areas of EGFP expressing cells and areas of DsRed expressing cells per predetermined area were counted, and the expression ratio was regarded as 100% when EGFP and DsRed were cotransfected.

As is clear from the results shown in FIG. 7, it was found that the expression rate obtained when the control siRNA was only transfected and the expression rate obtained when the control siRNA was crosslinked by the compound 3 of the present invention were approximately equivalent to each other. Accordingly, it was confirmed that the decrease in expression level was not caused by the degradation of the transfection efficiency by the compound of the present invention and the transfection itself of siRNA, that is, it was confirmed that siRNA specifically exhibited its effect, and that the transfection efficiency was not degraded by siRNA and further the compound of the present invention.

Example 10

Study of Light Irradiation Control of Endogenous Gene by the Compound 3 of the Present Invention (1) Reagents Hela cells (American Type Culture Collection (ATCC, Rockville, Md.)

DMEM culture medium (Dullbecco's modified Eagle culture medium, Nissui 2, manufactured by Nissui Pharmaceutical Co., Ltd.)

Opti-MEM culture medium (manufactured by GIBCO)

Trypsin solution (0.38 mg/ml EDTA aqueous solution containing 2.5 mg of trypsin, manufactured by GIBCO)

LipofectAMINE 2000 (manufactured by Invitrogen)

siRNA solution

A solution was used which was prepared by dissolving a double-stranded RNA (targeting a Lamin B1 gene) having the following sequence in water to obtain a concentration of 20 nM.

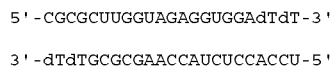

3'-dTdTGCGCGAACCAUCUCCACCU-5'

Crosslinking agent solution

A solution was used as the crosslinking agent solution which was prepared by dissolving the compound 3 of the present invention obtained in Example 3 in a DMSO solution to have a concentration of 40 µM.

(2) Preparation of Transfection Hela Cells

Hela cells (500 µl of DMEM containing Hela cells and 10% of FBS) were spread on a 24-hole plate so as to obtain $1 \times 10^3$ cells/well. After 24 hours passed, the old culture medium was removed, and Hela cells were then washed with a PBS(−) solution. Subsequently, the PBS(−) solution was removed, and 500 µl of DMEM containing 10% of FBS was added per one well. This was used as a transfection Hela cell plate.

(3) Preparation of Transfecting Sample i) Crosslinking of siRNA

Mixing between 4.6 µl of the crosslinking agent solution and 0.46 µl of the siRNA solution was performed, and the mixture thus obtained was still held for 8 hours under light shielding conditions.

ii) Preparation of Sample

As shown in the following Table 10, 90 µl of the Opti-MEM culture medium, 5.06 µl of the reaction solution prepared by the above i) were mixed together, and the mixture thus formed was still held for 15 minutes, so that a transfecting sample was prepared.

In addition, instead of the reaction solution prepared by the above i), by using 0.46 µl of an siRNA solution (a double-stranded RNA which was not crosslinked by the compound of the present invention), a procedure similar to that described above was performed, so that a control sample was prepared.

In this case, 62.6 µg of siRNA was contained in 0.46 µl of 20 nM siRNA solution.

TABLE 10

| | Transfecting sample (5.01 µl) | | |
|---|---|---|---|
| | Opti-MEM (90 µl) | siRNA | Crosslinking agent |
| 1 | + | − | − |
| 2 | + | + Only 20 µM siRNA solution (0.46 µl) is added. | − |
| 3 | + | + | + |

(4) Transfection

Transfection was performed in a manner similar to that in Example 8.

(5) UV Irradiation

UV irradiation was performed in a manner similar to that in Example 8.

(6) Results

After the culture was performed, by a Western blotting method, the amounts of a Lamin B1 protein of the individual samples were quantitatively measured.

The results obtained by the Western blotting of a Lamin B1 protein of the samples and the results obtained by the Western blotting of a β-actin protein of the samples as the control are shown in FIG. 8. In the figure, Lane No. 1 shows the result obtained when sample No. 3 was used, Lane No. 2 shows the result obtained when sample No. 2 was used, Lane No. 3 shows the result obtained when sample No. 1 was used, and Lane No. 4 shows the result obtained when a Hela sample was used which was not transfected with siRNA and the compound 3 of the present invention and which was not irradiated with UV.

In addition, from the results of the Western blotting, the amounts of the Lamin B1 protein of the samples were quantitatively measured.

Figure 9:
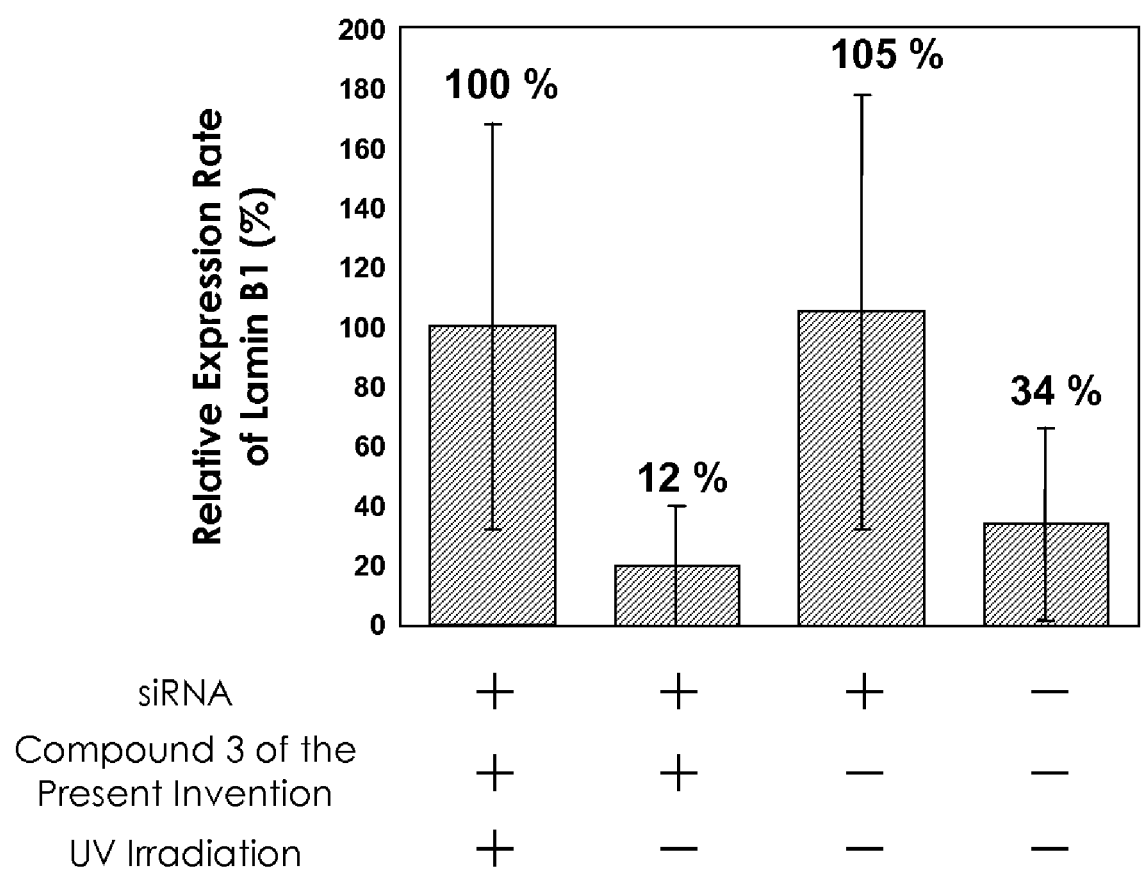
FIG. 9 is a graph showing relative EGFP expression levels of samples obtained in Example 10, the relative expression levels being obtained when an expression ratio by cotransfection of EGFP and DsRed is set to 100%.

The results are shown in FIG. 9. In FIG. 9, the amount of the Lamin B1 protein obtained when a Hela sample was used which was not transfected with siRNA and the compound 3 of the present invention and which was not irradiated with UV was regarded as 100%, and the amounts of the Lamin B1 protein of the samples were represented by relative values.

As is clear from the results shown in FIGS. 8 and 9, it was found that regardless whether siRNA was present or not, the compound of the present invention was present or not, and UV irradiation was performed or not, a gene for β-actin which was not the target of siRNA was always expressed. On the other hand, it was found that the expression of the Lamin B1 which was the target of siRNA was suppressed to 12% by the siRNA (Lane No. 3), the RNAi effect of siRNA could be inhibited when the compound 3 of the present invention was bound to siRNA (Lane No. 2), and in addition, by UV irradiation, the RNAi effect inhibited by the compound 3 of the present invention could be restored (Lane No. 1).

Accordingly, when the compound (crosslinking agent) of the present invention is used, besides a gene transfected from the outside and overexpressed, the expression of an endogenous gene can be controlled by ON and OFF light irradiation.

INDUSTRIAL APPLICABILITY

The present invention provides a crosslinking agent which crosslinks double-stranded nucleic acid, a nucleic acid and a protein or a polypeptide, or proteins or polypeptides, in particular, double-stranded RNA; a crosslinking method using the same; a method for regulating gene expression; and a method for examining a gene function.

According to the present invention, crosslinking between double-stranded nucleic acid, between a nucleic acid and a protein or a polypeptide, or between proteins or polypeptides, and in particular, between double-stranded RNA can be easily formed, and in addition, the above crosslinking can also be easily removed, so that the expression of a target gene can be controlled at an arbitrary timing and location. In addition, the RNAi effect of a double-stranded RNA (siRNA) that cannot be easily inhibited by a conventional caged compound can be inhibited, and the expression of a target gene can be easily controlled at an arbitrary timing and location.

The invention claimed is:

1. A compound represented by formula (7):

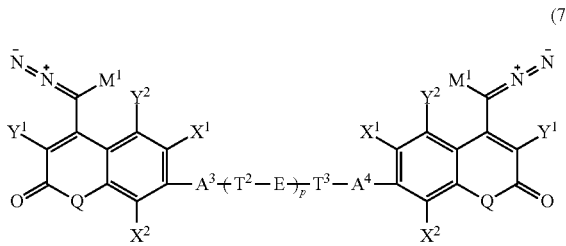 (7)

wherein

Q represents —O—;

$X^1$ and $X^2$ each independently represent —H, a hydroxyl group, a substituted alkoxy group, an unsubstituted alkoxy group, a —OC(O)$R^{11}$ group, a —$NH_3$ group, a —$NR^{11}R^{12}$ group, —$R^{11}$, —F, —Cl, —Br, —I, —COOH, —$NO_2$, —C(=O)$NHR^{11}$, —CN, —CHO, —C(=O)$R^{11}$, or —$SO_3H$;

$Y^1$ represents —H, —Cl, —Br, —I, —C(O)OH, —$NO_2$, —C(O)$NHR^{11}$, —CN, —C(O)H, —C(O)$CH_3$, a benzoxazole-2-yl group, -benzothiazole-2-yl, or -benzoimidazole-2-yl;

$Y^2$ represents —H, —C(O)OH, or —$SO_3H$;

$M^1$ represents —H;

$R^{11}$ and $R^{12}$ each independently represent a substituted or an unsubstituted functional group selected from an alkyl group having 1 to 20 carbon atoms, an alkenyl group having 2 to 20 carbon atoms, an alkynyl group having 2 to 20 carbon atoms, an alkoxy group having 1 to 20 carbon atoms, a thioalkoxy group having 1 to 20 carbon atoms, an alkylsulfonyl group having 1 to 20 carbon atoms, an arylsulfonyl group having 4 to 16 carbon atoms, a heteroalkyl group having a total number of carbon and hetero atoms of 2 to 20, a heteroalkenyl group having a total number of carbon and hetero atoms of 2 to 20, a cycloalkyl group having 3 to 8 carbon atoms, a cycloalkenyl group having 3 to 8 carbon atoms, an aryl group having 4 to 16 carbon atoms, a heteroaryl group having a total number of carbon and hetero atoms of 4 to 16, and a heterocyclyl group having a total number of carbon and hetero atoms of 2 to 30;

$X^1$ and $Y^2$ may form in combination a group selected from an —O—$(CH_2)_n$—O— group, a —C—$(CH_2)_n$—O— group, an —O—$(CH_2)_n$—C— group, an —O—$(CH_2)_n$—N— group, a —N—$(CH_2)_n$—O— group, a —N—$(CH_2)_n$—N— group, a —C—$(CH_2)_n$—N— group, and a —N—$(CH_2)_n$—C— group, in which n is 1 or 2;

$A^3$ and $A^4$ each independently represent an alkylene group, —O—, $NR^1$—, —O—CO—, —CO—O—, —$CH_2$—O—$CH_2$—, —$NR^2$—COO—, —OCO—$NR^2$—, —$NR^3$—CO—, —CO—$NR^3$—, or —O—O—COO—;

$R^1$, $R^2$ and $R^3$ each independently represent hydrogen or an alkyl group;

$T^2$ and $T^3$ each independently represent an alkylene group;

E represents a bond, —NH—, a sulfur atom, an oxygen atom, —O—CO—, or —CO—O—;

p represents an integer of 1 to 6;

each repeat unit of -($T^2$-E)- may be the same or different; and the compound is a symmetrical compound.

2. A crosslinking agent comprising the compound of claim 1 to crosslink nucleic acids.

3. The compound of claim 1, wherein -$A^3$-($T^2$-E)$_p$-$T^3$-$A^4$- is 2 Å to 44 Å in length.

4. The compound of claim 1, wherein -$A^3$-($T^2$-E)$_p$-$T^3$-$A^4$- has a main chain comprising 5 to 80 atoms.

5. The compound of claim 1, wherein -$A^3$-($T^2$-E)$_p$-$T^3$-$A^4$- is

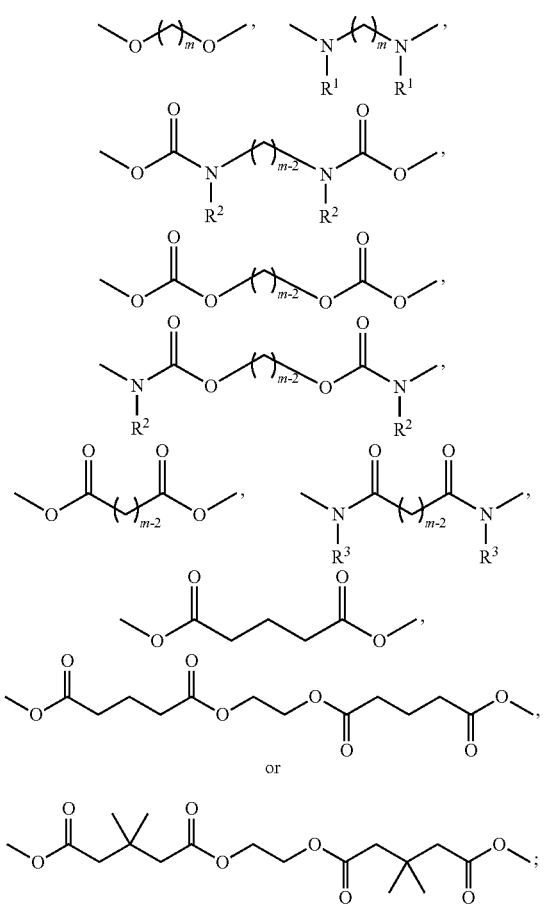

wherein m represents an integer of 3 to 78; and $R^1$, $R^2$ and $R^3$ each independently represent hydrogen or an alkyl group.

6. The compound of claim 1, wherein -$A^3$-($T^2$-E)$_p$-$T^3$-$A^4$- is

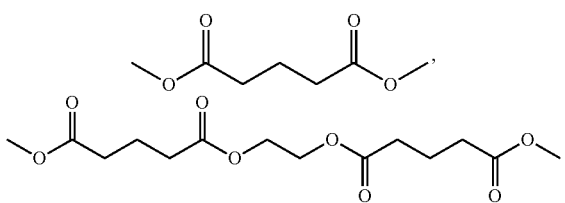

-continued
or
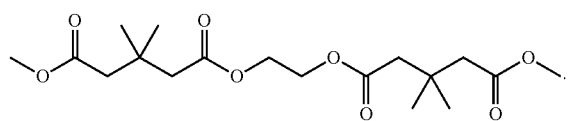
7. The compound of claim 1, wherein
$X^1$ represents —Br;
$X^2$ represents —H;
$Y^1$ represents —H; and
$Y^2$ represents —H.
* * * * *

SEQUENCE LISTING

<160> NUMBER OF SEQ ID NOS: 6

<210> SEQ ID NO 1
<211> LENGTH: 22
<212> TYPE: RNA
<213> ORGANISM: Artificial
<220> FEATURE:
<223> OTHER INFORMATION: Oligonucleotide primer

<400> SEQUENCE: 1
gcaagcugac ccugaaguuc au                                              22

<210> SEQ ID NO 2
<211> LENGTH: 22
<212> TYPE: RNA
<213> ORGANISM: Artificial
<220> FEATURE:
<223> OTHER INFORMATION: Oligonucleotide primer

<400> SEQUENCE: 2
gaacuucagg gucagcuugc cg                                              22

<210> SEQ ID NO 3
<211> LENGTH: 21
<212> TYPE: DNA
<213> ORGANISM: Artificial
<220> FEATURE:
<223> OTHER INFORMATION: Oligonucleotide primer

<400> SEQUENCE: 3
uucuccgaac gugucacgut t                                               21

<210> SEQ ID NO 4
<211> LENGTH: 21
<212> TYPE: DNA
<213> ORGANISM: Artificial
<220> FEATURE:
<223> OTHER INFORMATION: Oligonucleotide primer

<400> SEQUENCE: 4
acgugacacg uucggagaat t                                               21

<210> SEQ ID NO 5
<211> LENGTH: 21
<212> TYPE: DNA
<213> ORGANISM: Artificial
<220> FEATURE:
<223> OTHER INFORMATION: Oligonucleotide primer

<400> SEQUENCE: 5
cgcgcuuggu agagguggat t                                               21

<210> SEQ ID NO 6
<211> LENGTH: 21
<212> TYPE: DNA
<213> ORGANISM: Artificial
<220> FEATURE:
<223> OTHER INFORMATION: Oligonucletotide primer

<400> SEQUENCE: 6
uccaccucua ccaagcgcgt t                                               21